(12) United States Patent
Potsaid et al.

(10) Patent No.: US 9,740,003 B2
(45) Date of Patent: Aug. 22, 2017

(54) COMPACT, LOW DISPERSION, AND LOW ABERRATION ADAPTIVE OPTICS SCANNING SYSTEM AND METHOD

(71) Applicant: Thorlabs, Inc., Newton, NJ (US)

(72) Inventors: Benjamin Michael Potsaid, Cambridge, MA (US); John Joseph Taranto, Oxford, NJ (US); Alex Ezra Cable, Newton, NJ (US)

(73) Assignee: Thorlabs, Inc., Newton, NJ (US)

( * ) Notice: Subject to any disclaimer, the term of this patent is extended or adjusted under 35 U.S.C. 154(b) by 0 days.

(21) Appl. No.: 14/931,994

(22) Filed: Nov. 4, 2015

(65) Prior Publication Data

US 2016/0062112 A1  Mar. 3, 2016

Related U.S. Application Data

(63) Continuation of application No. 14/052,268, filed on Oct. 11, 2013, now Pat. No. 9,200,887.
(Continued)

(51) Int. Cl.
    *G02B 26/00* (2006.01)
    *G02B 27/00* (2006.01)
    (Continued)

(52) U.S. Cl.
    CPC .......... *G02B 27/0068* (2013.01); *A61B 3/102* (2013.01); *A61B 3/14* (2013.01);
    (Continued)

(58) Field of Classification Search
    CPC .... G01B 9/02091; G02B 26/00; G02B 26/08; G02B 26/10; G02B 26/12; G02B 26/127
    (Continued)

(56) References Cited

U.S. PATENT DOCUMENTS 6,381,074 B2   4/2002   Yoshida
6,771,417 B1   8/2004   Wolleschensky et al.
(Continued)

FOREIGN PATENT DOCUMENTS

CA    2267431 A    2/1999
CN    102192714 A   9/2011
(Continued)

OTHER PUBLICATIONS

Chinese First Office Action, dated Nov. 11, 2016, for corresponding application No. 201380051892.1 in China.
(Continued)

*Primary Examiner* — Jonathan Hansen
(74) *Attorney, Agent, or Firm* — Graham Curtin, P.A.

(57) ABSTRACT

An adaptive optics scanning system and method using a beam projection module with four or more axes of motion that can project and control the position and angle of a beam of light to or from an adaptive optics element. The adaptive optics scanning system is compact in size, overcoming the challenges of a traditional lens and mirror based pupil relay design. The adaptive optics scanning system has little to no dispersion, chromatic aberration, and off-axis aberration for improved optical performance. The system and methods for calibrating and optimizing the system are described. A modular adaptive optics unit that scans and interfaces an adaptive optics element is described.

20 Claims, 38 Drawing Sheets

Related U.S. Application Data

(60) Provisional application No. 61/713,478, filed on Oct. 12, 2012.

(51) Int. Cl.

| | | |
|---|---|---|
| *G01B 9/02* | (2006.01) | |
| *G02B 26/08* | (2006.01) | |
| *G02B 26/10* | (2006.01) | |
| *A61B 3/10* | (2006.01) | |
| *A61B 3/14* | (2006.01) | |
| *G02B 21/00* | (2006.01) | |
| *G02B 26/06* | (2006.01) | |

(52) U.S. Cl.
CPC ..... *G01B 9/02055* (2013.01); *G01B 9/02091* (2013.01); *G02B 21/00* (2013.01); *G02B 26/06* (2013.01); *G02B 26/08* (2013.01); *G02B 26/105* (2013.01)

(58) Field of Classification Search
USPC .................................. 356/497; 359/238, 291
See application file for complete search history.

(56) References Cited

U.S. PATENT DOCUMENTS

| | | |
|---|---|---|
| 6,890,076 B2 | 5/2005 | Roorda |
| 7,002,736 B2 | 2/2006 | Fukuyama et al. |
| 7,364,296 B2 | 4/2008 | Miller et al. |
| 7,659,993 B2 | 2/2010 | Feierabend et al. |
| 7,733,564 B2 | 6/2010 | Wolleschensky et al. |
| 7,896,496 B2 | 3/2011 | Hammer et al. |
| 7,942,527 B2 | 5/2011 | Olivier et al. |
| 8,198,604 B2 | 6/2012 | Mertz |
| 2002/0008904 A1 | 1/2002 | Engelhardt |
| 2002/0024007 A1* | 2/2002 | Engelhardt ........ G02B 21/0048 250/234 |
| 2003/0198265 A1 | 10/2003 | Vetrovec |
| 2004/0165250 A1 | 8/2004 | Aubuchon et al. |
| 2005/0263690 A1 | 12/2005 | Araya et al. |
| 2009/0084980 A1 | 4/2009 | Mertz |
| 2009/0137990 A1 | 5/2009 | Sheinis |
| 2011/0134436 A1 | 6/2011 | Podoleanu et al. |
| 2011/0222069 A1 | 9/2011 | Nagahama et al. |
| 2011/0234978 A1 | 9/2011 | Hammer et al. |
| 2012/0002165 A1 | 1/2012 | Saito |
| 2012/0019780 A1 | 1/2012 | Nozato |
| 2012/0044455 A1 | 2/2012 | Hirose |

FOREIGN PATENT DOCUMENTS

| | | |
|---|---|---|
| EP | 2462862 A1 | 6/2012 |
| JP | HEI-11-101942 4 A | 4/1999 |
| WO | 2005060823 A1 | 7/2005 |
| WO | 2011091253 A2 | 7/2011 |

OTHER PUBLICATIONS

International Search Report mailed Feb. 27, 2014 in corresponding International Application No. PCT/US2013/064631.

International Preliminary Report on Patentability mailed Apr. 23, 2015 in corresponding International Application No. PCT/US2013/064631.

Daniel X. Hammer et al. "Adaptive optics scanning laser ophthalmoscope for stabilized retinal imaging," Opt. Express 14, 3354-3367 (2006), https://doi.org/10.1364/OE.14.003354.

Mircea Mujat et al., "High resolution multimodal clinical ophthalmic imaging system," Opt. Express 18, 11607-11621 (2010), https://doi.org/10.1364/OE.18.011607.

Jörgen Thaung et al., "Dual-conjugate adaptive optics for wide-field high-resolution retinal imaging," Opt. Express 17, 4454-4467 (2009), https://doi.org/10.1364/OE.17.004454.

A V Goncharov et al.; "Laboratory MCAO test-bed for developing wavefront sensing concepts," Opt. Express 13, 5580-5590 (2005), https://doi.org/10.1364/OPEX.13.005580.

Biss David P et al; "Towards real-time wavefront sensorless adaptive optics using a graphical processing unit (GPU) in a line scanning system", Opthalmic Technologies XXI, SPIE, vol. 7885, No. 1, Feb. 10, 2011, pp. 1-8, DOI:10.1117/12.876645.

Wang B et al.; "Optimum deformable mirror modes for sensorless adaptive optics", Optics Communications, vol. 282, Issue 23, Dec. 2009, 4467-4474. doi:10.1016/j.optcom2009.08.010.

Extended European Search Report dated Nov. 8, 2016 in corresponding European Application No. 13845913.6.

Bedggood, Phillip; Metha, Andrew; "System design considerations to improve isoplanatism for adaptive optics retinal imaging", Journal of the Optical Society of America A, vol. 27, issue 11, p. A37; DOI: 10.1364/JOSAA.27.000A37; Nov. 1, 2010.

\* cited by examiner

COMPACT, LOW DISPERSION, AND LOW ABERRATION ADAPTIVE OPTICS SCANNING SYSTEM AND METHOD

CROSS-REFERENCE TO RELATED APPLICATIONS

This application is a continuation of U.S. Non-provisional application Ser. No. 14/052,268 filed on Oct. 11, 2013, which claims the benefit of U.S. Provisional Application No. 61/713,478 filed on Oct. 12, 2012. The contents of U.S. Non-provisional application Ser. No. 14/052,268 and U.S. Provisional Application No. 61/713,478 are herein incorporated by reference.

FIELD OF THE INVENTION

The present invention relates to the field of adaptive optics beam scanning.

BACKGROUND

Most optical systems are designed with consideration of the optical aberrations internal to the system only. Careful selection of optical surface geometry combined with precise fabrication, careful assembly, and inclusion of a select few adjustable parameters (e.g. focus, zoom, or spherical aberration correction) allow the optical system to achieve a specified nominal level of performance. However, if a source of optical aberration exists outside of the optical system and the aberrations are unknown and possibly changing with time, the performance of the optical system can be significantly degraded. A select few examples of beam scanning imaging systems and sources of aberration are shown in FIG. 1 and FIG. 2, respectively. Adaptive optics (AO) provides a means to reduce the wavefront distortions caused by the source of aberration to achieve improved performance. In most AO systems, a wavefront correcting device (often a deformable mirror or liquid crystal spatial light modulator) contains several to thousands of individually addressable actuators or cells (pixels) to affect the wavefront, as shown in FIG. 3. Undesirable distortions to the wavefront can be corrected or a more preferable wavefront shape generated with the wavefront correcting device integrated in the optical system. Adaptive optics has been applied to correct for dynamic atmospheric aberration for telescope viewing, to correct for aberrations in the human and animal eye for retinal imaging, to correct for sample induced aberrations for microscopic imaging, to correct for sample induced aberrations in laser material processing, to correct for atmospheric aberrations for line of sight optical communications, and other applications where wavefront correction is desirable. The benefits of adaptive optics are generally improved resolution and signal strength in viewing or imaging applications, tighter focus and higher power density in beam projection applications, or improved communication rates in data transmission applications.

A paper, "The Possibility of Compensating Astronomical Seeing", H. W. Babcock, Publications of the Astronomical Society of the Pacific, Vol. 65, No. 386, p. 229 (1953) first introduced the adaptive optics concept for astronomical viewing with earth based telescopes. The vast majority of adaptive optics systems to date have used the basic AO framework proposed in Babcock's paper with the system containing a wavefront sensor 410, an adaptive optics element 420, and a feedback control system 430 that takes input from the wavefront sensor and generates control signals to drive the adaptive optics element to a preferred wavefront correction shape, as shown in FIG. 4(A). The wavefront sensor could be of a Shack-Hartmann, pyramid, or other wavefront sensing design. An alternate and more recent implementation of AO does not use a wavefront sensor, but instead uses information about the quality of the measured signal as obtained by the image sensor 440 as the input to an optimization algorithm running on an optimization system 450 as part of the process to generate wavefront corrections for the adaptive optics element 460 for improved performance, as shown in FIG. 4(B). Implementing AO in this manner when the wavefront correction is not known a priori and without a dedicated wavefront sensor is commonly referred to as sensorless AO. A third variation of AO uses stored or calculated control signals applied to the adaptive optics element 470 by an open loop control system 480, referred to as open loop AO, as shown in FIG. 4(C).

AO System Aberration Challenges Taught by AO-SLO Examples

The historical challenges of managing system aberrations are described in the context of adaptive optics scanning laser ophthalmoscopes (AO-SLO). It has been long known that the peripheral cornea and crystalline lens in the human eye introduce wavefront distortions that degrade resolution at large pupil diameters. A paper, "Optical quality of the human eye" by F. W. Campbell and R. W. Gubisch, Journal of Physiology, Vol. 186, no. 3, pp. 558-578 (1966), finds that a pupil diameter of 2.4 mm yields the highest optical resolution using linespread analysis. Similar findings in a more recent paper, "Optimal pupil size in the human eye for axial resolution" by W. J. Donnelly III and A. Roorda, JOSA. Vol. 20, Issue 11, pp. 2010-2015 (2003), indicate that a pupil size of 2.46 mm provides the best lateral resolution and 4.6 mm provides the best axial resolution for traditional (non-AO) scanning laser ophthalmoscope (SLO) imaging. The aberration associated with larger pupil sizes dominates and degrades resolution to a greater extent than the improvement of resolution expected with the increasing numerical aperture and associated improved diffraction limit. An adaptive optics element can correct the peripheral cornea and crystalline lens aberrations to allow larger pupil diameters to be used at or near the diffraction limit to achieve significantly improved resolution and imaging performance.

A paper, "Active optical depth resolution improvement of the laser tomographic scanner" by A. Dreher, J. Bille, and R. Weinreb, Appl. Opt. 28, 804-808 (1989) teaches using a deformable mirror in an open loop manner to correct for aberrations in the human eye at a pupil diameter of 6 mm to achieve a two-fold increase in depth resolution in a laser tomographic scanner. Further, the same paper teaches using an afocal 4f arrangement of lenses in a relay configuration to image the active surface of the deformable mirror to the entrance pupil of the eye. An additional afocal 4f arrangement of lenses images the scan pupil of a galvanometer (galvo) scanner to the active surface of the deformable mirror. This basic arrangement and use of multiple 4f relays between the eye, AO element, and scanners has become the standard for nearly all AO systems that perform laser scanning ophthalmic imaging, although the ordering of pupil planes and specific optical components used in the 4f relay can differ. If an additional galvanometer is used to perform 2D scanning, an associated additional 4f relay is used for proper pupil conjugation to the other scanner, adaptive optics element, and pupil planes. The design of the 4f pupil relay has been challenging because off-axis aberrations in the imaging system itself can introduce significant wavefront distortions. The problem is exacerbated because aberrations compound as multiple 4f relays are cascaded in series.

Early point scanning adaptive optics imaging systems used spherical mirrors in off-axis configurations to perform the 4f pupil relay and primarily concentrated on optimizing the image plane performance, as is described in a paper, "Adaptive optics scanning laser ophthalmoscopy" by A. Roorda, F. Romero-Borja, W. Donnelly, III, et al, A. Roorda, F. Romero-Borja, W. Donnelly, III Opt. Express 10, 405-412 (2002) and a related U.S. Pat. No. 6,890,076 B2. However, the in-plane configuration of pupil relays used in this paper and patent is known today to generate considerable residual astigmatism aberration which degrades imaging performance.

A paper "Large-field-of-view, modular, stabilized, adaptive-optics-based scanning laser ophthalmoscope" by S. Burns, R. Tumbar, A. Elsner et al, J. Opt. Soc. Am. A 24, pp. 1313-1326 (2007), teaches that even with small off-axis beam angles on the spherical mirrors in the 4f pupil relay, off-axis astigmatism accumulates with multiple sequential mirror reflections in the system. The paper teaches that designing the optics such that the second pupil relay is constructed out-of-the-plane compared with the first pupil relay, astigmatism can be partially cancelled. A paper, "First-order design of off-axis reflective ophthalmic adaptive optics systems using afocal telescopes" by A. Gómez-Vieyra, A. Dubra, D. Malacara-Hernindez, and D. Williams, Opt. Express 17, pp. 18906-18919 (2009), further investigates off-axis aberrations and develops associated theory to optimize imaging performance in the both the retinal (imaging) and pupil planes by also using an out-of-plane relay configuration. A follow up paper, "Geometric theory of wavefront aberrations in an off-axis spherical mirror" by A. Gomez-Vieyra and D. Malacara-Hernández, Appl. Opt. 50, pp. 66-73 (2011), extends the aberration theory of pupil relays to higher orders and is used as the basis for an improved ophthalmic AO imaging system described in a paper, "Reflective afocal broadband adaptive optics scanning ophthalmoscope" by A. Dubra and Y. Sulai, Biomed. Opt. Express 2, pp. 1757-1768 (2011).

Indeed, the importance of minimizing aberration, and particularly astigmatism, as well as simultaneously minimizing both the aberrations in the imaging planes and the pupil planes was demonstrated by two groups independently publishing images of the elusive rod mosaic in the papers, "Noninvasive imaging of the human rod photoreceptor mosaic using a confocal adaptive optics scanning ophthalmoscope" by A. Dubra, Y. Sulai, J. Norris, R. Cooper, A. Dubis, D. Williams, and J. Carroll, Biomed. Opt. Express 2, pp. 1864-1876 (2011) and "Observation of cone and rod photoreceptors in normal subjects and patients using a new generation adaptive optics scanning laser ophthalmoscope" by D. Merino, J. Duncan, P. Tiruveedhula, and A. Roorda Biomed. Opt. Express 2, pp. 2189-2201 (2011). This second paper also teaches that in addition to introducing scan position dependent wavefront aberrations in both the image and pupil planes, beam wandering also occurs in spherical mirror based 4f pupil relay systems. Beam wandering can be improved with the out-of-plane relay configuration.

Over the course of over a decade, AO based SLO imaging has advanced considerably from systems that could only resolve the relatively large peripheral cone mosaic to being able to resolve the very small rod mosaic in the retina. Paying close attention to the details of the aberrations and quality of pupil relay has been a major contributor to the ever improving imaging performance. However, the resulting size of these new optimized AO imaging systems is quite large due to the long focal lengths of the spherical mirror components used in the highly optimized designs. For example, in the previously mentioned optimized designs, the afocal telescope is over 1.5 meters in length (Dubra, 2011) and 0.4 meters in length (Merino, 2011) because long focal length mirrors are used to reduce off-axis aberration. The large size of the spherical mirror based AO systems is compounded by the need to cascade multiple afocal relays in the AO system, each of considerable length of its own.

Positively powered mirrors and reflective surfaces have been most commonly used in AO-SLO systems because the small back reflections from glass or lens surfaces are significant and can interfere with measurement of the small levels of light returning from the retina. Glass surface back reflections can also generate stray light artifacts and ghost images that degrade wavefront measurement with a wavefront sensor. For these reasons, mirrors have been preferred over lenses and have been used almost exclusively in high performance AO-SLO systems, as described in the before mentioned paper (Gómez-Vieyra, 2009).

A paper, "Lens based adaptive optics scanning laser ophthalmoscope" by F. Felberer, J. Kroisamer, C. Hitzenberger, and M. Pircher, Opt. Express 20, 17297-17310 (2012), teaches that an all lens based implementation of the multiple afocal pupil relays used in an AO-SLO system can achieve a comparable level of aberration as the more complicated out-of-plane spherical mirror based configuration. The lengths of the afocal pupil relays are on the order of 0.5 meters. The problem of backreflections from the glass surfaces interfering with the wavefront measurement is addressed by introducing a polarization beam splitter and polarizer in front of the wavefront sensor and a quarter waveplate in front of the eye such that light reflected from glass surfaces is rejected, but light reflected from the eye is passed through to the wavefront sensor. The problem of backreflections from lens and glass surfaces interfering with the image detection and formation is not addressed. The paper shows results of the rod mosaic, although the quality of the image does not look as good as the images obtained with the all mirror based out-of-plane configuration of the before mentioned Dubra 2011 paper.

The discussion so far has focused on AO-SLO because this technology is one of the most well documented and carefully analyzed of the adaptive optics systems. Other AO systems using different imaging modalities or material processing capability have also been demonstrated and have faced the same off-axis aberration and size challenges, as well as additional challenges associated with dispersions in glass elements when short pulsed lasers are used.

Microscope Imaging with Adaptive Optics

High performance microscope objectives achieve optimal performance when imaging under well controlled and prescribed imaging conditions. Small perturbations to nominal imaging conditions can result in a significant reduction of signal strength and a degradation of resolution. Detrimental perturbations to nominal imaging conditions can arise from using different thickness coverslips, using an oil immersion objective in a water immersion imaging scenario, from imaging into tissue or other samples, from imaging through sample containers, or from other sources. A paper, "Aberration correction for confocal imaging in refractive-index-mismatched media" by M. J. Booth, M. A. A. Neil, and T. Wilson, Journal of Microscopy, Vol. 192, issue 2, (1998) analyzes specimen and sample induced aberration and teaches the potential of using a deformable mirror in a confocal or two photon microscope to correct for aberrations occurring from deep imaging through refractive index mismatched media.

A paper, "Adaptive aberration correction in a two-photon microscope" by M. A. A. Neil, R. Juskaitis, M. J. Booth, T. Wilson, T. Tanaka, and S. Kawata, J. Microscopy, Vol. 200, Pt. 2, pp. 105-108 (2000), describes the first experimental application of two photon imaging with adaptive optics. The adaptive optics corrector, a ferroelectric liquid crystal spatial light modulator (FLCSLM), is located before the scanning mechanism in a commercial laser scanning microscope.

A patent, U.S. Pat. No. 6,381,074 B2, teaches a laser scanning microscope that includes a wavefront converting element to perform scanning of the focus in the optical axis (depth) direction without the need to change the distance between the microscope objective and the specimen. Aberration occurring during the depth scanning is canceled by using the wavefront converting element to minimize the degradation of light collecting performance due to the scanning in the optical axis direction. The wavefront converting element is placed at or near a position conjugate to the objective pupil position so that predetermined conditions are satisfied. Further, the wavefront converting element and each of two galvanometer mirrors in the scanning optical system to scan the position where light is collected in a direction perpendicular to the optical axis and further the pupil position of the objective are all placed in conjugate or nearly conjugate relation to each other by the intervening optical systems. The scanning optical system includes a pupil projection lens for placing the wavefront converting element and the galvanometer mirror closer to the wavefront converting element in conjugate relation to each other.

A paper, "Smart microscope: an adaptive optics learning system for aberration correction in multiphoton confocal microscopy" by O. Albert, L. Sherman, G. Mourou, T. Norris, and G. Vdovin, Opt. Lett. 25, 52-54 (2000) teaches using a deformable mirror to correct for off-axis aberrations in a two photon imaging system. The objective is an off-axis parabolic mirror and the intensity of a two photon sample is used to optimize the deformable mirror shape.

A paper, "Adaptive aberration correction in a confocal microscope" by M. J. Booth, M. A. A. Neil, R. Juskaitis and T. Wilson, Proc. Nat. Acad. Sci., Vol. 99, No. 9, 30, pp. 5788-5792 (2002), describes the first demonstration of adaptive optics in a confocal microscope. The paper teaches using relay lenses between the deformable mirror and the objective.

A paper, "Adaptive correction of depth-induced aberrations in multiphoton scanning microscopy using a deformable mirror" by Sherman L, Ye J Y, Albert O, Norris T B. J Microsc. 206 (Pt 1):65-71 (2002), demonstrates using a deformable mirror as the wavefront corrector in a multiphoton scanning microscope. The paper teaches using a 4f telescope system to directly image the face of the DM to the entrance pupil of the microscope objective.

A patent, U.S. Pat. No. 6,771,417 B1, teaches the use of one or more wavefront modulators in the observation beam path and/or illumination beam path of a microscope. The patent teaches placing the wavefront modulator between the tube lens and the objective. Such modulators may be adapted to change the phase and/or the amplitude of light in such a way to carry out displacement and shaping of the focus in the object space and correction of possible aberrations. An embodiment of the invention allows focusing to different depths without changing the distance from the objective to the object. The possible areas of use include confocal microscopy, laser-assisted microscopy, conventional light microscopy and analytic microscopy.

A patent, U.S. Pat. No. 7,733,564 B2 (continuation patent of above mentioned U.S. Pat. No. 6,771,417 B1), includes additional claims in which a design change to the instrument of placing the wavefront modulator in a pupil plane is claimed, although the methods and mechanisms for doing so are not described.

A patent, U.S. Pat. No. 7,659,993 B2, teaches a wavefront sensing device within an adaptive optics microscope architecture. An embodiment of the invention is described for fluorescent imaging with examples of multi-photon and confocal microscopy. A wavefront sensor uses interferometric techniques, called coherence gating, to isolate a depth of interest in the sample. The deformable mirror is adapted to a predetermined shape in order to form the desired wavefront of the travelling light pulses. Specimen scanning is obtained with movement of the specimen holding device.

The challenges of using the before mentioned and traditional approach of cascading multiple pupil relays in microscopy has been recognized. A patent, U.S. Pat. No. 7,002,736 B2, teaches a scanning optical microscope using a wavefront converting element to correct for aberrations. Citing Japanese patent, HEI-11-101942 4 (1999), which teaches that it is desirable that the wavefront converting element should be placed at a position conjugate to the pupil, the patent emphasizes that it is difficult to implement pupil relay systems because of the following problems. A first problem is that a variety of objectives are used in microscopic observation, and the pupil position differs for each objective. Therefore, when a plurality of objectives are switched from one to another to perform observation, it is difficult to keep the pupils of the objectives in conjugate relation to the wavefront converting element at all times. Further, the wavefront converting element needs to be placed in conjugate relation to the position of a laser scanning member and also to the position of the objective pupil. Accordingly, at least two pupil relay optical systems are required. Therefore, the apparatus becomes large in size and complicated unfavorably.

Adaptive optics have been used in a microscope for reasons other than to correct optical aberrations. A patent, U.S. Pat. No. 8,198,604 B2, teaches a system for providing enhanced background rejection in thick tissue that contains an aberrating element for introducing controllable extraneous spatial aberrations in an excitation beam path. An associated method comprises the steps of acquiring two-photon excited fluorescence of thick tissue without extraneous aberrations; introducing an extraneous aberration pattern in an excitation beam path; acquiring two-photon excited fluorescence of the thick tissue having the introduced extraneous aberration pattern; and subtracting the two-photon excited fluorescence with extraneous aberrations from the acquired standard two-photon excited fluorescence of the thick tissue without extraneous aberrations. The deformable mirror is relayed to the beam scanner, which is in turn relayed to the back aperture of the objective. The deformable mirror is located in a conjugate plane of the objective back aperture.

OCT Imaging with Adaptive Optics

Similar to AO-SLO, adaptive optics has been applied to Optical Coherence Tomography (OCT) for adaptive optics OCT (AO-OCT).

A patent, U.S. Pat. No. 7,364,296 B2, teaches a method of optical imaging comprising providing a sample to be imaged, measuring and correcting aberrations associated with the sample using adaptive optics, and imaging the sample by optical coherence tomography.

A patent, U.S. Pat. No. 7,942,527 B2, teaches using a Badal optometer and rotating cylinders inserted in an AO-OCT system to correct large spectacle aberrations such as myopia, hyperopic and astigmatism for ease of clinical use and reduction. Similar to as implemented with AO-SLO, spherical mirrors in the telescope are rotated orthogonally (out-of-plane) to reduce aberrations and beam displacement caused by the scanners. This produces greatly reduced AO registration errors and improved AO performance to enable high order aberration correction in patient eyes.

A patent, U.S. Pat. No. 7,896,496 B2, teaches an object tracking system that can be used for AO-SLO or AO-OCT.

A patent application, WO2005060823 A1, teaches a data acquisition system where measurements are made by OCT, wherein a quality of these measurements is improved by arranging an active optical element in the beam path, the system also including a wavefront sensor.

A patent application. US20120019780 A1, teaches an AO-SLO or AO-OCT.

A patent application, US20110234978 A1, teaches a multifunctional optical apparatus that includes a system of optical components capable of operating in a scanning laser ophthalmoscope (SLO) mode and an optical coherence tomography (OCT) mode. Multiple scanning devices are positioned at pupil conjugates in the system of optical components. The system may include optical tracking along with one or more optional adaptive optics.

A patent application, US20120002165 A1, teaches an invention that can image with SLO or OCT that has multiple measuring beams and uses adaptive optics that include: a wavefront aberration detector for detecting a wavefront aberration in a reflected or backscattered beams generated when a plurality of beams are scanned on a surface, and a single wavefront aberration corrector for correcting a wavefront aberration in each of the plurality of beams, based on the wavefront aberration, and the plurality of beams enter the single wavefront aberration corrector with different incident angles and are overlapped on each other. In one embodiment, the wavefront aberration corrector is disposed at a position at which an exit pupil of relay optics is acquired optically conjugate with the single position at which the plurality of beams intersect with each other.

A patent application, US20120044455 A1, teaches an AO-SLO or AO-OCT imaging apparatus using a deformable mirror and wavefront sensor. Pupil relay optics are used and the patent application teaches that relay lenses are used so that the cornea, the XY scanner, and the wavefront sensor become approximately optically conjugate with each other.

Material Processing and Object Manipulation with Adaptive Optics

Various papers have described using adaptive optics for beam shaping in material processing applications, including a paper, "Beam delivery by adaptive optics for material processing applications using high-power CO2 lasers" by Heinz Haferkamp and Dirk Seebaum, Proc. SPIE 2207, Laser Materials Processing: Industrial and Microelectronics Applications, 156 (1994), and a paper, M. Geiger, Synergy of Laser Material Processing and Metal Forming, CIRP Annals—Manufacturing Technology, Volume 43, Issue 2, pp. 563-570 (1994).

Adaptive optics have been used to correct for sample induced aberration in material processing. A paper, "Active Aberration Correction for the Writing of Three-Dimensional Optical Memory Devices" by M. Neil, R. Juskaitis, M. Booth, T. Wilson, T. Tanaka, and S. Kawata, Appl. Opt. 41, 1374-1379 (2002), teaches using an SLM to compensate for sample induced aberrations when writing 3D optical memory devices. A paper, "Ultrafast laser writing of homogeneous longitudinal waveguides in glasses using dynamic wavefront correction", C. Mauclair, A. Mermillod-Blondin, N. Huot, E. Audouard, and R. Stoian, Opt. Express 16, 5481-5492 (2008), teaches using an SLM in a laser processing system to improve the quality of laser processing. A paper, "Adaptive optics for direct laser writing with plasma emission aberration sensing" by A. Jesacher, G. Marshall, T. Wilson, and M. Booth, Opt. Express 18, 656-661 (2010), teaches using an SLM in a plasma emission direct laser writing system.

Adaptive optics have been used for optical manipulation. One method of manipulating small objects is to use optical trapping, sometimes referred to as optical tweezers. Most methods of using optical tweezers do not include a galvo based scanning mechanism as taught in the following papers: "Adaptive optics in an optical trapping system for enhanced lateral trap stiffness at depth", by M C Miillenbroich, N McAlinden and A J Wright, M C Mfillenbroich et al, J. Opt. 15 075305 (2013), a paper, "Holographic optical tweezers aberration correction using adaptive optics without a wavefront sensor" by K D. Wulff, D G. Cole, R L. Clark, R D Leonardo, J Leach, J Cooper, G Gibson, M J. Padgett, Proc. SPIE 6326, Optical Trapping and Optical Micromanipulation III, 63262Y (2006), and a thesis, "Design and characterization of an optical tweezers system with adaptive optic control" by S. Bowman (2009).

More advanced optical trapping setups include scanning and/or beam splitting capability, such as a paper, "Combined holographic-mechanical optical tweezers: Construction, optimization, and calibration", by Richard D. L. Hanes, Matthew C. Jenkins, and Stefan U. Egelhaaf, Rev. Sci. Instrum. 80, 083703 (2009). In this paper, the SLM is placed near the objective and not explicitly conjugated to the aperture. The SLM allows multiple traps to be formed such that the galvos can do coarse steering of the beam and the SLM can perform beam splitting to generate multiple traps and fine steering of the beam. The deformable mirror used in the apparatus is calibrated by optimizing oscillatory drag force on a trapped object.

SUMMARY

An embodiment of the present invention is an adaptive optics scanning system and methods for its calibration and operation. The unique design of the adaptive optics scanning system of an embodiment of the present invention overcomes limitations in prior art related to large size, dispersion, chromatic aberration, and off-axis aberration. An embodiment of the present invention enables a reduction in size by replacing static optical elements used in a traditional design with active optical elements to achieve proper beam centration with respect to the adaptive optics component. An embodiment of the present invention eliminates the need for the 4f relays between the scanning mirrors, while at the same time increases instrument performance, flexibility and capability. An embodiment of the present invention overcomes the challenges of off-axis aberration associated with the traditional lens based and concave mirror based pupil relay configurations used in most adaptive optics systems by using only flat or nearly flat reflective surfaces. An embodiment of the present invention overcomes the detrimental effects of dispersion and chromatic aberration associated with lens based designs by using only reflective mirrors. An embodiment of the present invention enables improved adaptive optics performance in a small form factor. An embodiment of the present invention enables programmable flexibility for accommodating different sample delivery optics. Moreover, an embodiment of the present invention is compatible with a wide range of imaging modalities, processing methods, and characterization methods used in biological, medical, industrial imaging and inspection. The possible areas of use include medical imaging, biological imaging, industrial inspection, material processing, material inspection, subsurface imaging, surface profiling, distance ranging and measurement, fluid flow characterization and analysis, and investigation and characterization of material polarization properties.

One embodiment provides an adaptive optics scanning system including: an emission source for generating light, the light being directed through the adaptive optics scanning system to a sample; one or more adaptive optics element(s), the adaptive optics element(s) affecting the wavefront, affecting the intensity, or affecting both the wavefront and intensity of the light; a beam projection module, the beam projection module operating with four or more axes of motion and controlling an angle and position of the light to preferentially interface the adaptive optics element by creating or accommodating a beam pivot point at or near the adaptive optics element(s) while scanning the light across the sample; a controller for controlling motion trajectories of the axes in the beam projection module; sample delivery optics, the sample delivery optics appropriately conditioning and directing the light to the sample; one or more detector(s), the detector(s) measuring light from the sample.

One embodiment provides a modular adaptive optics unit including: one or more entrance ports, the entrance ports allowing one or more optical beams to enter the modular adaptive optics unit; one or more output ports, the output ports being located along one or more beam paths at which the optical beam may transit or be terminated; one or more adaptive optics element(s), the adaptive optics element(s) affecting the wavefront, affecting the intensity, or affecting both the wavefront and intensity of the light beam; a set of beam steering elements, the beam steering elements creating four or more axes of motion that affect an angle of, or the transverse position of, the propagation path of the light to preferentially create at least one effective rotation point about which the light beam is pivoted; a means for controlling the trajectories of the beam steering elements to direct the light beam along preferential paths.

DETAILED DESCRIPTION OF THE PREFERRED EMBODIMENTS

Figure 1:
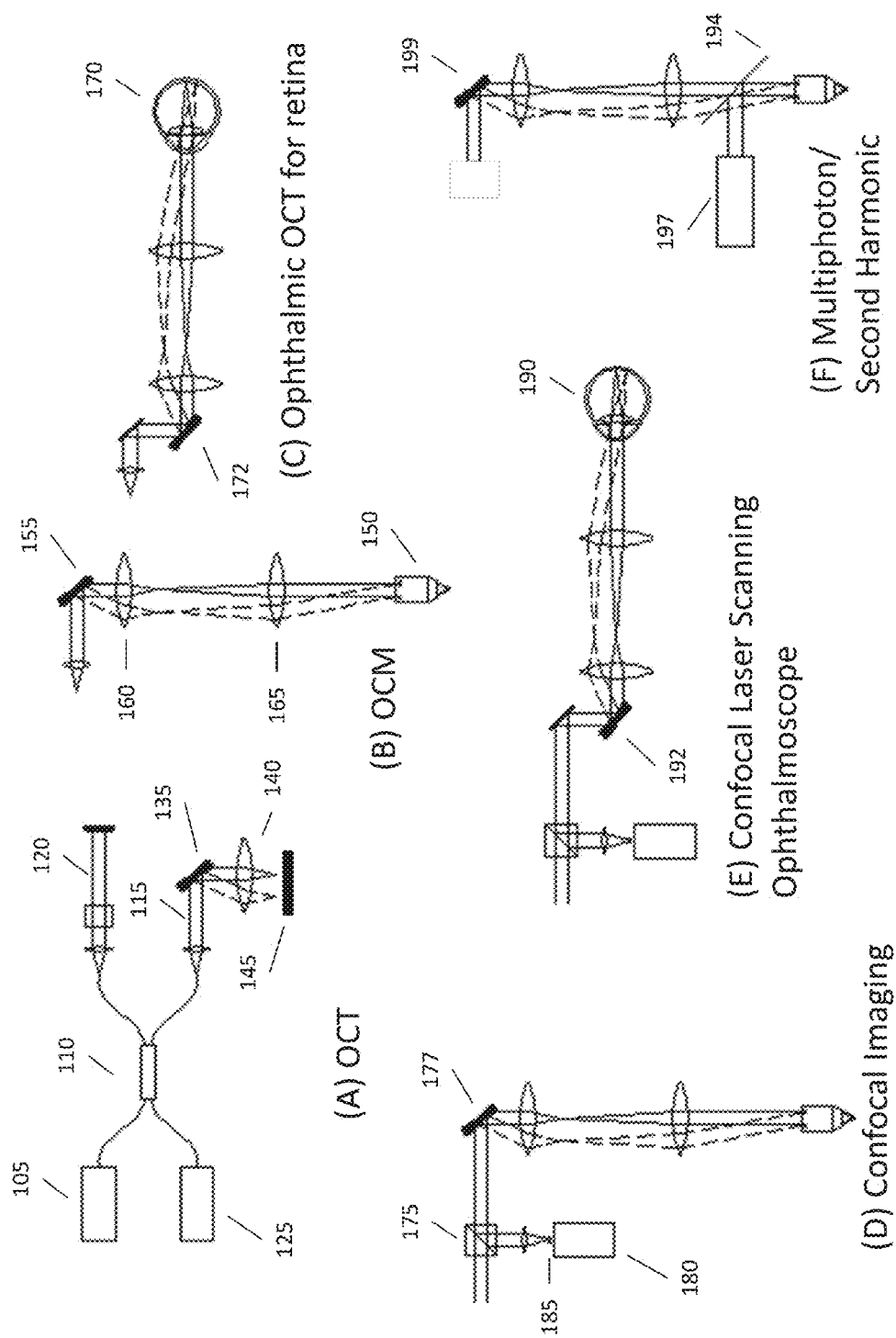
FIG. 1 is a collection of diagrams showing several of many example optical systems and imaging modalities that can use an embodiment of the present invention.

The description of illustrative embodiments according to principles of the present invention is intended to be read in connection with the accompanying drawings, which are to be considered part of the entire written description. In the description of embodiments of the invention disclosed herein, any reference to direction or orientation is merely intended for convenience of description and is not intended in any way to limit the scope of the present invention. Relative terms such as "lower," "upper," "horizontal," "vertical," "above," "below," "up," "down," "top" and "bottom" as well as derivative thereof (e.g., "horizontally," "downwardly," "upwardly," etc.) should be construed to refer to the orientation as then described or as shown in the drawing under discussion. These relative terms are for convenience of description only and do not require that the apparatus be constructed or operated in a particular orientation unless explicitly indicated as such. Terms such as "attached," "affixed," "connected," "coupled," "interconnected," and similar refer to a relationship wherein structures are secured or attached to one another either directly or indirectly through intervening structures, as well as both movable or rigid attachments or relationships, unless expressly described otherwise. Moreover, the features and benefits of the invention are illustrated by reference to the exemplified embodiments. Accordingly, the invention expressly should not be limited to such exemplary embodiments illustrating some possible non-limiting combination of features that may exist alone or in other combinations of features; the scope of the invention being defined by the claims appended hereto.

This disclosure describes the best mode or modes of practicing the invention as presently contemplated. This description is not intended to be understood in a limiting sense, but provides an example of the invention presented solely for illustrative purposes by reference to the accompanying drawings to advise one of ordinary skill in the art of the advantages and construction of the invention. In the various views of the drawings, like reference characters designate like or similar parts.

Discussion of Adaptive Optics

Adaptive optics (AO) enable the correction of optical aberrations to improve the performance of optical imaging, optical processing of materials, optical profilometry, optical inspection, and other optical characterization in which system, sample, or externally induced optical aberrations degrade optical performance. Adaptive optics was originally proposed for astronomical imaging with telescopes to compensate for aberrations introduced by the atmosphere. Using an adaptive optics element (sometimes called a wavefront corrector) and wavefront sensor in a closed loop control system, it is possible to measure the aberrations in the atmosphere and generate a corrective shape on the adaptive optics element in real time to reduce the level of aberration to yield an improved image quality. Image quality generally improves in signal strength and resolution. Adaptive optics have also been used in laser cavities, laser beam shaping, biomedical imaging, microscopy, and materials processing to preferentially shape or correct the wavefront. Environmental influences, thermal effects, biological processes, sample holder materials and properties, the sample itself, and other sources of aberration often degrade the performance of an optical system or instrument. Adding an adaptive optics element to an optical system or instrument can often correct the aberrations to achieve improved performance.

In astronomical imaging, it is generally understood that it is desirable to locate the adaptive optics element optically conjugate to the source of the aberration, which is generally a turbulent layer of the atmosphere. Using multiple adaptive optics elements in a multi-conjugate configuration (different adaptive optics elements are conjugated to different turbulent atmospheric layers), it is possible to improve the aberration correction and achieve a larger field of view than is instantaneously correctible by a particular set of adaptive optics corrections, a concept related to improving the size of the isoplanatic patch. Although the definition of the isoplanatic patch differs in the literature, the isoplanatic patch describes the similarity of wavefront with change in field position and is most commonly described with respect to correcting aberration with an 'ideal' wavefront corrector or correctors. A large isoplanatic patch implies that the wavefront changes slowly with field position such that a single ideal adaptive optics correction, or single set of corrections on different adaptive optics elements, would be able to correct the wavefront over a large field of view. A small isoplanatic patch implies that the wavefront changes quickly with field position such that a single adaptive optics correction, or single set of corrections on different adaptive optics elements, would only be able to correct the wavefront over a small field of view. The isoplanatic patch does not, however, indicate how well an adaptive optics system will perform in practice as the adaptive optics element may or may not have the ability to generate a wavefront correction with sufficient spatial frequency, stroke, or temporal dynamic performance.

Figure 5:
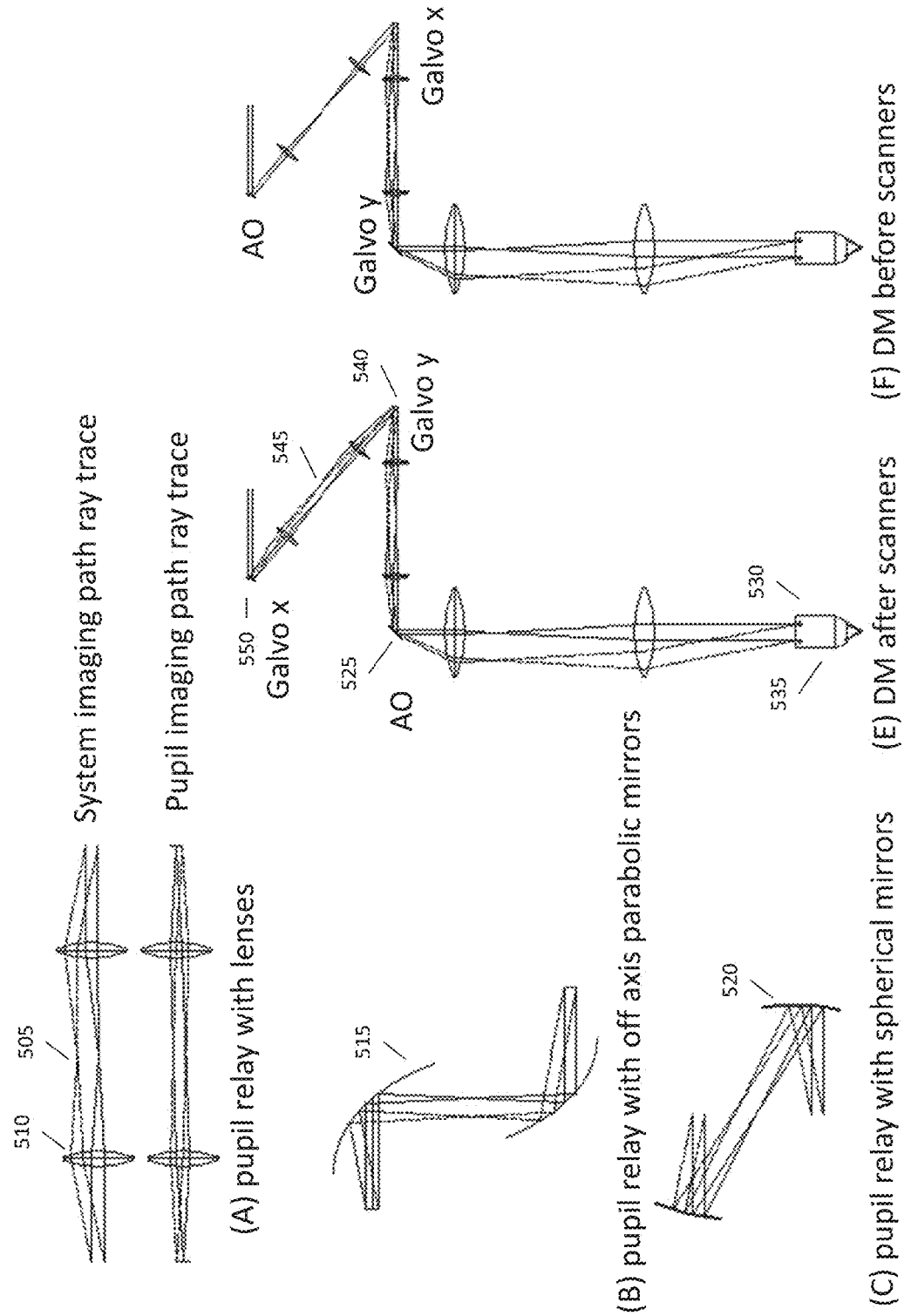
FIG. 5 is a collection of diagrams showing pupil relay implementations that are used in optical systems with additional diagrams showing how the relative order of optical beam steering and adaptive optics components can be varied.

In high numerical aperture laser scanning through a well corrected (low aberration) objective, most prior literature has taught locating the adaptive optics element in a plane that is conjugate to the pupil plane of the objective. In ophthalmic imaging, the adaptive optics element is most commonly located in a plane conjugate to the pupil of the eye. FIG. 5 shows example pupil relay configurations. An afocal 4f relay 505, or sometimes called 4f telescope, is the most common method to achieve conjugation between a pupil plane and an adaptive optics element. The 4f relay may uses lenses 510, off-axis parabolic mirrors 515, spherical mirrors 520, combinations of lenses and mirrors, or other optics. With a 4f relay, wavefront perturbations to the beam are often relayed from the adaptive optics element 525 into the pupil plane 530 of the objective 530. With a 4f relay, the relative light intensity distribution is preserved between the two planes as desired. For the purposes of this patent application discussion, a 4f relay can preserve the beam diameter, expand the beam diameter, or reduce the beam diameter, depending on the focal lengths of the constituent components. Adaptive optics scanning systems often require beam steering in addition to adaptive optics correction. An additional pupil relay consisting of a 4f telescope is often included in an adaptive optics scanning system to relay the pupil from an adaptive optics element 525 to a steering mirror 540. If the steering mirror has two degrees of freedom, as is the case with a fast steering mirror (FSM), both axes of rotation can be coincident with the pupil plane using the one additional 4f relay. However, FSM mirrors are often not as fast as single axis galvanometer driven mirrors. Consequently, most AO beam scanning imaging systems use two separate galvo driven mirrors. It is well known that placing two separate galvo driven mirrors in close proximity to achieve x and y scanning results in the axis of rotation being separated by a distance. This distance may be small, but it means that it is impossible to locate both axes precisely in the same conjugate pupil plane. In adaptive optics scanning systems where small perturbations to the wavefront can degrade performance, it is common to include an additional pupil relay 545 between the two separate galvo driven mirrors 540 and 550. Indeed, most successful adaptive optics scanning systems demonstrated to date use separate galvo driven mirrors separated by 4f relays. The 4f relay between an x direction scan galvo mirror 550 and a y direction scan galvo mirror 540 properly aligns the center of the beam with each of the scan mirrors. A 4f relay between one of the scan mirrors 540 and the adaptive optics element 525 achieves proper beam steering on the adaptive optics element. The ordering of adaptive optics element and galvo mirrors can change, as shown in FIGS. 5(E) and 5(F). The 4f relays can be constructed of lenses, mirrors, or a combination of lenses and mirrors. While it may be possible to design a single 4f relay with good (diffraction limited) off-axis performance, generally the 4f relay is composed of optical elements with mostly positive power so it is difficult or impossible to completely balance aberrations. Cascading multiple 4f relays results in the aberration contributions of the positive powered elements to compound. Consequently, it is difficult to achieve good (diffraction limited) performance through multiple serially chained 4f relays, as is commonly implemented. The result is that most adaptive optics systems use long working distance lenses or mirrors to reduce aberrations with the disadvantage of a large size. Additional improvements have been obtained by using inconvenient out-of-plane optical configurations to reduce compounding of aberrations, as has been shown when using off-axis spherical mirrors. The serial chaining of 4f relays has been a common method for conjugating the adaptive optics element to the pupil plane of the objective and for properly steering the beam. However, the serial chaining of 4f relays suffers from a large size and off-axis aberrations when using lenses or mirrors, and chromatic aberrations and dispersion when using lenses. Dispersion increases with increasing thickness or number of glass elements. Dispersion is problematic when using short pulsed lasers because the pulses are dispersively broadened in time. An embodiment of the present invention addresses these significant shortcomings of prior art designs. An embodiment of the present invention enables a very compact and flexible adaptive optics scanning system with little to no: dispersion, chromatic aberration, and off-axis aberration for improved optical and imaging performance.

Applications of Embodiments of the Present Invention

An embodiment of the present invention is an adaptive optics scanning system. In a scanning optical system, light is scanned across a sample. Scanning optical systems can be used for a wide range of imaging, processing, manipulation, or characterization applications.

FIG. 1 shows examples of several imaging modalities and systems that can be used with and embodiment of the present invention. It will be understood that other imaging modalities and systems not shown can also be used with an embodiment of the present invention. A common application scans light across the sample for the purposes of learning something about or measuring a characteristic of the sample. For example, in one embodiment, the adaptive optics scanning system performs imaging of the sample. The imaging may be performed by confocal, multiphoton, second harmonic, reflected light, fluorescent, scattered light, or any other method of imaging a sample with a scanned beam of light. The imaging may be one dimensional (1D), two dimensional (2D), three-dimensional (3D), or possibly 1D, 2D, or 3D as a function of time to image dynamic processes. The imaging may be wavelength selective and possibly multicolor or multichannel, such as is often performed in fluorescent imaging. A more general form of imaging seeks to obtain spectroscopic information about the sample. In one embodiment, the adaptive optics scanning system performs spectroscopy of the sample. Often, a scanning optical system is used to obtain material specific information about the sample, such as biological cell type, as is commonly performed in fluorescent imaging, or scattering properties of a sample, as is commonly performed with optical coherence tomography (OCT). Other applications are only concerned with the shape or profile of the sample. In one embodiment, the adaptive optics scanning system performs profilometry. In general, it is desirable that imaging or characterization of a sample be non-destructive and not change the sample itself. Often, however, photobleaching, heating, or other sample changing phenomena occur as a byproduct of imaging. Other applications seek to specifically modify or affect the sample with the scanned beam, such as in laser machining, ablation, stimulation, heating, or optical manipulation. In one embodiment, the adaptive optics scanning system performs processing of the sample. In another embodiment, the adaptive optics scanning system performs manipulation of the sample. In another embodiment, the adaptive optics scanning system performs profiling of the sample. In another embodiment, the adaptive optics scanning system performs stimulation of a region of the sample. In another embodiment, the adaptive optics scanning system performs heating of a region of the sample.

FIG. 1(A) shows an optical layout for an optical coherence tomography (OCT) system. In one embodiment, the adaptive optics scanning imaging system performs optical coherence tomography (OCT). When performing OCT, an embodiment of the present invention may further comprise an interferometer 110, a sample path 115, and a reference path 120 for obtaining an interferometric OCT signal from the sample 145. Scanners 135 and an objective lens 140 allow a focused spot of light to be scanned across the sample 145. OCT can be performed using a variety of methods, include time domain, spectral/Fourier domain, or swept source/Fourier domain, sometimes referred to as optical frequency domain imaging (OFDI). OCT can also be performed using a high numerical aperture objective 150, called optical coherence microscopy (OCM). In OCT, low numerical aperture objectives are often used to provide sufficient depth of field because information is often obtained along a relatively long depth range of an A-scan. The definition of high vs. low numerical aperture is somewhat subjective. For the purposes of this application, high numerical aperture refers to apertures commonly found in commercial microscope objectives. FIG. 1(B) shows an optical layout for the sample path of an OCM system that would be connected to an OCT interferometer. Collimated light is directed to a scanner 155 and through a scan lens 160 and tube lens 165 to the objective 150. In one embodiment, the adaptive optics scanning system performs optical coherence microscopy (OCM). When performing OCM imaging, an embodiment of the present invention may further comprise an interferometer, a sample path, and a reference path for obtaining an interferometric OCT/OCM signal and a high numerical aperture objective 150 for obtaining fine resolution sample data. One common application of OCT is imaging the eye 170, as shown in FIG. 1(C). In one embodiment, the adaptive optics scanning system performs OCT of an eye 170. The retina is the most common part of the eye imaged with OCT, however imaging of the anterior eye, crystalline lens, and cornea can also be performed.

In another embodiment, the adaptive optics scanning system performs confocal imaging. An example confocal imaging system is shown in FIG. 1(D). When performing confocal imaging, the adaptive optics scanning system may further comprise a beam splitter or dichroic mirror 175 and detector 180 and confocal pinhole 185 to achieve depth sectioned fluorescence or reflectance imaging. Sometimes the end of a single mode or multimode fiber is used as a confocal pinhole. A scanning laser ophthalmoscopes (SLO) is a variation of confocal imaging that is useful for imaging the eye 190. An example SLO imaging system is shown in FIG. 1(E). In one embodiment, the adaptive optics scanning system is an SLO system. An embodiment of the present invention can also be used with nonlinear imaging modalities. An example multiphoton/second harmonic imaging system is shown in FIG. 1(F). In one embodiment, the adaptive optics scanning system performs two-photon imaging. When performing two-photon imaging, the imaging system may further comprise a dichroic mirror 194 in the light path and the detector 735 measures ballistic and multiply scattered fluorescent or emitted light from the sample. Three-photon and other multiphoton imaging can also similarly be performed. In one embodiment, the adaptive optics scanning system performs multi-photon imaging. When performing multi-photon imaging, the adaptive optics scanning system may further comprise a dichroic mirror 194 in the light path and the detector 197 measures ballistic and multiply scattered fluorescent or emitted light from the sample. Many multiphoton imaging systems can also be used for second harmonic imaging. In one embodiment, the adaptive optics scanning system performs second harmonic imaging. In another embodiment, the adaptive optics scanning system performs fluorescent imaging. More generally, an embodiment of the present invention can be used for a wide range of applications where a light beam is scanned on or in a sample and information about the sample obtained by collecting light from the sample. In addition to fluorescent and nonlinear imaging, more standard reflection and transmission imaging can be performed. In one embodiment, the adaptive optics scanning system performs reflection imaging. In another embodiment, the adaptive optics scanning system performs transmission imaging. Most imaging applications use a single channel of spectral detection or a small number of spectral channels that are sufficient to differentiate sample characteristics. Other applications seek to spectrally resolve regions of the sample using spectroscopy. In one embodiment, the adaptive optics scanning system performs spectroscopy. When performing spectroscopy, the adaptive optics scanning system may further comprise a spectrometer for resolving a spectral content of the light from the sample.

There are many laser scanning applications that can benefit from adaptive optics to achieve improved performance. Therefore an embodiment of the present invention may be used on a wide range of samples associated with biological, medical, industrial, and research fields. Some example samples include: a biological specimen, animal, portion of an animal, human, portion of a human, plant, portion of a plant, tissue, living tissue, preserved tissue, stained tissue, a biological organ, a biopsy specimen, an eye, a portion of an eye, a brain, a portion of a brain, or skin. Other example samples comprise: a mechanical component, an electrical component, an optical component, a fabricated component, an assembly of components, a material specimen, a semiconductor component, a semiconductor material specimen, a metal component, a glass component, a plastic component, an inanimate organic specimen, a crystal specimen, or a mineral specimen. More generally, samples that can be used with an embodiment of the present invention would be characterized by a property of the sample. The sample can be characterized with respect to dimensional properties. The sample can be characterized with respect to mechanical properties. The sample can be characterized with respect to optical properties. The sample can be characterized with respect to fluorescent properties. The sample can be characterized with respect to reflection properties. The sample can be characterized with respect to transmission properties. The sample can be characterized with respect to index of refraction. The sample can be characterized with respect to scattering properties. The sample can be characterized with respect to dispersive properties. The sample can be characterized with respect to spectroscopic properties. The sample can be characterized with respect to polarization properties. The sample can be characterized with respect to thermal properties.

Figure 2:
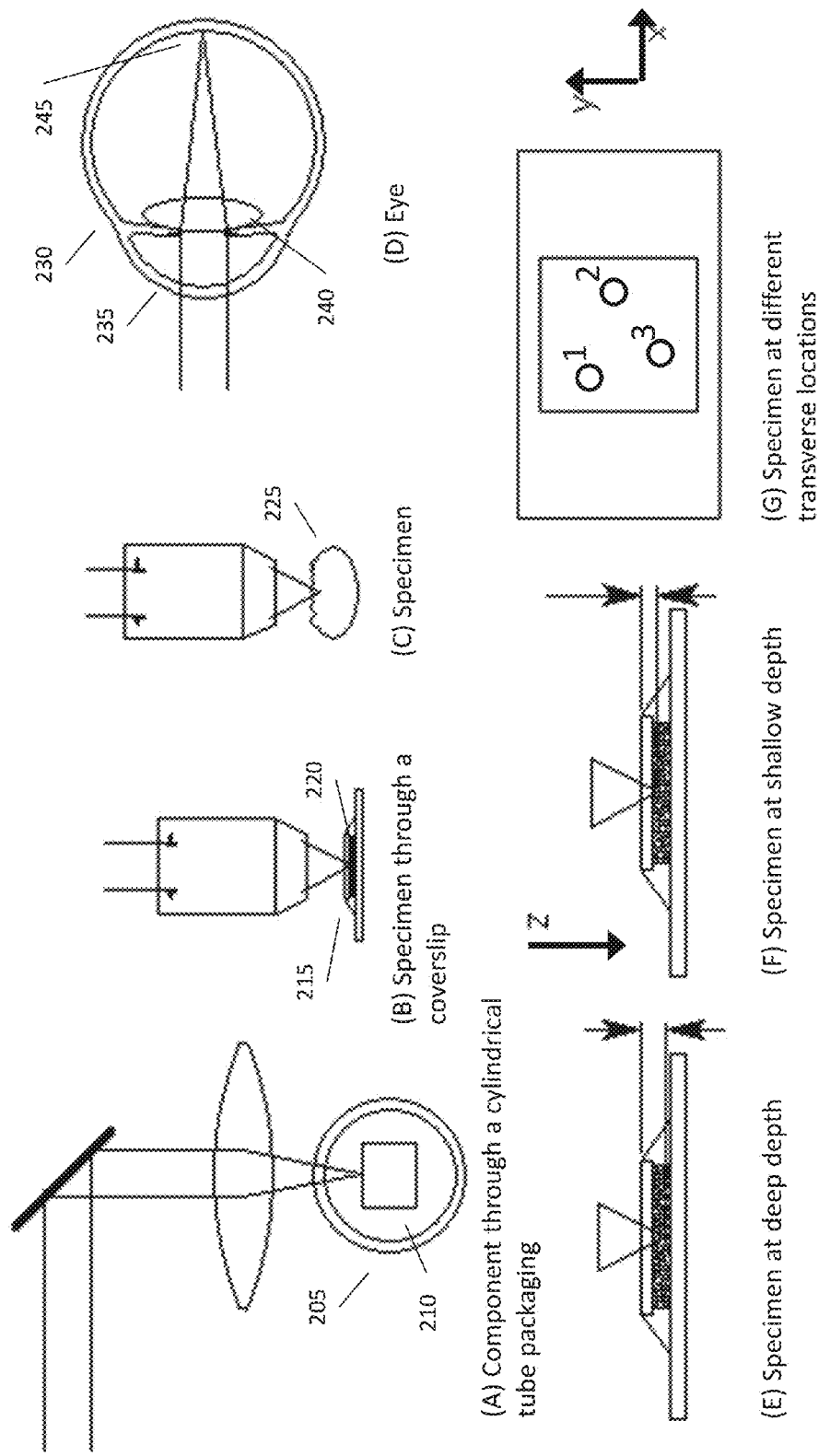
FIG. 2 is a collection of diagrams showing several of many possible sources of aberration that can be corrected using an embodiment of the present invention.

The source of the aberrations in an embodiment of the present invention can come from sources internal to the adaptive optics scanning system or external to the adaptive optics scanning system, as shown in FIG. 2. In one embodiment, the aberrations come from packaging 205 around a component 210 that is the sample, as shown in FIG. 2(A). The aberrations may originate from a glass window or coverslip 215 above the sample 220, as shown in FIG. 2(B). The aberrations may come from the sample or specimen itself 225, as shown in FIG. 2(C). The aberrations may come from a portion of the eye 230, including the cornea 235 or crystalline lens 240, as shown in FIG. 2(D). Focusing converging light through a surface with index of refraction mismatch, such as an interface between an emersion fluid, glass coverslip, or the sample itself, introduces spherical aberration. Inhomogeneity of the sample may introduce other aberrations. Thus, aberrations may change with depth, as illustrated in FIGS. 2(E-F) or with lateral position, as illustrated in FIG. 2(G). Aberrations cause distortion to the wavefront. One embodiment of the present invention uses the adaptive optics element(s) to compensate for aberrations in the sample. One embodiment of the present invention uses the adaptive optics element(s) to compensate for aberrations from a sample holder, which could be packaging, a coverslip, a window, a tube, a container, or any other material, object, fluid, or surface in contact with or in between the sample and the imaging system. The imaging system itself may have residual system aberration. One embodiment of the present invention uses the adaptive optics element to compensate for residual aberrations within the imaging system.

General Description

Figure 7:
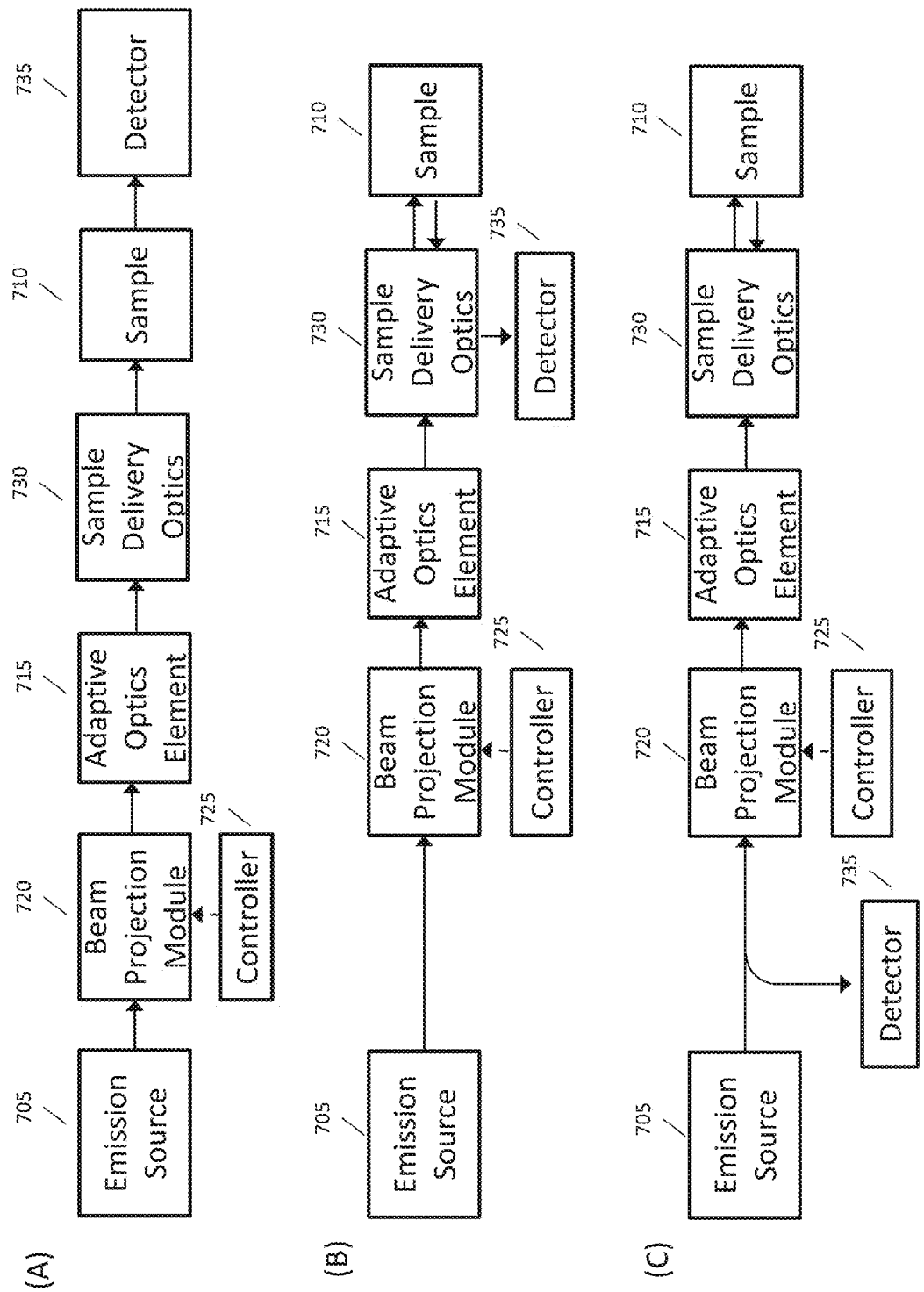
FIG. 7 is a collection of block diagrams showing possible subsystem layouts of an embodiment of the present invention in which the detector is located in different positions.

An embodiment of the present invention is an adaptive optics scanning system. A schematic diagram of an embodiment of the present invention is shown in FIG. 7. One embodiment of the present invention comprises an emission source 705 for generating light, the light being directed through the adaptive optics scanning system to a sample 710, one or more adaptive optics element(s) 715, the adaptive optics element(s) 715 affecting the wavefront, affecting the intensity, or affecting both the wavefront and intensity of the light, a beam projection module 720, the beam projection module 720 operating with four or more axes of motion and controlling an angle and position of the light to preferentially interface the adaptive optics element 715 by creating or accommodating a beam pivot point at or near the adaptive optics element(s) while scanning the light across the sample 710, a controller 725 for controlling motion trajectories of the axes in the beam projection module 720, sample delivery optics 730, the sample delivery optics 730 appropriately conditioning and directing the light to the sample 710, one or more detector(s) 735, the detector(s) 735 measuring light from the sample 710.

FIG. 7(A) shows an example embodiment in which the detector 735 is located after, or is separate from the sample delivery optics 730. One example of an embodiment in which the detector 735 is located after the sample delivery optics 730 would be a multiphoton imaging system in which the detector 735 receives light from the sample 710 directly, as is sometimes used when imaging thin samples or when detectors are arranged around the sample, but do not share an optical path with the sample delivery optics 730. The positioning of the detector 735 in FIG. 7(A) after the sample 710 only indicates the path of the light and does not indicate where the detector 735 is spatially located relative to the sample 710 and sample delivery optics 730 in practice. Other embodiments and imaging modalities can also use a configuration where the detector 735 does not share an optical path with the sample delivery optics 730. FIG. 7(B) shows an example embodiment in which the detector 735 receives light from at least a portion of the sample delivery optics 730. An example embodiment in which the detector 735 receives light from at least a portion of the sample delivery optics 730 is multiphoton imaging in which the light is collected through the microscope objective, patient interface optics, scan lens, or other sample delivery optics 730. FIG. 7(C) shows an example embodiment in which the detector 735 receives light from the beam projection module 720, possibly with additional components between the beam projection module 720 and detector 735. Example embodiments in which the detector 735 receives light from the beam projection module could be certain configurations of OCT, confocal imaging, profiling, or spectroscopy. Other positions of the detector 735 that are not shown are possible. The detector 735 can be located to receive or pick off light anywhere along the optical path, or can be located separate from the optical light delivery system.

As shown in FIG. 7, an embodiment of the present invention includes an emission source 705. The type of emission source used in the adaptive optics scanning system is selected to be compatible with the scanning application. Depending on the imaging modality, the emission source 705 can generate light with a diode, a laser, a pulsed laser, a tunable laser, a wavelength swept laser, a femtosecond laser, a fiber laser, a vertical-cavity surface-emitting laser (VCSEL), a wavelength tunable VCSEL, a plasma light source, a halogen lamp, a mercury lamp, an incandescent lamp, or a supercontinuum source. Other emission sources 705 are possible and included in an embodiment of the present invention.

Figure 8:
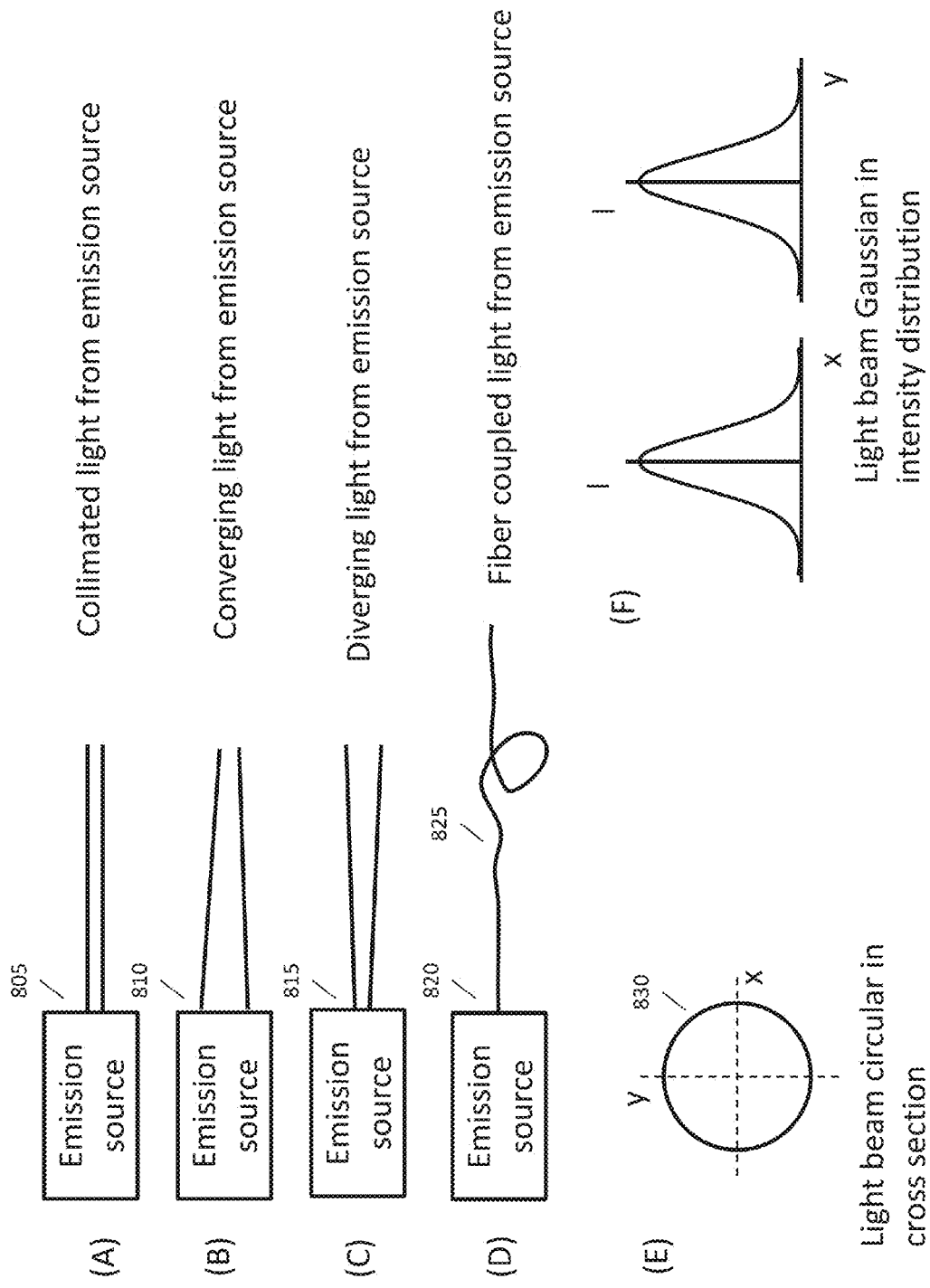
FIG. 8 is a collection of diagrams showing possible characteristics of the emission source that is used in an embodiment of the present invention.

The requirements on the light delivery from the emission source 705 depend on the application. Possible emission source characteristics are shown in FIG. 8. For example, a multi-photon imaging system may preferentially use a collimated beam from the emission source, while a confocal imaging or OCT system may preferentially use light delivered from a single mode or multi mode fiber. The present invention includes embodiments where the emission source includes optics for collimating light from a point source or small area emitter. In many cases, light from the emission source is collimated. Collimated or predominately collimated light is emitted from a titanium sapphire laser, among other light sources. An emission source 805 emitting collimated light is shown in FIG. 8(A). In one embodiment of the present invention, light from the emission source 805 is collimated. Light emitted from a point source that passes through a lens exiting the emission source may form a converging beam. In another embodiment of the present invention, the light from the emission source 810 is converging, as shown in FIG. 8(B). Light from a point source or small area emitter may form a diverging beam, as shown in FIG. 8(C). In one embodiment of the present invention, the light from the emission source 815 is diverging. For many applications, such as OCT and confocal imaging, it is desirable that the light be delivered with a fiber optic cable, as shown in FIG. 8(D). In one embodiment of the present invention the light from the emission source 820 is fiber coupled. Further, it is sometimes desired that the fiber optic cable 825 be single mode, as is the case for OCT and some implementations of confocal imaging. In one embodiment of the present invention the light from the emission source is fiber coupled into a single mode fiber. Light from the emission source can have very many shapes and light intensity distributions, all of which are included in an embodiment of the present invention. It is common that light from a laser or point source has a beam cross section 830 that is predominately circular, as shown in FIG. 8(E). In one embodiment of the present invention includes the light from the emission source is a beam with a cross section 830 that is predominately circular. Light from a laser source and other sources is often generally Gaussian in light distribution, as shown in FIG. 8(F). In one embodiment of the present invention the light from the emission source is a beam that is predominately Gaussian in intensity distribution. Different applications require different performance specifications for the emission source. An embodiment of the present invention includes implementations where the emission source 705 generates light with broadband spectral content and emits over a range of wavelengths (greater than approximately 2 nm). Applications that often use a broadband light source include OCT, multiphoton microscopy, confocal microscopy, fluorescent microscopy (using arc lamps, incandescent lamps, or LEDs), certain spectroscopy implementations, and others. Broadband light sources include swept light sources or light sources that emit continuous or pulsed broadband emission. An embodiment of the present invention includes implementations where the emission source 705 generates light with narrowband spectral content and emits over a narrow range of wavelengths (less than approximately 2 nm). Applications that often use a narrow band light source are confocal and fluorescent imaging (using laser light sources), certain types of profilometry, certain types of spectroscopy, and others.

Figure 3:
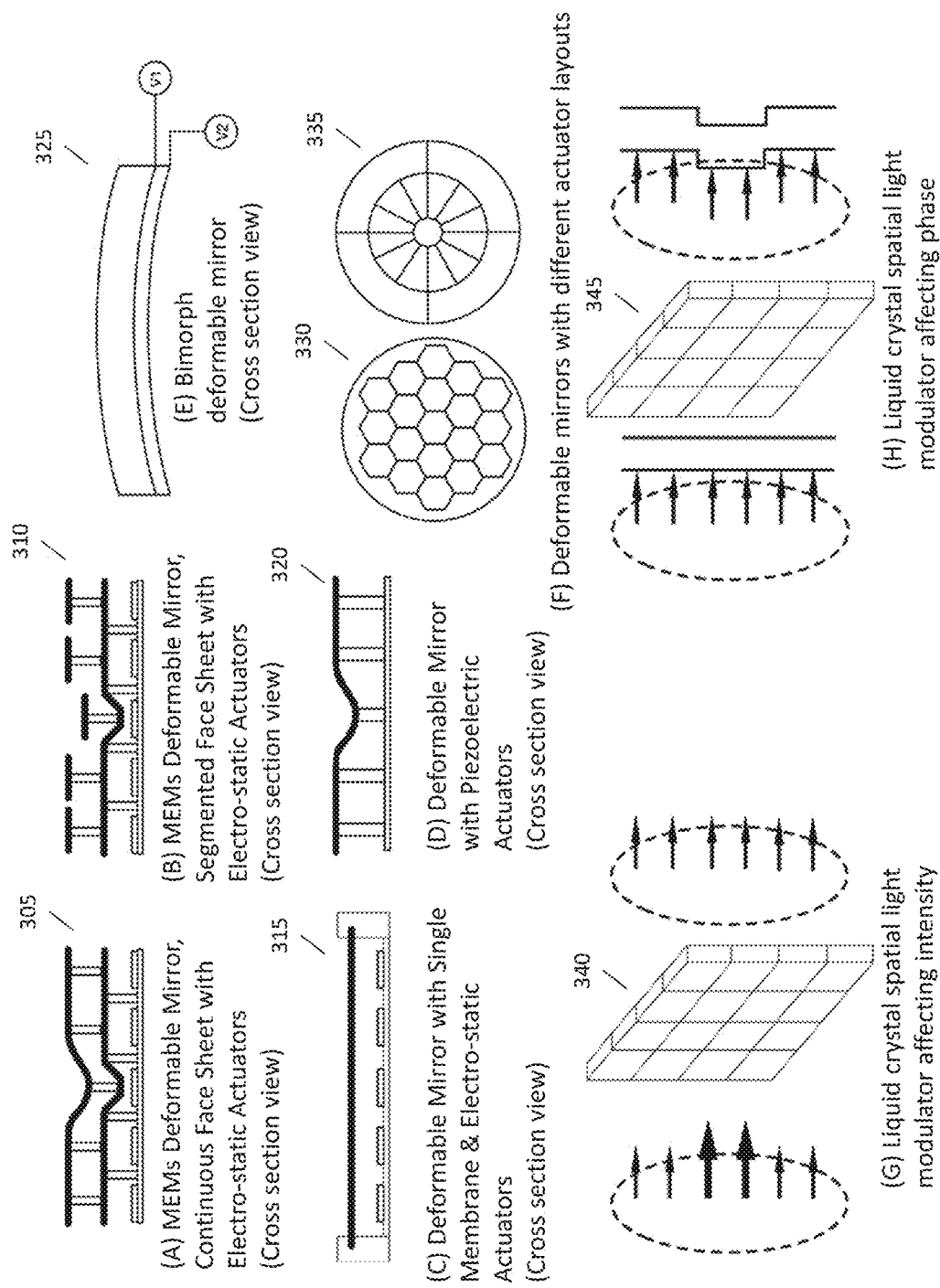
FIG. 3 is a collection of diagrams showing several of many possible adaptive optics technologies that can be used in an embodiment of in the present invention.
Figure 4:
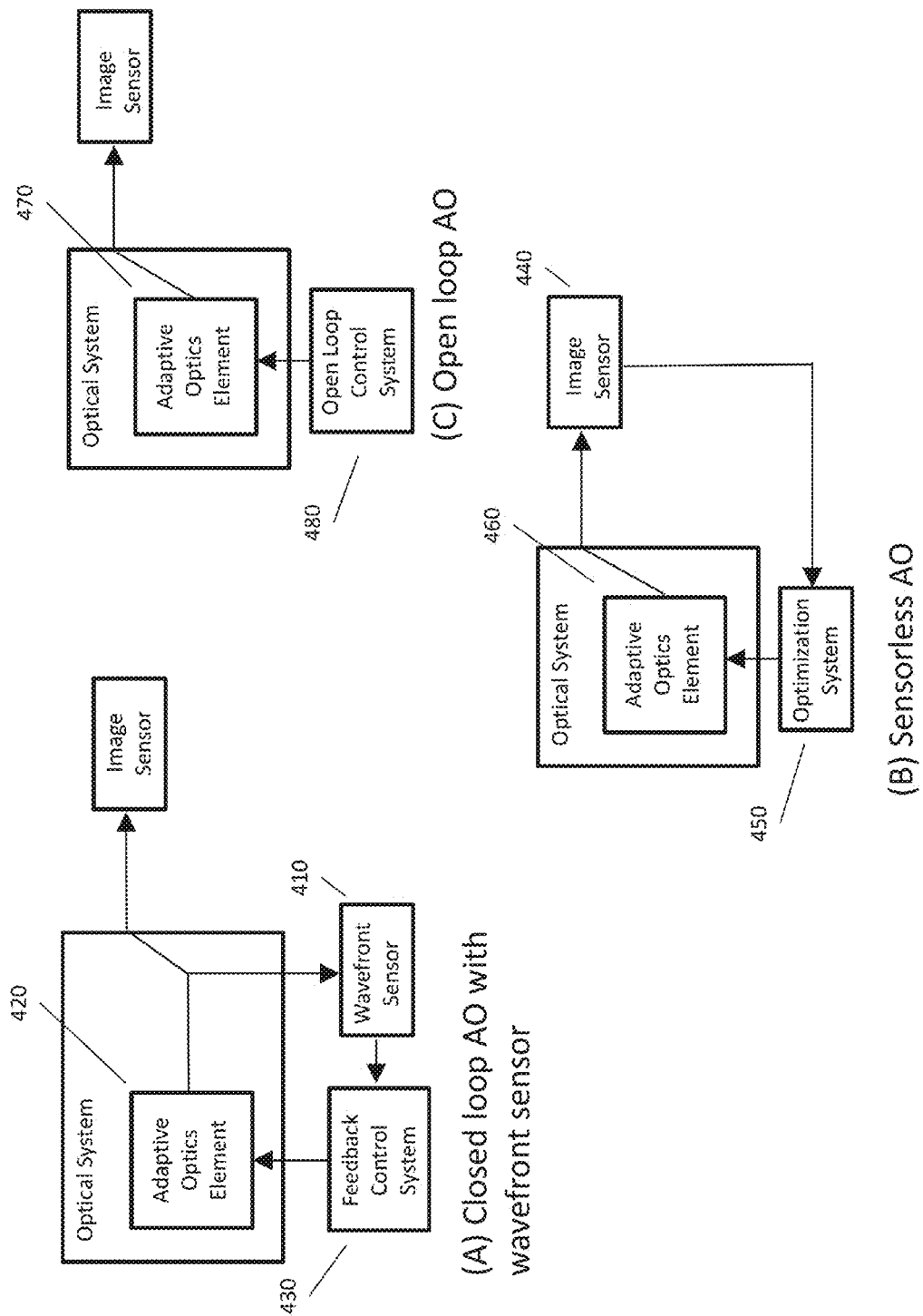
FIG. 4 is a collection of block diagrams showing adaptive optics control methods.

An embodiment of the present invention includes an adaptive optics element, also equivalently referred to as a wavefront corrector. There are many possible adaptive optics elements that can be used in an embodiment of the present invention, a subset of which are shown in FIG. 3. An embodiment of the present invention may use an adaptive optics element that is a deformable mirror 305, 310, 315, 320, 325, 330, and 335, a liquid crystal spatial light modulator 340 and 345, a liquid crystal device 340 and 345, a deformable mirror with continuous facesheet 305, 315, 320, 325, 330, 335, a segmented deformable mirror 310, a spatial light modulator 340 and 345, or other active and multi actuator or channel optical element that can affect the wavefront, affect the intensity, or affect both the wavefront and intensity of the light. The arrangement of the actuators in the adaptive optics element can vary depending on the design of the adaptive optics element. Common actuator layouts are grid patterns, honey-comb patterns, concentric circles, radially aligned actuators, circle or arc segment actuator layouts, and others. In one embodiment of the present invention, the adaptive optics element(s) 715 is a deformable mirror. In one embodiment of the present invention, the adaptive optics element(s) 715 is a liquid crystal spatial light modulator.

Figure 6:
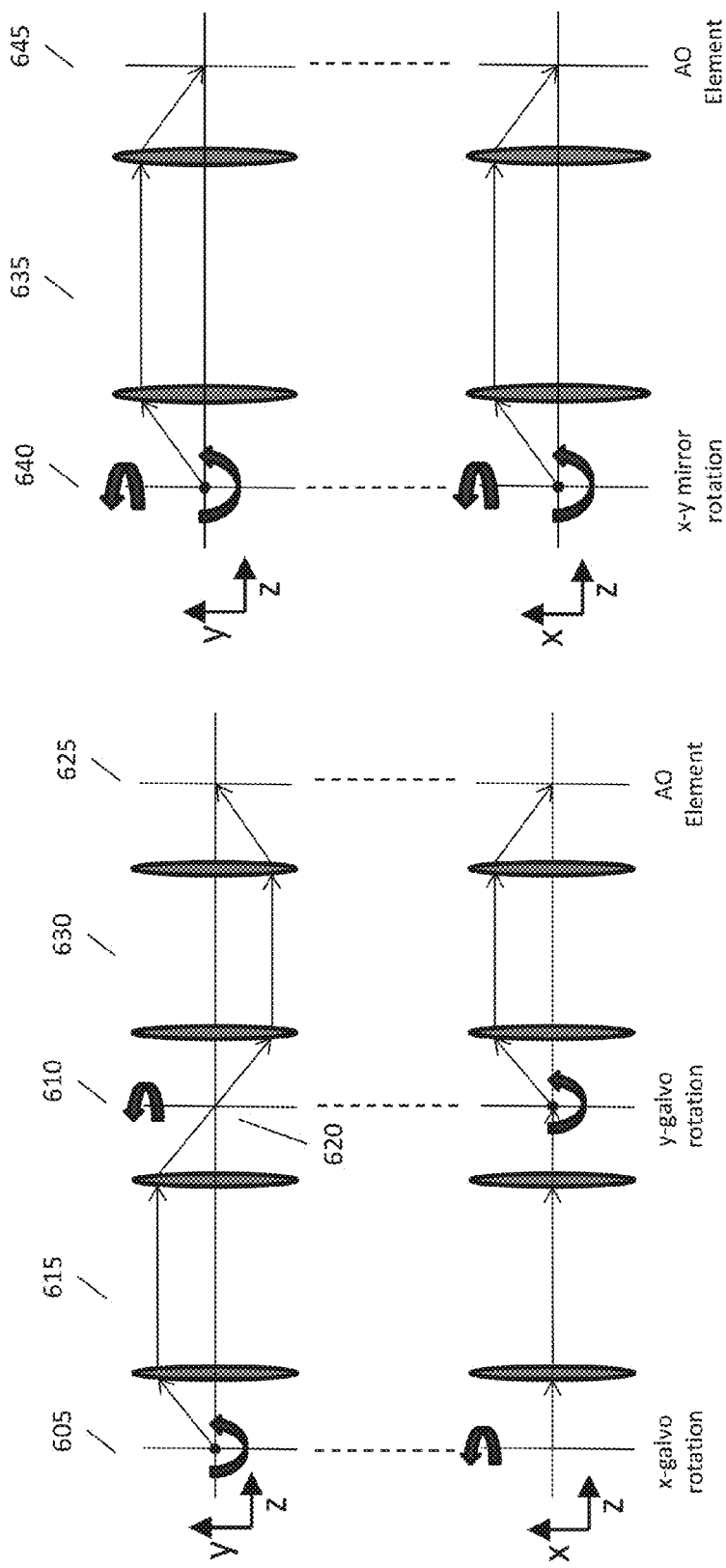
FIG. 6 is a collection of diagrams showing pupil relay systems with two separate single-axis scan mirrors or a single two-axes scan mirror.
Figure 9:
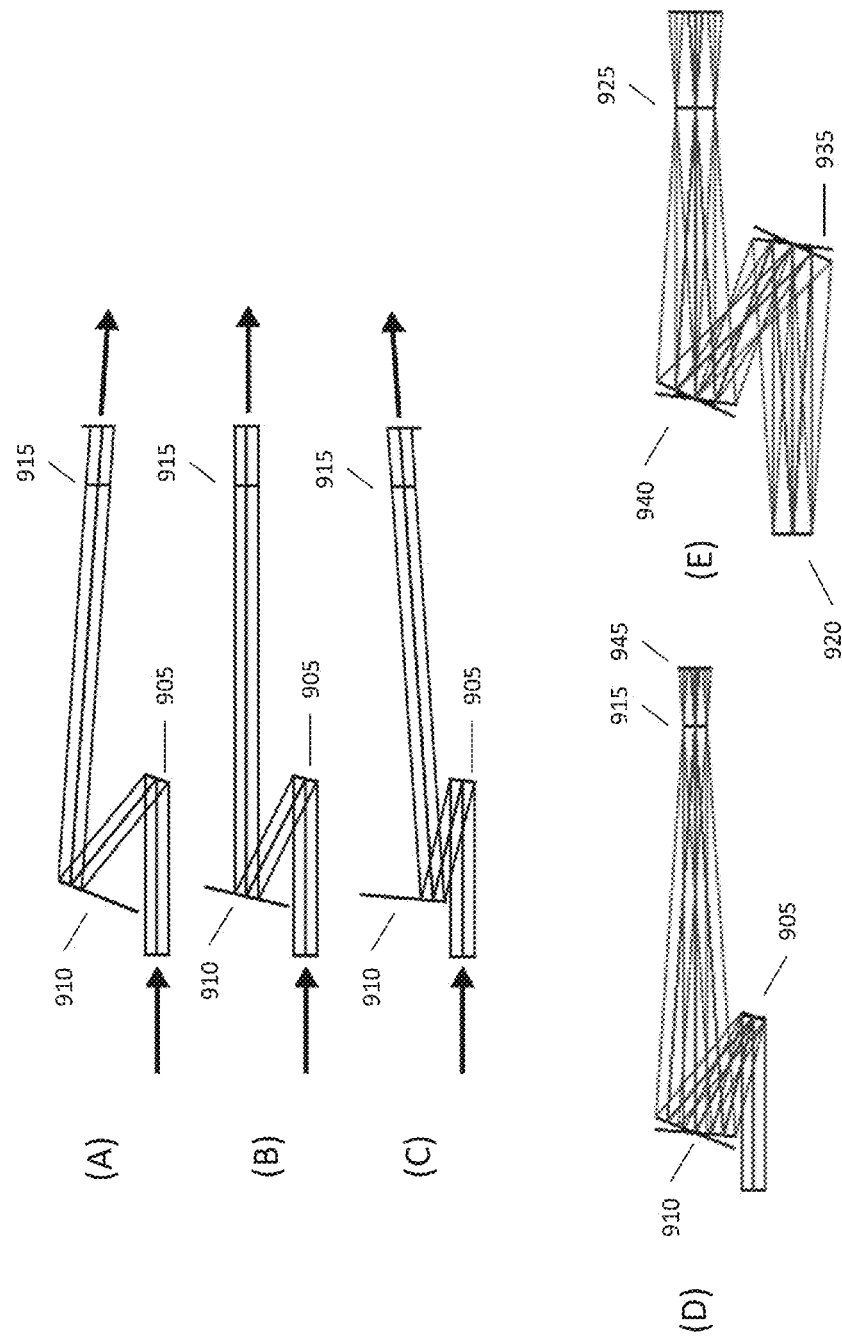
FIG. 9 is a set of diagrams showing how rotating mirrors can relay or control the position of a plane of stationary beam intensity, as desired for an embodiment of the present invention.
Figure 10:
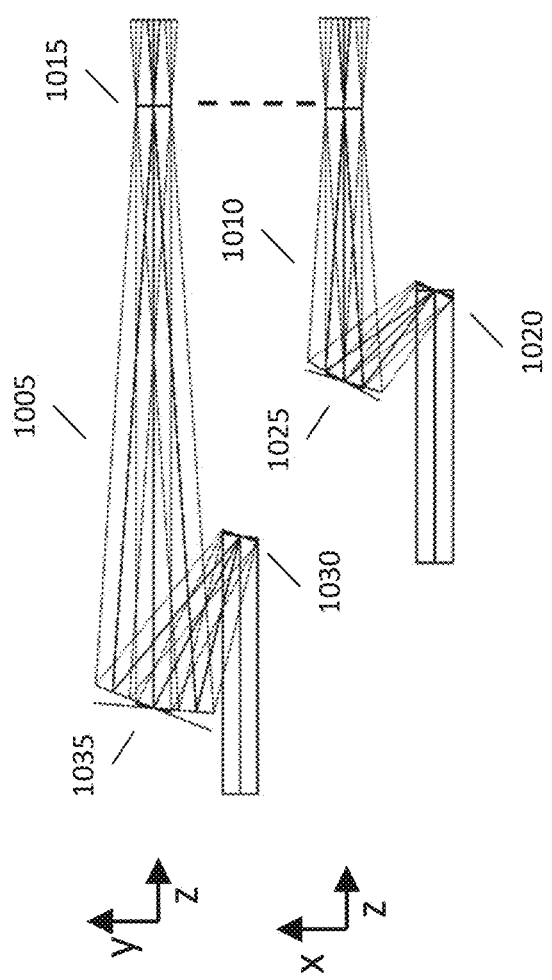
FIG. 10 is a diagram showing how two pairs of rotating mirrors can be aligned to relay or control the position of a plane of stationary beam intensity in two directions.
Figure 11:
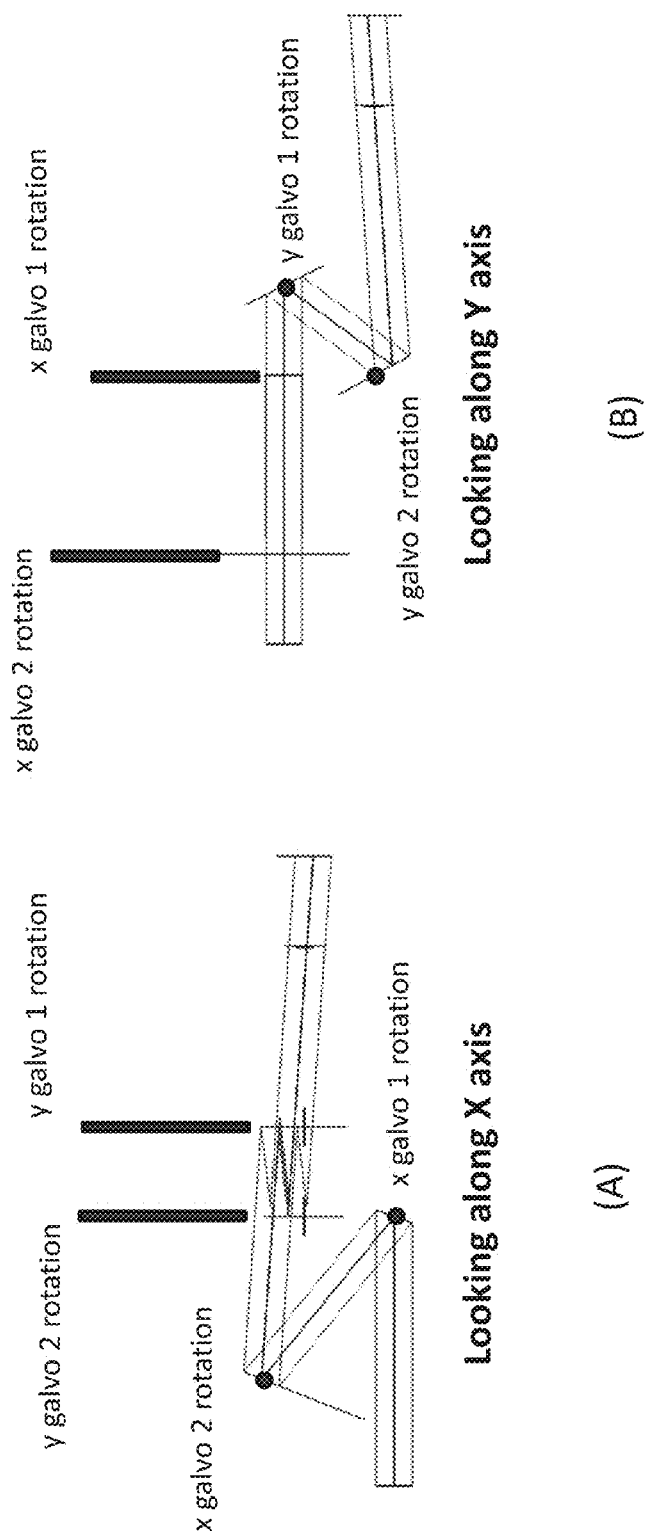
FIG. 11 is a pair of diagrams showing views of a two directional beam steering system that can relay or control the position of a plane of stationary beam intensity, as viewed from the x and y axis.

Many adaptive optics systems use pupil relays as shown in FIG. 5 to properly manage the requirements of beam pivot locations relative to scanner locations in the optical system. A traditional pupil relay performs a true relay of the pupil field and is used as the optical linkage between steering mirrors, the adaptive optics element, and the sample delivery optics or the sample itself in most existing adaptive optics systems. The preferred embodiment of the present invention uses a different approach. Because the beam diameters in laser based imaging systems are on the order of 0.5 mm to several cm and the beam quality is generally quite good, the divergence of the beam and associated changes in wavefront and intensity distribution over the path lengths of the instrument are negligible. Indeed, many existing two-photon microscopes are built using a commercially available laser source (e.g., Coherent Chameleon®) mated to a commercially available two photon microscope (e.g. Prairie Technologies Ultima®) in such a way that the collimated beam emerging from the laser source and entering the microscope traverses a distance that differs from installation to installation based on what is convenient to the layout and space available to the lab or site of installation. The beam maintains quality and is predominately unchanged over the cm to meters of collimated propagation so that careful control of distances and planes is not necessary. In other words, the high quality laser beam propagates with an essentially stationary (unchanging) intensity and wavefront over microscope installation scale (cm to several meters) distances. With this in mind, it is helpful to revisit the standard AO configuration in which a pupil relay (afocal 4f telescope) is used to image the pupil plane of one steering mirror 605 to the pupil plane of another steering mirror 610, as shown in FIG. 6. A first effect of the pupil relay (afocal 4f telescope) 615 is to create a virtual pivot point at the mirror plane 620 so that the beam is always directed towards the center of the mirror for all incoming and outgoing beam angles. A second effect of the pupil relay is to sample and relay the optical field from one pupil plane 605 at a first steering mirror to another pupil plane 610 at a second steering mirror. In this way, the optical wavefront and intensity distribution are relayed from the first pupil plane 605 to the second pupil plane 610, even if the wavefront is not flat and the intensity distribution complex. For a scanning adaptive optics system, the first effect of creating the virtual pivot point is necessary, while the second effect of relaying the wavefront and intensity distribution is not necessarily required. If the beam is sufficiently large in diameter, predominately collimated, predominately of planar wavefront, and predominately of Gaussian intensity distribution, the beam will propagate between flat mirror reflections essentially unchanged. It is therefore not necessary to formally relay the pupil planes, but rather it is desirable to simply create virtual pivot points of the beam. The same reasoning holds when relaying from the second pupil plane 610 to the plane of the adaptive optics element 625, as is commonly performed with a second pupil relay 630. Consider a beam with an intensity distribution and wavefront that nominally remains predominately constant over cm to meters of propagation distance, such as the beams described. FIG. 9 shows that it is possible to use a method of creating a virtual pivot point with a stationary position, but a variable beam angle using a pair of rotating mirrors instead of lenses or concave mirrors as would be used in a traditional 4f design. In the neutral (zero) position as shown in FIG. 9(B), the beam initially propagates from left to right, reflecting off a first steering mirror 905. The beam then propagates upwards and to the left, reflecting off a second steering mirror 910. The second steering mirror directs the beam to propagate towards the right, where it intersects a plane 915 at a particular location. By appropriately adjusting the steering mirror angles as shown in FIG. 9(A), the same optical configuration can create a downwards beam angle that intersects the plane 915 at the same location as in the neutral position shown in FIG. 9(B). Similarly, a different set of steering mirror angles, as shown in FIG. 9(C), generates an upwards beam angle that intersects the plane 915 at the same location. FIG. 9(D) superimposes the three configurations shown in FIGS. 9(A-C) and shows that proper adjustment of the steering mirror angles allows a plane 915 of predominately stationary beam intensity to be formed with adjustable beam angle around a pivot point. Setting proper angles on the mirrors allows intermediate beam angles to be generated that all rotate around the same pivot point. This optical construct can be used to satisfy the requirement of creating a virtual pivot point to be used as the linkage between the beam steering mechanisms and the adaptive optics element in an adaptive optics scanning system in place of the more traditional pupil relay (afocal 4f telescope), but has significant advantages of no off-axis aberration, no dispersion, and a compact size. FIG. 9(D) shows a beam entering from the left and a beam of stationary intensity position but variable angle being formed to the right of the beam steering mechanism in a plane 915. FIG. 9(E) shows that the same optical construct can also be used to accept light from a plane 920 of stationary beam intensity position, but variable beam angle and generate a second plane 925 of stationary beam intensity position, but variable beam angle to the right of the beam steering mechanism by using a first steering mirror 935 and second steering mirror 940 oriented at appropriate angles. Further, the flexibility of the arrangement allows arbitrary and programmable placement of the position and the angle of the output beam. For example, the plane 945 in FIG. 8(D) shows a changing beam position with changing beam angle. The beam position and beam angle are fully programmable within the working apertures of the mirrors and can be pre-programmed or recalculated on the fly to create arbitrary beam position and beam angle trajectories during the scan, which may or may not pivot around the same point. The two basic functionalities illustrated in FIGS. 9(D-E) can be used as building blocks for a compact scanning mechanism in an adaptive optics scanning system. Most beam scanning systems scan in two directions, X and Y, across the sample. FIG. 10 shows that it is possible to connect an X beam scanning mechanism 1005 consisting of two rotating mirrors with a Y beam scanning mechanism 1010, also consisting of two rotating mirrors. The two beam scanning mechanisms are oriented in orthogonal directions (rotated 90 degrees) and project to the same stationary point in a plane 1015. In this example, the second pair of rotating mirrors 1020 and 1025 fits between the stationary point in the plane 1015 and the first pair of rotating mirrors 1030 and 1035 in such a way that the output of the first rotating mirror pair becomes the input to the second rotating mirror pair. FIG. 11 shows an example configuration based on this principle that illustrates x and y scanning using four galvanometers (galvos) to actuate the steering mirrors. Other relative ordering and arrangement of the mirrors are possible. The collection of mirrors and actuators that generate the programmable position and angle of the beam is referred to as a beam projection module 720 in this patent application.

Figure 12:
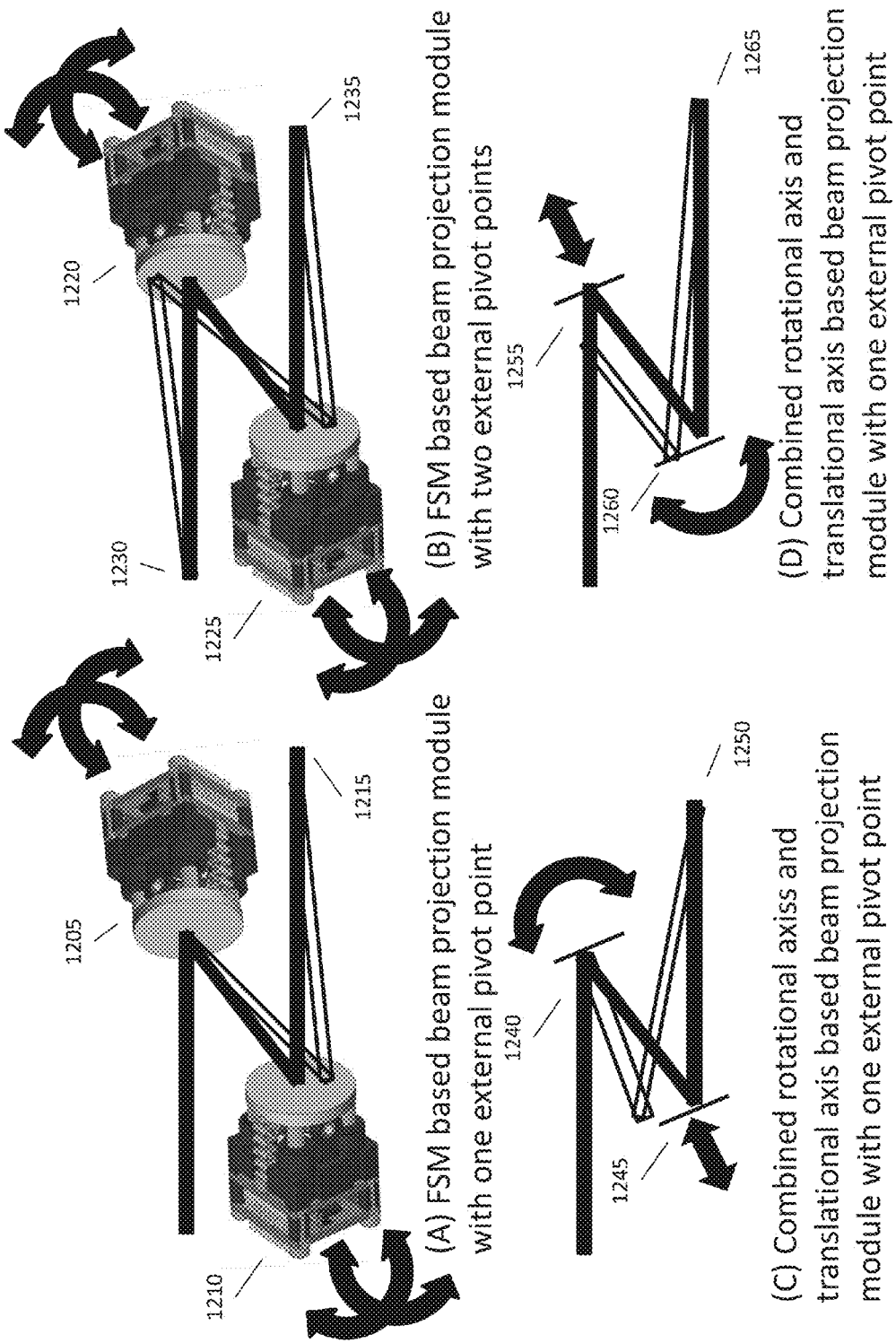
FIG. 12 is a collection of diagrams showing different possible implementations of systems that can relay or control the position of a plane of stationary beam intensity, including systems composed of fast steering mirrors (FSMs), rotational mirrors, and translational mirrors.

An embodiment of the present invention of an adaptive optics scanning system includes a beam projection module for generating a pivot location for the beam at an appropriate location in the optical system. The beam projection module has four or more axes of motion that affect mirrors to properly guide the beam. One embodiment of the present invention uses an arrangement where at least one axis of the beam projection module is rotational. As shown in FIG. 11, one embodiment of the present invention includes a beam projection module that comprises four galvanometer driven mirrors. The ordering of the galvos can be optimized to the specific imaging application. One embodiment of the present invention uses an optical layout in which the two x-axis galvos precede the y-axis galvos. In another embodiment, the two y-axis galvos precede the two x-axis galvos. In another embodiment the axis are split such that a first x and y galvo precede a second x and y galvo. Other mirror and actuator configurations are also possible. For example, FIG. 12(A) shows a beam projection module comprised of two fast steering mirrors (FSMs) 1205 and 1210 to project one external pivot point 1215. FIG. 12(B) shows a beam projection module comprised of two fast steering mirrors (FSMs) 1220 and 1225 that accepts light from an external beam pivot point 1230 and projects an external beam pivot point 1235. Combinations of an FSM and galvos are also possible. One embodiment of the present invention includes a beam projection module comprising at least one fast steering mirror (FSM). Another more specific embodiment of the present invention comprises a beam projection module that uses two fast steering mirrors, each fast steering mirror having two axes of rotation. Other two-axes, single mirror beam steering elements can also be used as described with the FSM, such as MEMS mirrors, gimbaled mirrors, piezo driven tip-tilt mirrors or other tip-tilt mirror mechanisms. In another embodiment, the beam projection module comprises at least one galvanometer driven mirror. Not all of the actuators and mirror motions have to be rotational. It is possible to combine rotational and translational actuators and mirror movements to accomplish the goal or projecting a beam to a programmable position and beam angle. FIG. 12(C) shows how a first rotational mirror 1240 can be combined with a second translational mirror 1245 to create a beam projection module that generates an external beam pivot 1250. The ordering of rotational to translational axis can differ. FIG. 12(D) shows how a first translational mirror 1255 can be combined with a second rotational mirror 1260 to create a beam projection module that generates an external beam pivot 1265. More generally, one embodiment of the present invention operates with at least one axis of the beam projection module being translational. Another embodiment of the present invention comprises a beam projection module that uses a combination of rotational and translational axes or degrees of freedom. Other beam steering devises are possible. One embodiment of the present invention operates with the beam projection module comprising at least one of the following list: steering mirror, acousto-optic deflector, rotating polygon, electro-optic beam deflector, electro-optic prism, thermo-optic prism, diffractive array, mechanically scanned mirror, mechanically scanned mirror driven by a motor, mechanically scanned mirror driven by a stepper motor, a mechanically scanned mirror driven by a galvanometer, a MEMS mirror, an acoustic-optic modulator, or a liquid crystal device.

The angles or positions of the mirror must be controlled to generate the desired beam projection output. Many actuators have associated feedback control systems such that a position command is used as an input to command the actuator and the control system acts to track the commanded position. For example, a galvo system may use a capacitive or optical encoder to measure the position of the galvo angle. The measured position is compared to a commanded position to generate a position error. The position error is processed by a feedback controller, for example a proportional-derivative-integral (PID) controller or full state feedback controller, to generate a corrective action to be applied to the actuator in the galvo. In this way, commands to the mirror are executed up to bandwidth, acceleration, and velocity limits of the actuator and controller. These localized feedback control systems manage the low level position control of the actuators. Other actuators respond well to open loop position commands, such as MEMS devices and piezo actuators. One embodiment of the present invention uses closed loop control for at least one axis in the beam projection model. Another embodiment of the present invention uses open loop control for at least one axis in the beam projection module. However, regardless of the localized actuator control scheme, the positions between the different actuators and mirrors in an embodiment of the present invention must be carefully coordinated to generate the desired beam steering effect.

Coordination between the different axes in the beam steering module is performed by a controller 725 for controlling the motion trajectories of the axes in the beam projection module. The controller generates position commands to the individual actuators to coordinate the motion. In the preferred embodiment, the coordination is performed by a processor or circuit that can execute code, logic, or instructions to generate the desired position commands. The processor can be a microprocessor, a microcontroller, a digital signal processor (DSP), field programmable gate array (FPGA), application specific integrated circuit (ASIC), or any other processor that can perform digital calculations. A digital processor is preferable because nonlinear calculations can be performed, there is adjustability and flexibility in calculation, and there is often spare processor capability already available in many imaging systems. However, analog circuits can also be used to perform the control. Depending on if the actuators for the mirrors in the beam projection module are controlled in an open loop or a closed loop (feedback) manner, the controller may also comprise the close loop controllers in addition to the processor that generates the motion trajectories for each of the axis in the beam projection module. In either case of open or closed loop actuator control methods, the controller generates motion trajectories and is for controlling the motion trajectories of the axes in the beam projection module. In the preferred embodiment of the present invention coordination between the degrees of freedom in the beam projection module is controlled through electronic signals to the actuators or active elements. In one embodiment, the actuators for any given scan axis are coupled such that the desired output command for each individual axis is determined by a single input parameter. In another embodiment of the present invention, coordination between the degrees of freedom in the beam projection module is controlled through a mechanical linkage. An imaging system generally scans a spot on the specimen and many scan trajectories are possible. One embodiment of the present invention uses the beam projection module 720 to scan the mirrors with trajectories that cause the light beam to trace a raster scan pattern 1705 on the sample 710.

An embodiment of the present invention includes optics for delivering the light to the sample 710, called sample delivery optics 730. Most samples require that an objective lens focus the light to or into the sample. One embodiment of the present invention includes sample delivery optics comprising a microscope objective. More generally, one embodiment of the present invention uses sample delivery optics that direct the light towards the sample in a converging beam with a numerical aperture (NA) to achieve a desired resolution in the sample. Other samples include their own optics or optical surfaces, such as the biological eye or a camera system, which have different requirements on the characteristics of the light delivery such that a collimated or nearly collimated beam is preferable for delivery of light to the sample. One embodiment of the present invention uses sample delivery optics that direct the light towards the sample in a predominately collimated beam with a pivot point located at or near a pupil plane within the sample such that optical properties of the sample focus the light at a desired imaging plane. More specifically, one embodiment of the present invention uses a predominately collimated beam directed into an eye, the pivot point of the beam being located at or near the pupil of the eye such that the light is focus at or near the retina 245 in the eye. The sample delivery optics are used for conditioning and directing the light to the sample, where conditioning refers to generating the appropriate collimation, convergence, or divergence of the beam, generating the appropriate beam diameter, generating the appropriate numerical aperture, generating an appropriate intensity profile, generating an appropriate spot size, generating an appropriate spot shape, generating an appropriate wavefront, or any other way of affecting a light beam to preferentially interact with the sample.

An embodiment of the present invention includes a detector 735 for detecting light from the sample 710. In one embodiment of the present invention, the detector 735 is a line scan camera for performing spectral/Fourier domain OCT. In another embodiment of the present invention, the detector 735 comprises a high speed photodiode to implement unbalanced detection or two high speed photodiodes to implement balanced detection for performing swept source/Fourier domain OCT. In another embodiment of the present invention, the detector 735 comprises a photomultiplier tube (PMT) or avalanche photo diode. More specifically, one embodiment of the present invention uses a detector that comprises a photomultiplier tube (PMT) or avalanche photo diode for performing two-photon, multi-photon, or second harmonic imaging. Another embodiment of the present invention uses a detector 735 comprising a photomultiplier tube (PMT), photo diode, or avalanche photo diode for performing confocal imaging. In yet another embodiment of the present invention, the detector is a spectrometer for resolving a spectral content of light from the sample. Another embodiment of the present invention uses a detector that records information in the light from the sample with a photo-chemical reaction, as is used in film. Another embodiment of the present invention uses a detector that records information in the light from the sample with a thermal sensor. In optical tweezer systems, the object under manipulation is often monitored with a camera, for example a charge-coupled device (CCD) or Complementary metal-oxide-semiconductor (CMOS) array. Applying an optical force to the object under manipulation and monitoring the response of the object with a camera can indicate the strength of the optical trapping force. Measurement of the optical trapping force depends on aberrations in the system and an adaptive optics element can be optimized to maximize trapping force. In one embodiment of the present invention, the detector 735 is a camera. In another embodiment of the present invention, the detector 735 is a wavefront sensor. In another embodiment of the present invention, the detector 735 measures an intensity of light from the sample. The detector 735 can be located in different locations along the optical path, consistent with the application, or can be located separate from the optical system delivering light to the sample.

Multiphoton Microscopy Embodiment

Figure 13:
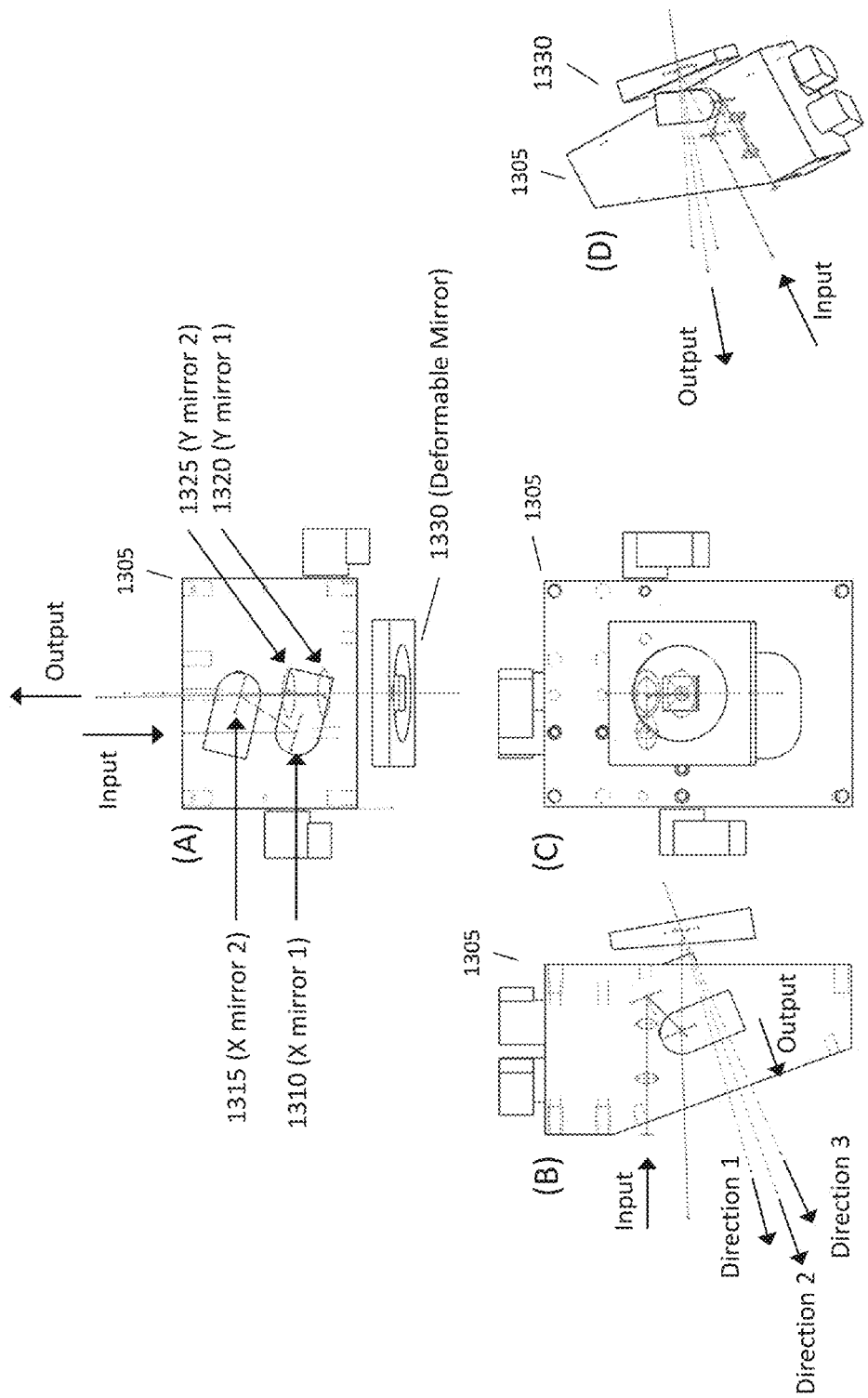
FIG. 13 is a collection of diagrams showing an example implementation of the beam projection module of the current invention with the beam path shown and with input and output beams indicated.
Figure 14:
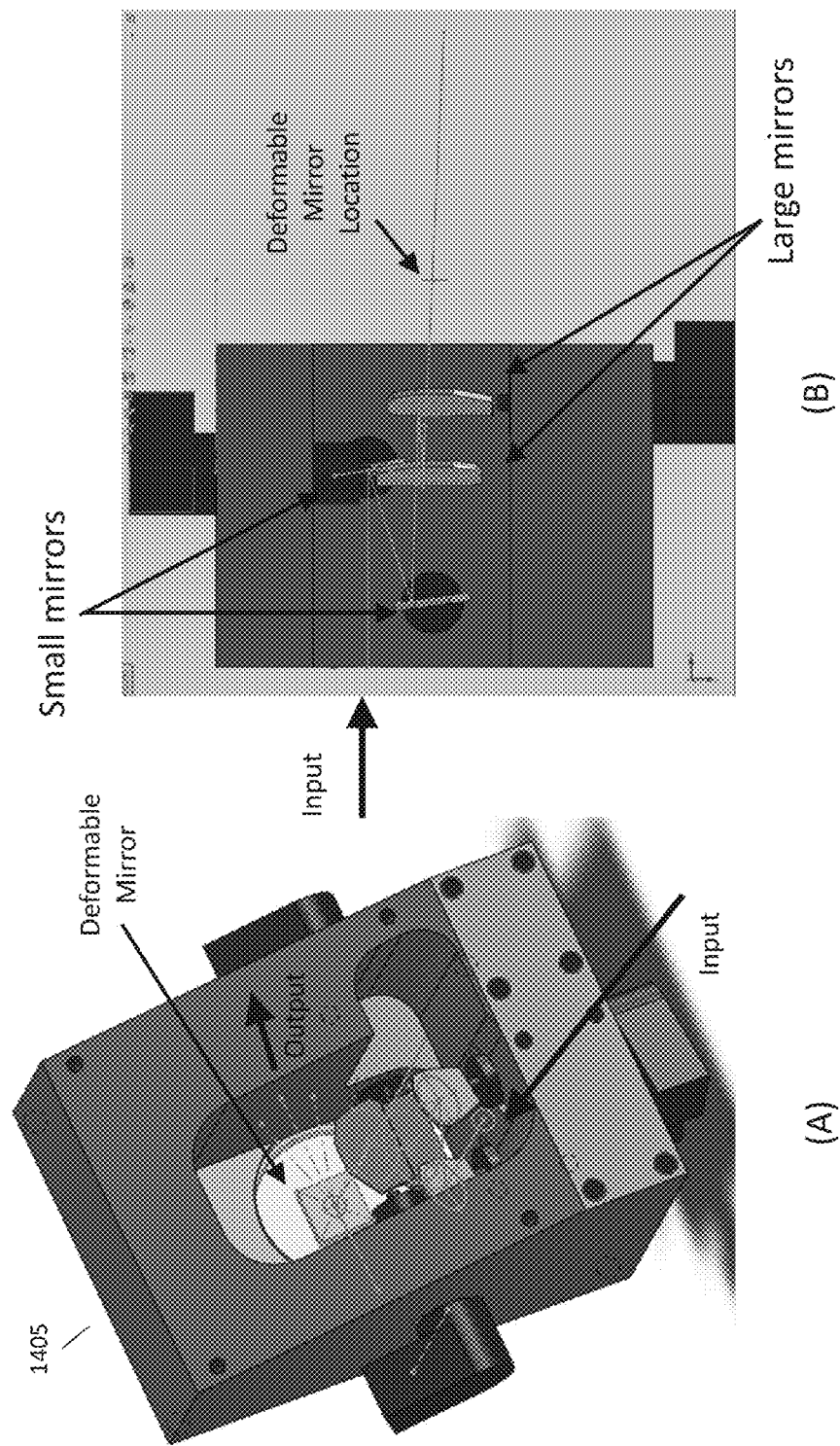
FIG. 14 is a set of solid model renderings that show the elements and beam paths in an example implementation of the beam projection module of an embodiment of the present invention.
Figure 15:
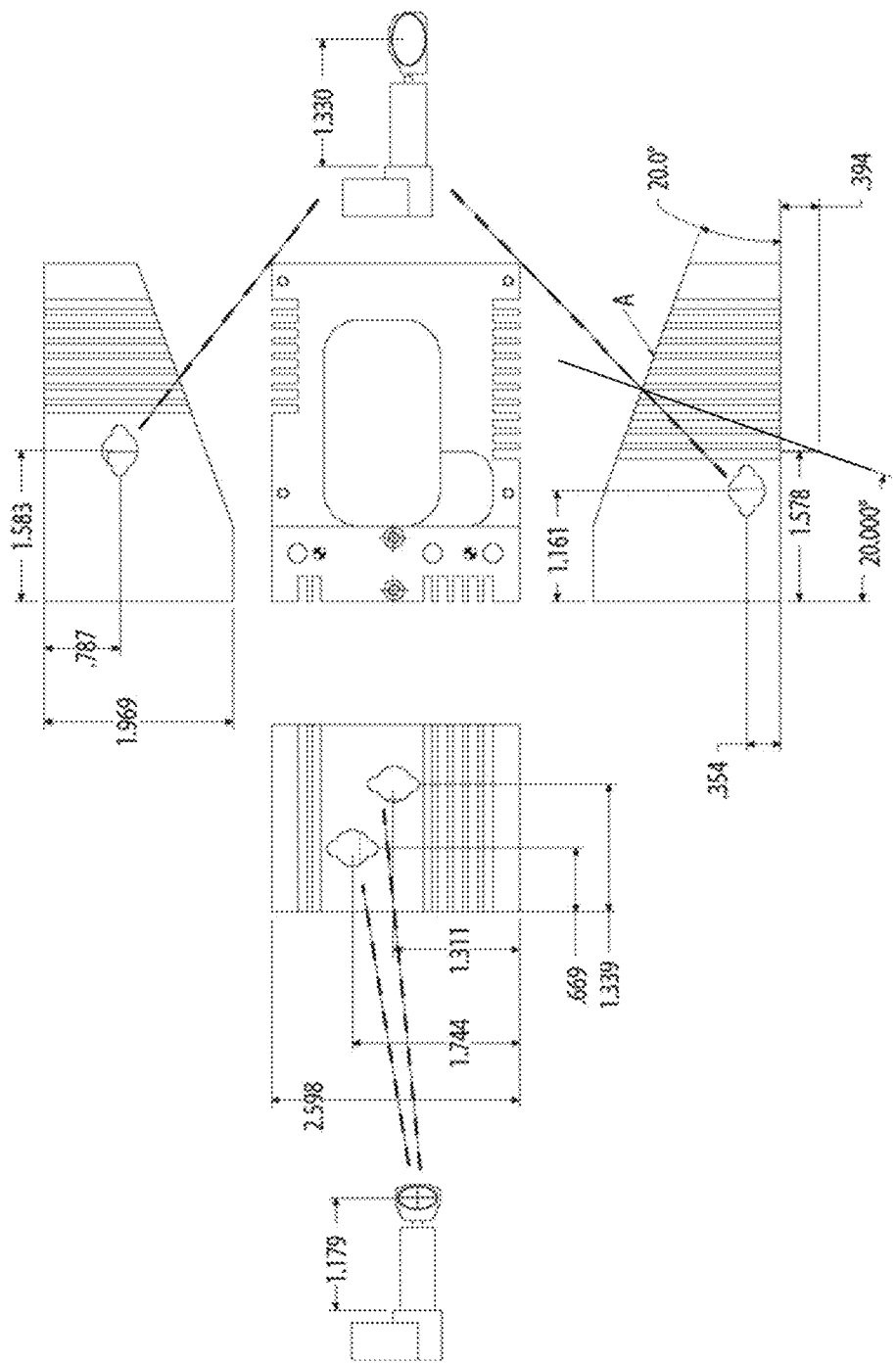
FIG. 15 is a collection of drawings indicating placement and orientation of beam steering mirrors in the beam projection module of an embodiment of the present invention.
Figure 16:
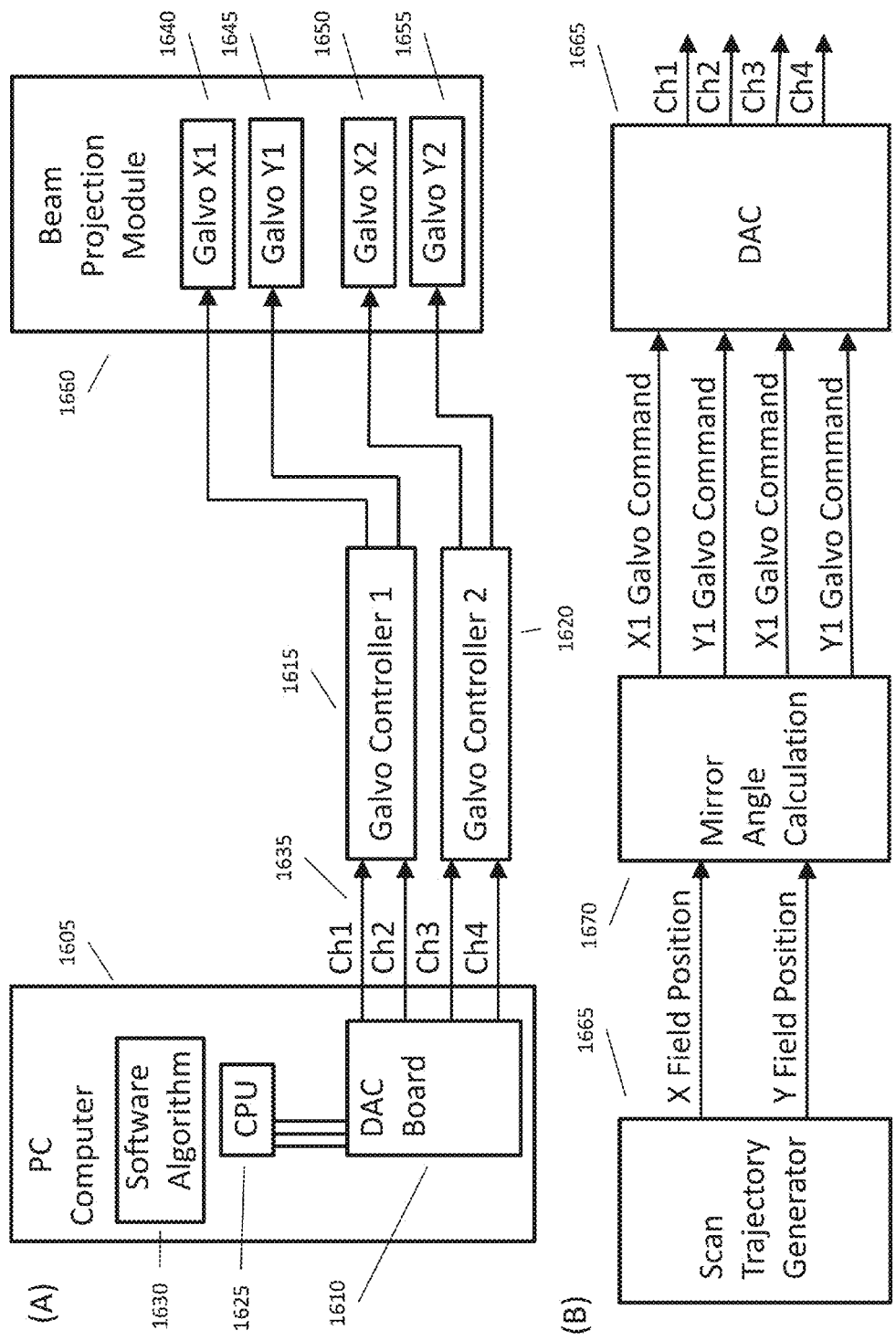
FIG. 16 is a set of block diagrams showing a controller of an embodiment of the present invention.
Figure 20:
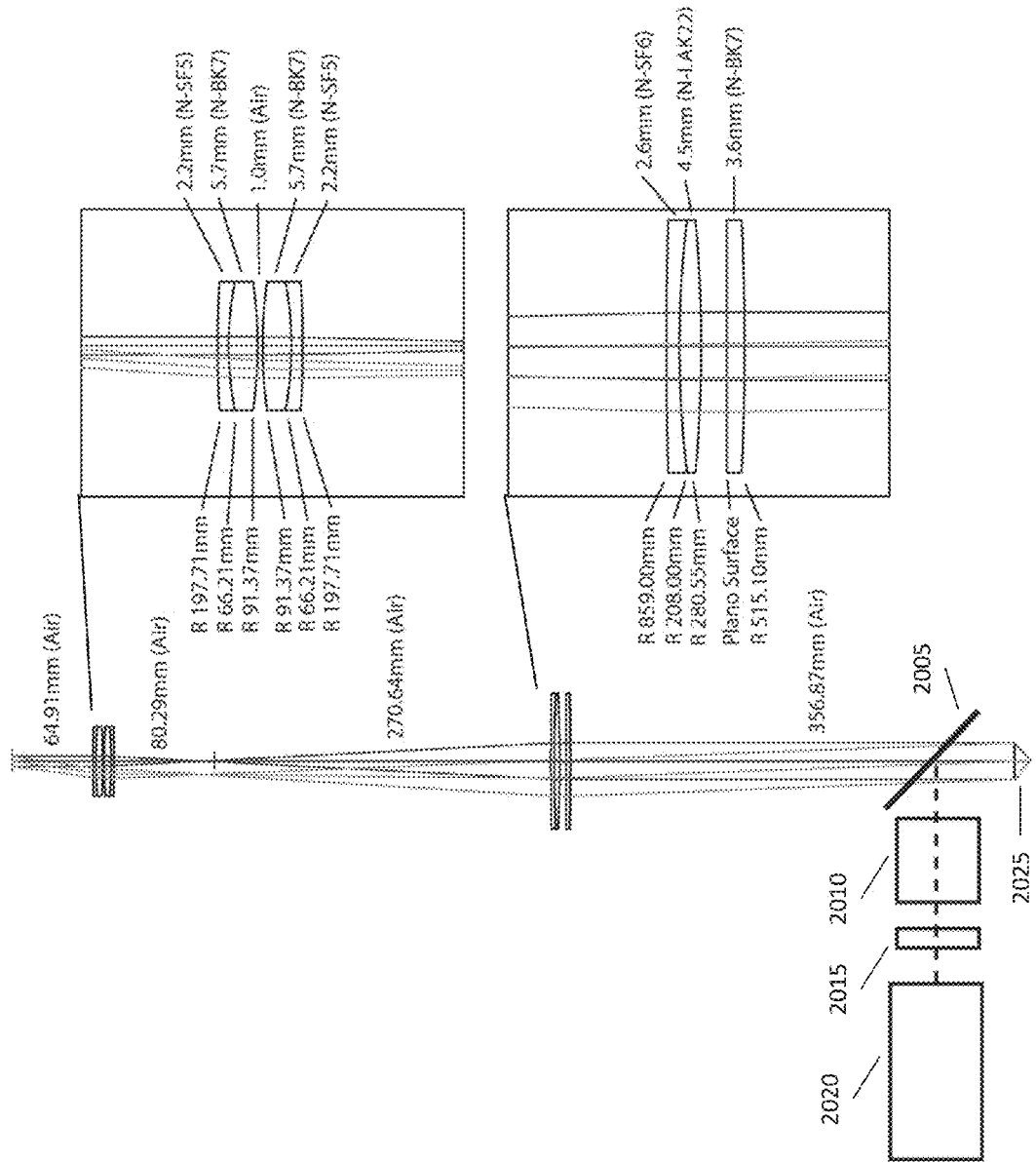
FIG. 20 is a collection of drawings showing lens prescriptions for a prototype embodiment of the present invention.
Figure 21:
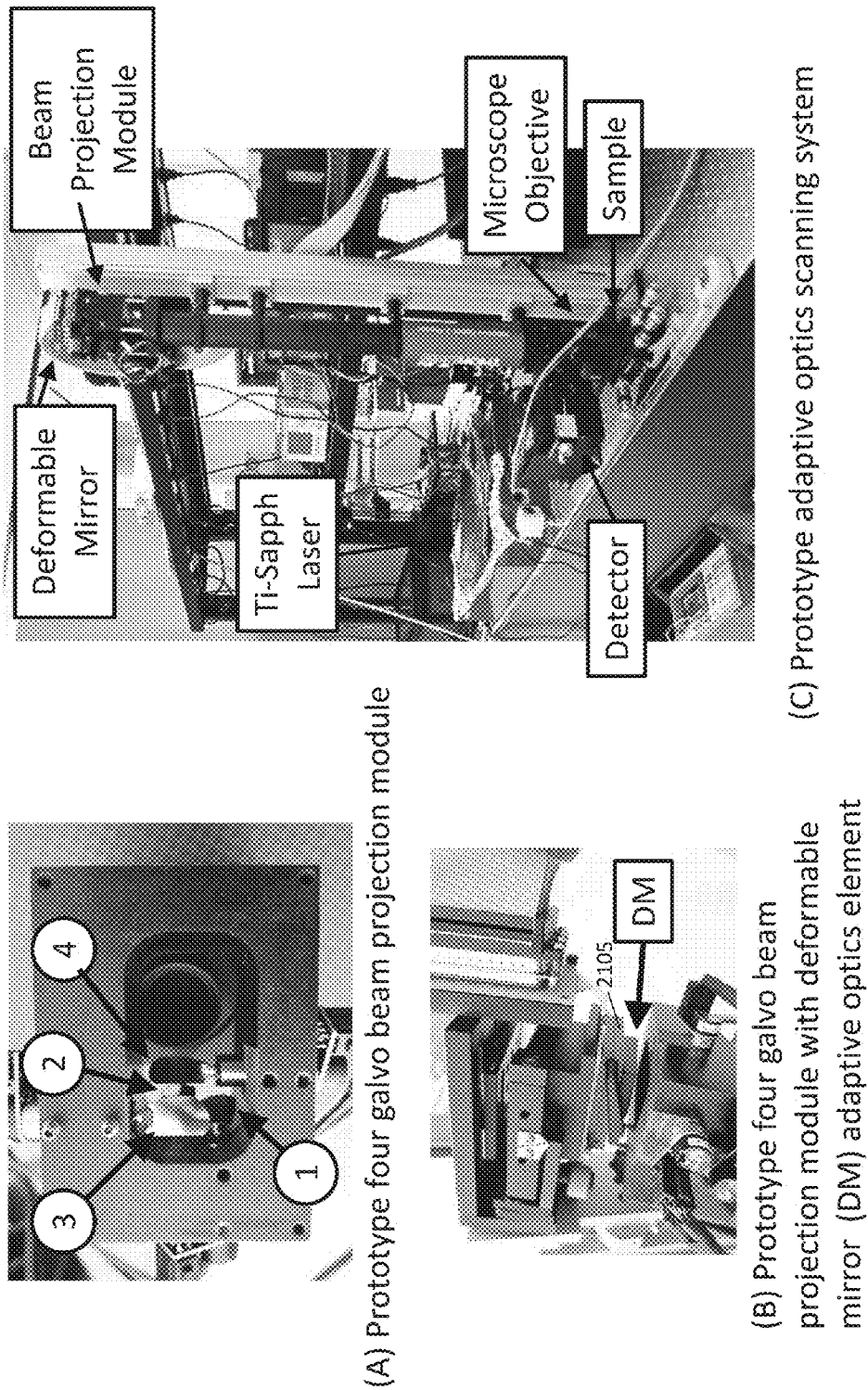
FIG. 21 is collection of photographs showing a prototype of an embodiment of the present invention.
Figure 22:
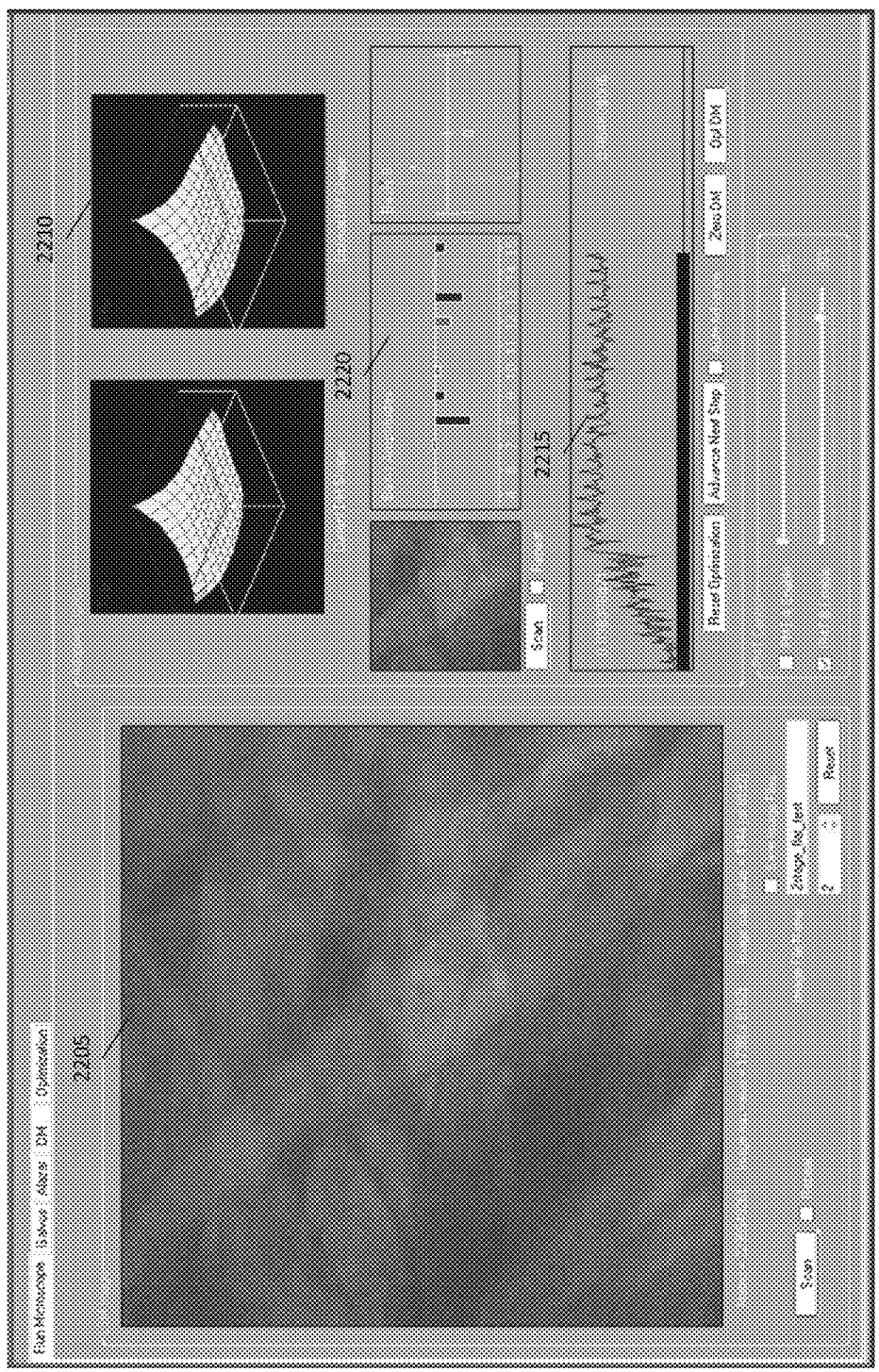
FIG. 22 is a screen capture of a software program operating an embodiment of the current invention showing optimization of the adaptive optics element.
Figure 23:
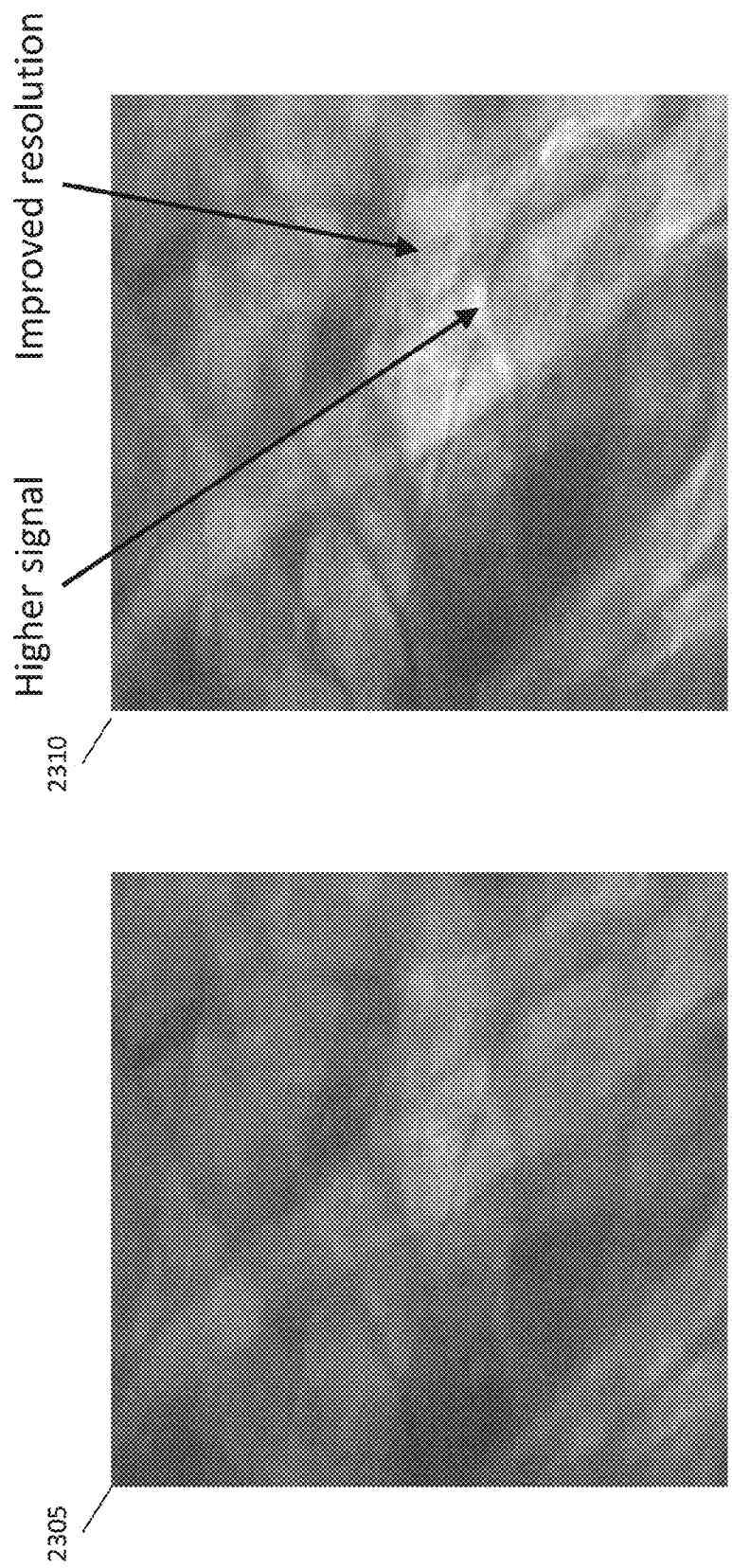
FIG. 23 is a pair of images obtained with a prototype of an embodiment of the present invention showing the image quality of a sample obtained with the deformable mirror flat and optimized that shows improvement in signal intensity and improvement in resolution in the optimized deformable mirror image.

An embodiment of the present invention can be used for adaptive optics multi-photon imaging. FIGS. 13-21 teach an embodiment of the present invention that performs two-photon microscopy and FIGS. 22 and 23 show experimental adaptive optics two-photon results. The emission source 705 in the prototype is a commercially available Titanium-Sapphire femtosecond laser (Thorlabs Octavius-2P), as shown in FIG. 21(C). The adaptive optics element 715 in the prototype is a commercially available MEMS deformable mirror with 140 actuators, gold coating, grid actuator layout, electrostatic actuation, and 4.4 mm active area (Boston Micromachines Multi-DM) 2105, as shown in FIG. 21(B). The beam projection module 720, diagramed in FIG. 13, comprises four commercially available galvanometers (Cambridge Technology 6210H X-Y scanners). Each pair of X-Y scanners is controlled by an analog controller sold with the galvos that performs close loop control of the galvo angle position. An analog voltage signal is used as input to the controller to command a desired galvo position angle. As shown in FIG. 13(A), light enters the beam projection module 1305 and reflects off a first steering mirror 1310, labeled X mirror 1. Light then travels to a second steering mirror 1315, labeled X mirror 2. X mirror 1 and X mirror 2 work together to control the angle and position of the beam in the X scanning direction. Light from X mirror 2 travels to a steering mirror 1320, labeled Y mirror 1, which reflects and directs the light to a steering mirror 1325, labeled Y mirror 2. Y mirror 1 and Y mirror 2 work together to control the angle and position of the beam in the Y direction. Note that the X and Y directions are chosen for convenience of illustration and that the ordering of X and Y is interchangeable. The commercial X-Y scanner kit contains a pair of galvos with a small and a large mirror, thus two kits contain two galvos with small mirrors and two galvos with large mirrors. The dynamic performance of the galvo with small mirror is different than the performance of the galvo with a large mirror. It is therefore desirable in the context of the beam projection module to match mirrors size within each scan axis. In the specific embodiment shown, it is desirable to use the two small mirrors 1310 and 1315 in the first stage of the beam projection module (labeled X mirror 1 and X mirror 2 in FIG. 13) and the two large mirrors 1320 and 1325 in the second stage of the beam projection module (labeled Y mirror 1 and Y mirror 2 in FIG. 13). Matching mirror sizes within an stage means that scanning within the stage is simplified because the dynamic performance of the two galvos are similar so they will respond similarly to input command voltage trajectories. Further, placing the two small mirrors before the two large mirrors is advantageous because the beam from X mirror 1 and X mirror 2 has been directed off-axis, requiring a larger Y mirror 1 and Y mirror 2 surface to receive the off-axis beam, as shown in FIG. 14(B). Light reflected from Y mirror 2 exits the beam projection module and travels to the deformable mirror 1330, which has a highly reflective surface to reflect the light towards the output of the beam steering module. Changing the angles of the steering mirrors allows the beam angle incident on and reflected from the deformable mirror 1330 to be changed while at the same time maintaining centration of the beam on the deformable mirror 1330. The output rays depicted in FIG. 13(B) and labeled Direction 1, Direction 2, and Direction 3 illustrate this principle of beam steering that enables a compact interface to the deformable mirror 1330 and scanning of the beam on the sample. FIGS. 13(A) and 13(B) show a projection view of FIG. 13(B) and FIG. 13(D) an isometric view of the beam steering module and adaptive optics element assembly. FIGS. 14(A and B) show a solid model drawing of the beam steering module 1405 in which the steering mirrors and the deformable mirror surface are shown relative to the input and output beams. FIG. 15 shows the steering mirror locations and angles of the prototype embodiment.

The controller 725 for controlling the motion trajectories of the axes in the beam projection module 720 of this embodiment comprises software code running on a PC computer 1605 (Dell desktop PC), a digital to analog converter (DAC) board 1610 (National Instruments PCIe-6323), and the analog controllers for the galvos 1615 and 1620, as shown in FIG. 16(A). The PC computer 1605 contains a central processing unit 1625 (CPU). An algorithm 1630 is executed by the CPU 1625 to generate mirror angle trajectories for each of the galvos to accomplish scanning a desired optical spot trajectory in the imaging field (imaging plane). The mirror angle trajectories are stored as an array in computer memory. To perform the scan, the mirror angle trajectories represented as digital data are output by the DAC board at a fixed rate of 100,000 samples per second at 16 bits of DAC resolution as an analog output voltage on each of four channels, Ch1 through Ch4. The outputs of Ch1 through Ch4 are connected by electrical cabling 1635 to the inputs of the two galvo controllers, 1615 and 1620. Each of the two galvo controllers 1615 and 1620 performs close loop control for two channels of the four galvos 1640, 1645, 1650, and 1655 in the beam projection module 1660. FIG. 16(B) shows how a scan trajectory is generated referenced to the imaging field (imaging plane) coordinate system by a scan trajectory generator 1665 as a first step. Based on the geometry of the beam projection module, a set of galvo angles that are required to generate the desired scan pattern in the field can be calculated by a mirror angle calculation 1670. The mirror angle calculation takes as input the X and Y field positions and generates corresponding X1 galvo, X2 galvo, Y1 galvo, and Y2 galvo steering mirror command angles. The X1 galvo, X2 galvo, Y1 galvo, and Y2 galvo commands that are digitally represented and stored in computer memory are transmitted to the DAC 1675 to be converted to analog output signals to be output from Ch1, Ch2, Ch3, and Ch4.

Figure 17:
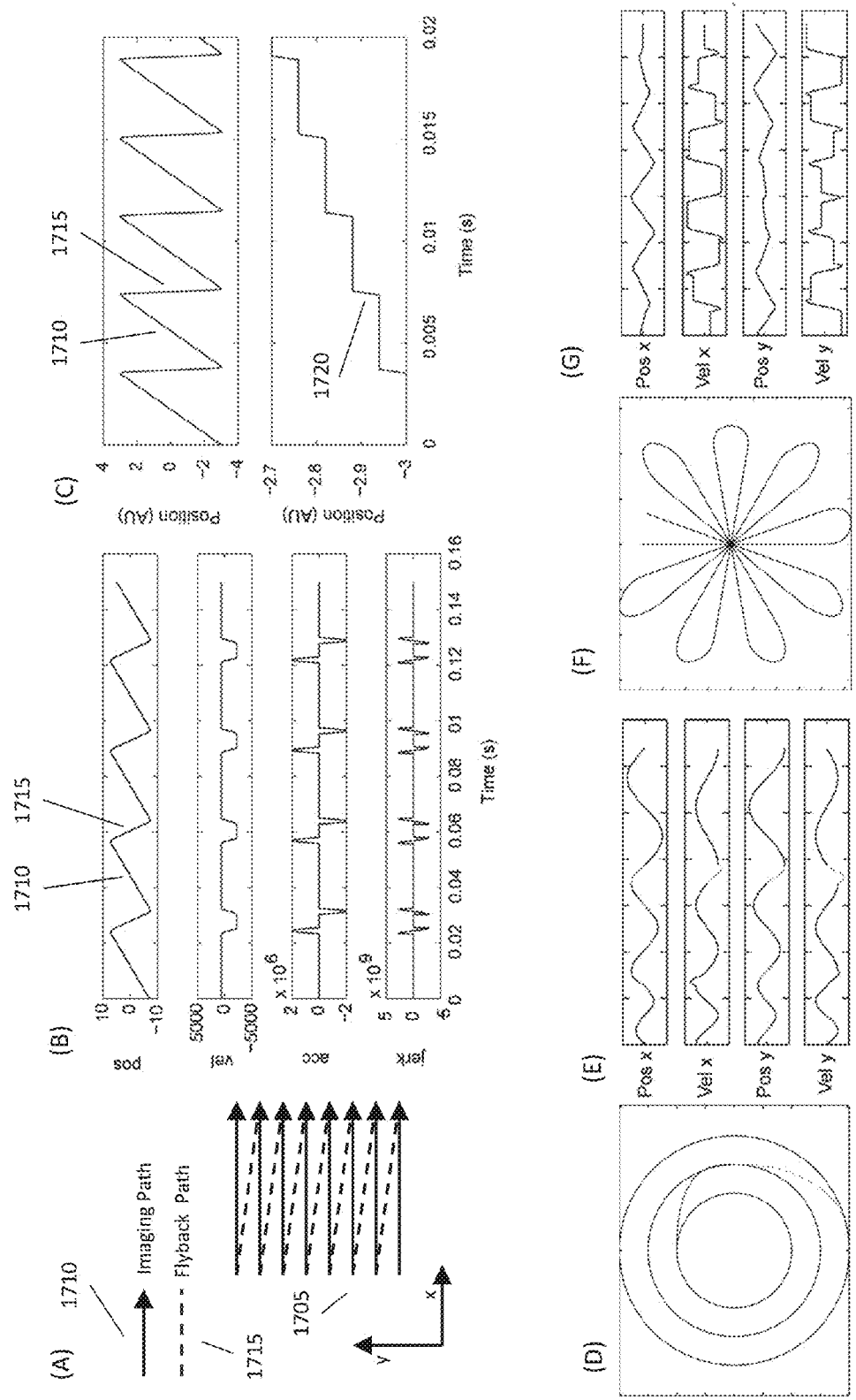
FIG. 17 is a set of plots showing scanning characteristics of an embodiment of the present invention.
Figure 18:
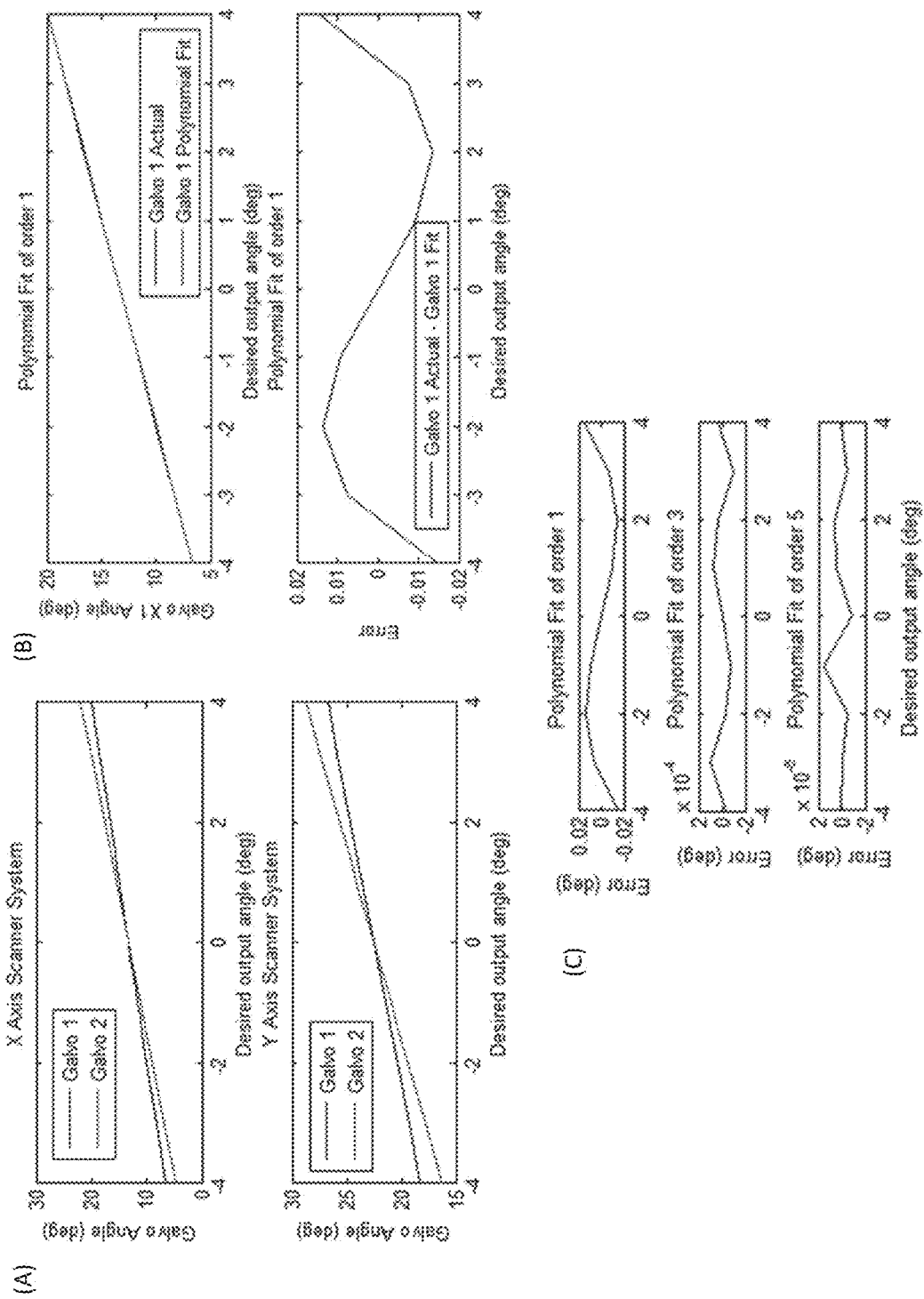
FIG. 18 is a set of plots showing example scan patterns and scan trajectories of an embodiment of the present invention.
Figure 19:
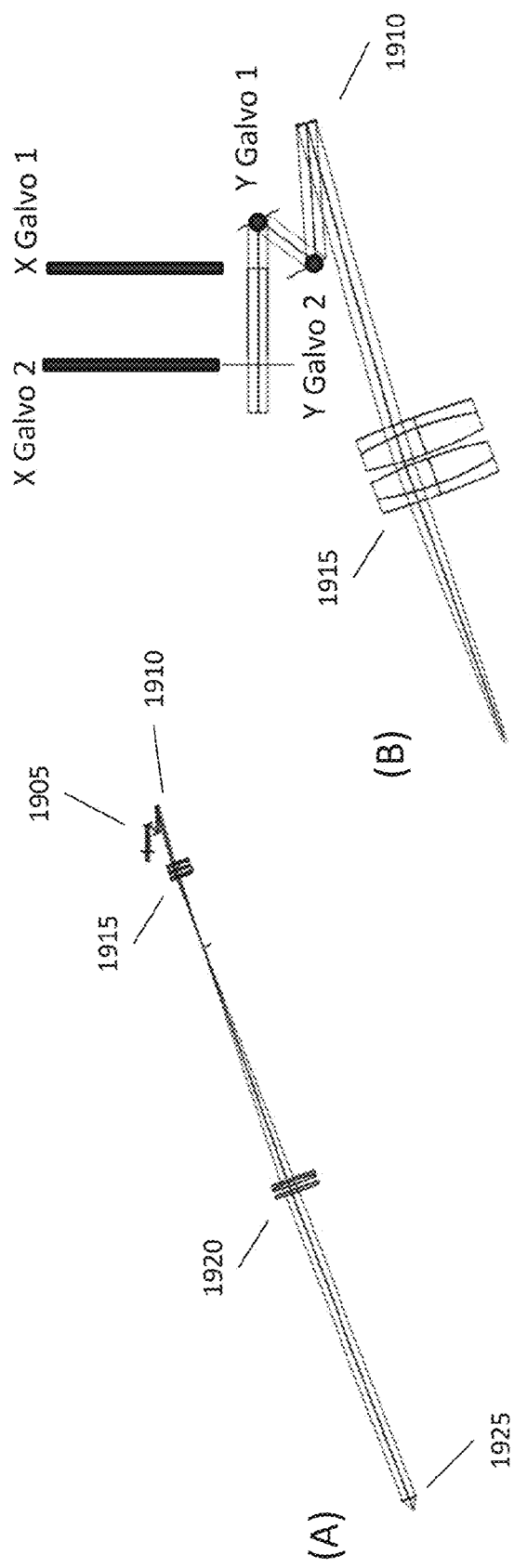
FIG. 19 is a ZEMAX raytrace of a simulation of an embodiment of the present invention showing the beam projection module integrated into a laser scanning microscope.

FIG. 17 shows details of the scan patterns used in the imaging field of the experimental apparatus. A raster scan pattern 1705 consists of a repeated sequence of left to right imaging paths that scan the optical spot across the sample at constant velocity in the x direction, as shown in FIG. 17(A) and FIG. 17(B). As the optical spot is scanned across the sample, an A/D converter reading light intensity collected from the PMT measures the signal from the sample, the data being used to generate a row of data in the final two photon image. At the end of each constant velocity x direction scan of the imaging path 1710, the scan pattern defines a rapid flyback motion or path 1715 to return the spot to the start of a new constant velocity x direction scan 1710. At the same time as the flyback, the scan pattern defines a small upwards movement of the optical spot in the y direction, a row stepping movement 1720, to scan the next adjacent row. In practice, galvanometers can only track within limited closed loop dynamic bandwidth and are subject to oscillation and ringing effects when commanded by trajectories that are not suitably smooth and within achievable motion limits. FIG. 17B shows details of the forwards scanning and flyback trajectory used for raster scanning in the prototype embodiment. The trajectory is based on half sine wave profiles in acceleration, which is well studied and a common trajectory used in the field of motion control and robotics to reduce undesirable excitation of vibratory and resonant modes when there are acceleration and velocity constraints on a dynamic system. The derivative with respect to time of the half sine acceleration is the jerk profile, which is bounded in value. The integral with respect to time of the half sine acceleration profile is the velocity profile. The integral with respect to time of the velocity profile is the position profile, which is used as the motion path in the field reference frame. FIG. 17(C) shows the scan trajectories of the imaging path and flyback for the x direction scanning in the top plot and the associated row-stepping movement in the bottom plot. The row stepping movements 1720 are also based on half-sine acceleration profiles. Other scan trajectories are possible and desirable for imaging and optimization. FIG. 17(D) shows concentric constant velocity imaging circles scanned with respect to field position with each the circles being joined with small non-imaging path segments. The associated x and y field positions and field velocities are plotted in FIG. 17(E). FIG. 17(F) shows a radial cross pattern imaging scans joined by non-imaging turnaround segments that are each optimal with respect to galvo acceleration and velocity constraints. The associated x and y field positions and field velocities are shown in FIG. 17(G). Scanning trajectories defined in the field reference plane are transformed into galvo coordinate system trajectories for execution.

FIG. 18(A), top, shows the galvo angles that are required to generate the desired output angle for the x direction as determined by solving the ray tracing equations by numerical methods. The scan geometry was defined with the ZEMAX ray tracing software and the nonlinear solver (optimizer) used to calculate the steering mirror angles that generate the desired output beam position and angle. FIG. 18(B), bottom, shows the required galvo angles that are required to generate the desired output angle for the y direction as determined by solving the ray tracing equations by numerical methods. These plots represent calibration curves such that required galvo angles can be determined from an input of a desired scan angle in the imaging field coordinate system. The curves look predominately linear, as can be seen in FIG. 18(B), top, where a first order polynomial is fit to the calibration curve data using linear regression. FIG. 18(B), bottom, shows the residual fit error and the nonlinearity in the calibration data. The high degree of linearity in the calibration curve indicates that it is possible to run an embodiment of the present invention with a linear calibration curve, although there will be a small error. Higher order fits to accommodate the non-linearity can be used for improved calibration performance. FIG. 18(C) shows the residual error for polynomial fits of order 1, 3, and 5, with each increasing order showing improved calibration curve performance. Other parameterizations and basis can be used to represent the calibration curve, including interpolation methods or selection of other basis functions. A linear calibration was used in the experimental prototype such that the voltage applied to each galvo was: $V_{galvo\_x1}=C_1\theta_x+C_2$, $V_{galvo\_x2}=C_3\theta_x+C_4$, $V_{galvo\_y1}=C_5\theta_y+C_6$, $V_{galvo\_y2}=C_7\theta_y+C_8$, where V is the command voltage to the galvo as indicated in the subscript, $\theta_x$ is the x field position, $\theta_y$ is the y field position, the odd indexed coefficients of C are scaling factors, and the even indexed confidents of C are DC offset values of the calibration curve. Because the absolute rotational angle of the galvo within the machined mount for the galvos was not controlled (i.e, the galvo itself could rotate within the bore hole of the machined mount before being tightened with a set screw), the DC offset values were determined by finding the analog output voltage that centered the beam on all of the mirrors and generated an output beam centered on the deformable mirror. The angle to voltage conversions for the scaling factors were determined experimentally by directing a laser into the beam projection module and measuring spot locations on a projection screen located a known distance from the output of the beam projection module as the voltages to the galvos were changed.

The beam projection module 1905 and deformable mirror 1910 are combined with a scan lens 1915, tube lens 1920, and objective 1925 to form the sample delivery optics 730 of a two-photon microscope, as shown in FIG. 19(A). A zoom in on the beam projection module shows a schematic of the beam projection module described in detail in FIGS. 13-15. The steering mirrors are angled to create an off-axis scan position with rays traced with ZEMAX in FIG. 15(B). FIG. 20 shows the lens prescriptions and lens spacing of the two-photon microscope. A long pass dichroic mirror (680 nm-1600 nm) 2005 is placed in the excitation path to pass the long wavelengths of the laser source to the sample and reflect the fluorescent signal through a filter cube 2010 containing an emission dichroic filter and an emission bandpass filter 2015, to the PMT detector 2020, where the emission dichroic filter and emission bandpass filter are chosen based on the fluorescent properties of the sample being imaged. The objective 2025 is a commercially available water dipping objective (Nikon LWD 16× 0.8NA). The detector 2020 was a commercially available PMT (Hamamatusu H7422PA). Photographs of the experimental prototype of an embodiment of the present invention are shown in FIG. 21, where the four galvos are indicated with 1-4 in FIG. 21(A) and the deformable mirror (DM) 2105 indicated in FIG. 21(B). The experimental setup is shown in FIG. 21(C). This apparatus was used to image a paper sample 710 on a microscope slide with an optical gel applied to the coverslip to generate an aberration. The index of refraction of the gel was similar to brain tissue and the gel surface textured to create a phantom brain sample. FIG. 22 shows a screen capture from a software to control the prototype. An image of the sample 2205 is shown. The optimized deformable mirror shape 2210 can be seen. A plot 2215 showing the progress of the optimization is shown. The resulting amplitudes of the basis functions applied to the deformable mirror can be seen in a plot 2220. FIG. 23 shows images of the sample with deformable mirror flat 2305 and deformable mirror optimized 2310. The flat mirror image 2305 suffers from the aberrations from the gel. The optimized mirror image 2310 shows increased signal and improved resolution by correcting for the aberrations generated by the gel by properly shaping the deformable mirror.

The adaptive optics convergence algorithm was based on the algorithm presented in "Image based adaptive optics through optimisation of low spatial frequencies" by D. Debarre, M. Booth, and T. Wilson, Opt. Express 15, 8176-8190 (2007) and "Image-based adaptive optics for two-photon microscopy" by D. Débarre, E. Botcherby, T. Watanabe, S. Srinivas, M. Booth, and T. Wilson, Opt. Lett. 34, 2495-2497 (2009) which teach and demonstrate sensorless adaptive optics algorithms and implementation for adaptive optics two-photon optimization.

It is noted that the same optical instrument used for multiphoton imaging can also be used for second harmonic imaging with proper selection of emission filters and excitation wavelength. It is also possible to reduce the size of an embodiment of the present invention by using custom designed optics instead of off-the-shelf optics.

OCT Imaging Embodiment

Figure 24:
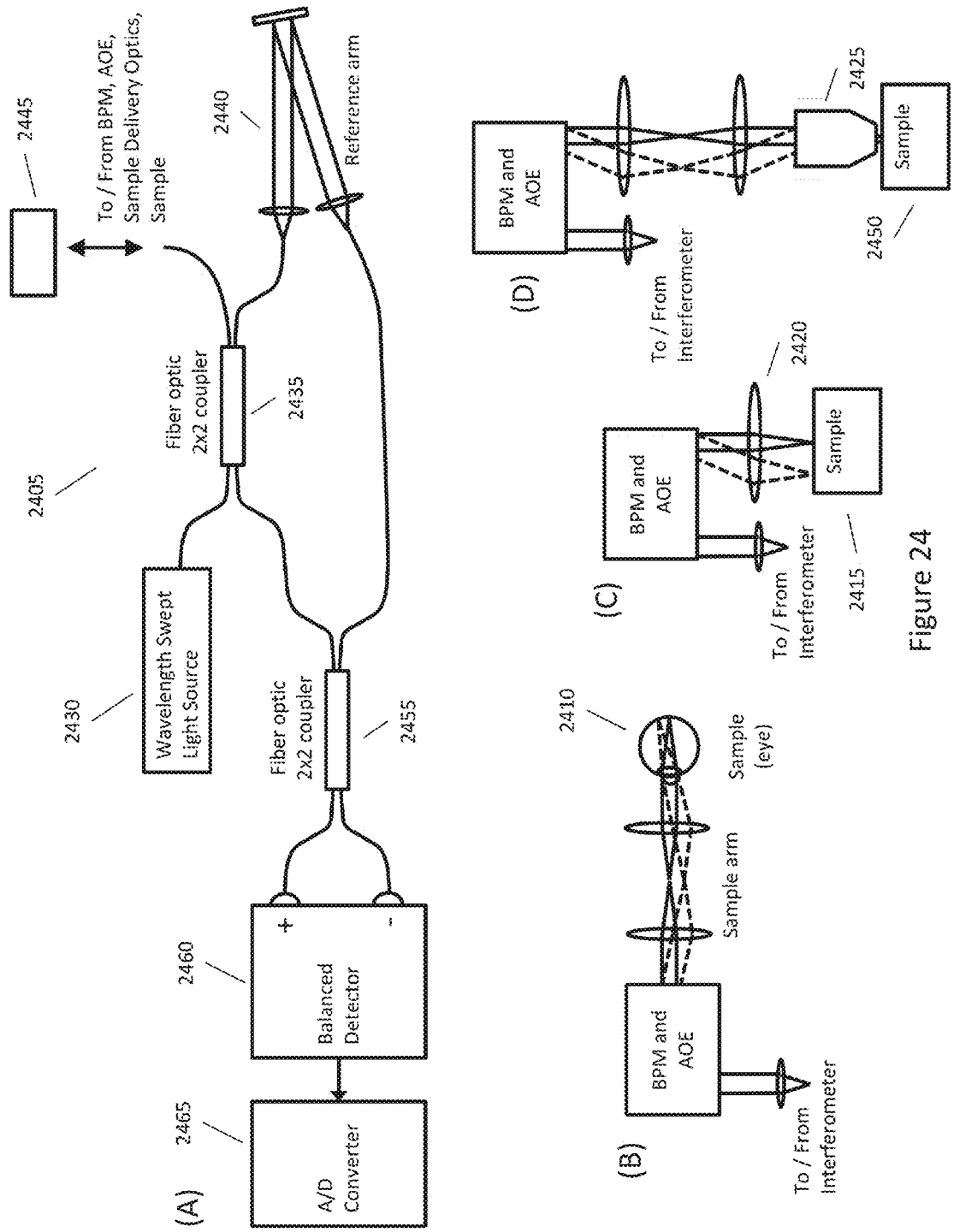
FIG. 24 is a set of drawings showing OCT implementations of an embodiment of the present invention.
Figure 25:
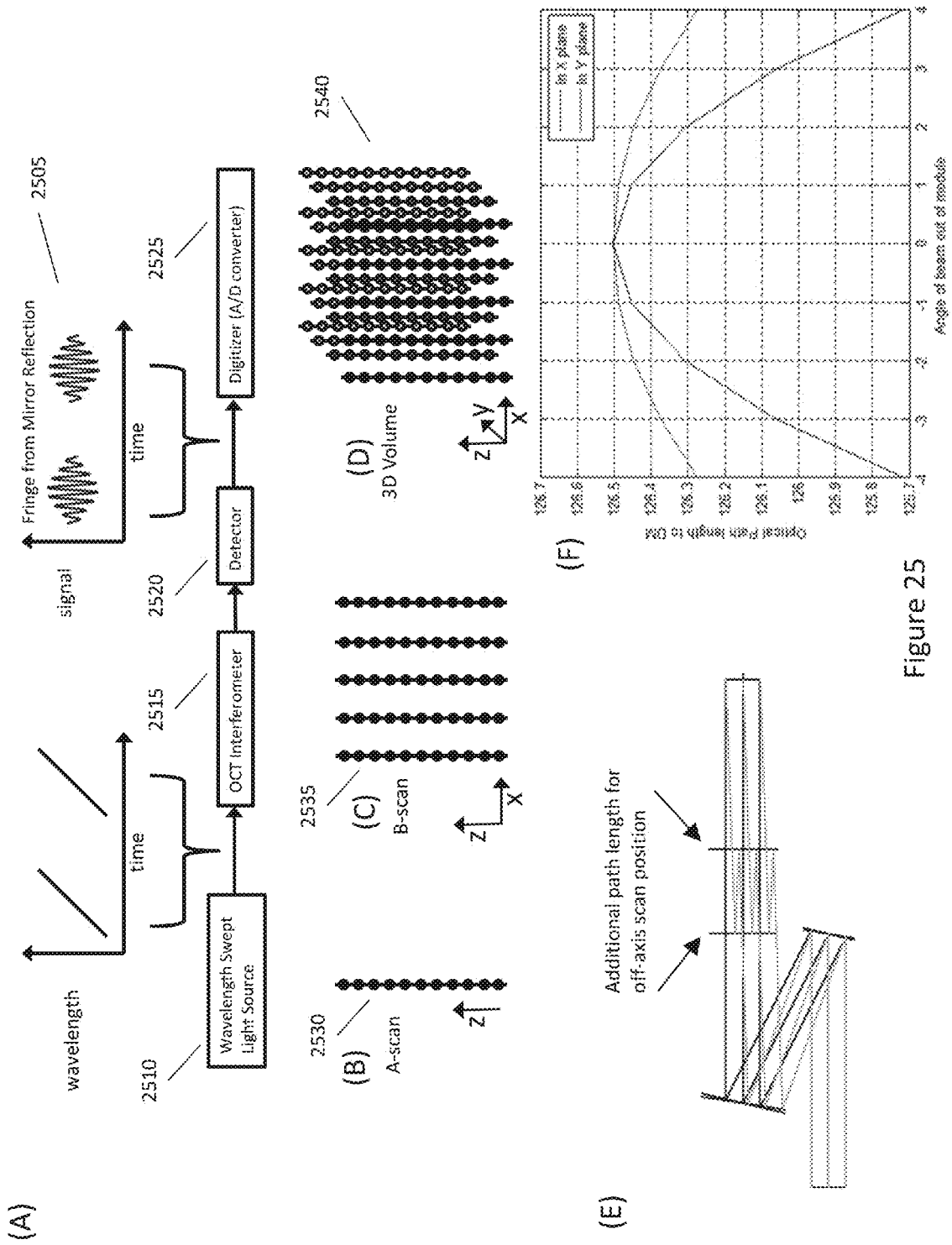
FIG. 25 is a set of drawings and plots showing principles of OCT imaging and optical path length change of an embodiment of the present invention.

An embodiment of the present invention can be used for adaptive optics OCT imaging. FIG. 24 shows an adaptive optics OCT imaging system that uses swept source OCT (SS-OCT) detection, sometimes called swept source/Fourier domain OCT, or optical frequency domain imaging (OFDI). The same basic interferometer 2405 design shown in FIG. 24(A) can be interfaced to different sample delivery optics. FIG. 24(B) shows sample delivery optics suitable for imaging an eye 2410. FIG. 24(C) shows sample delivery optics suitable for imaging a sample 2415 that includes a focusing objective or scan lens 2420 that has an external pupil. FIG. 24(D) shows sample delivery optics suitable for imaging with a microscope objective 2425 or other similar objective that has a pupil internal to the scan lens. In swept source OCT, a wavelength swept light source 2430 generates light with an emission that sweeps a narrowly tuned wavelength in time, as shown in FIG. 25(A). Light from the emission source 2430 is fiber coupled to a first fiber coupler 2435, as shown in FIG. 24(A). A portion of the light is split and directed to a reference path or alternately called a reference arm, 2440. The other portion of the light is split in the fiber coupler and directed to the beam projection module (BPM), adaptive optics element (AOE), and sample optics 2445. Light from the sample optics is directed to a sample 2410, 2415, 2450. Backscattered and reflected light from the sample 2410, 2415 or 2450 is collected by the sample optics and returns through the optical fiber. A portion of the light returning from the sample 2410, 2415 or 2450 passes through the first fiber coupler 2435 to a second fiber coupler 2455 where it interferes with light from the reference arm 2440. Light from the second fiber coupler 2455 is directed to a balanced detector 2460 which converts the light to an electrical signal for each channel, subtracts the signals from the channels, and generates a voltage output. The voltage output is digitized by an analog to digital converter (A/D) 2465 to form an interferogram 2505, as shown in FIG. 25(A). The interferogram is Fourier transformed to generate the reflectivity vs. depth profile, called an axial scan or A-scan 2530. Scanning across the sample and assembling adjacent A-scans can form a two dimensional cross sectional image, a B-scan 2535. Scanning the imaging spot over the sample in a raster scan pattern and assembling adjacent B-scans can form a three dimensional volumetric data set 2540. It should be noted that implementations of OCT other than swept source OCT are also possible, including spectral domain OCT (SD-OCT), sometimes called spectral/Fourier domain OCT, which uses a broadband light source and spectrometer, and time domain OCT (TD-OCT), which uses a broadband light source, single point detectors, and a moving mirror in the reference arm. OCT is a well developed field and there is a large body of literature teaching different OCT implementations including OCT systems that use fiber optic components, OCT system that use bulk optics components, OCT used for Doppler measurement, OCT used for polarization sensitive measurement, and others. Any point scanning OCT method can be used in an embodiment of the present invention. However, in the context of an embodiment of the present invention, swept source OCT offers advantages over spectral domain OCT and time domain OCT because of the short time integration and efficient sampling in the swept source detection method.

One challenge that arises when using an embodiment of the present invention for OCT is that there is a path length change that occurs during scanning. FIG. 25(E) shows a ray trace of the beam projection module for an on-axis field position and an off-axis field position. Because of the forwards and backwards reflections off the mirrors, there is an additional optical path length introduced for the off-axis scan positions. Further, the amount of additional optical path length change vs. field position is different for the x and y axis because of the different mirror spacing, as shown in FIG. 25(F). Because the interferogram in OCT is a function of the difference in path length between the reference arm and the sample arm, a first effect of the optical path length change in the beam projection module is to add a distortion to the OCT image. FIG. 26(E) shows what would be expected from an OCT B-scan cross sectional image 2650 of a flat mirror reflection, while FIG. 26(F) shows distortion to the image 2655 due to the longer path lengths at off-axis scan angles. A second effect of the change in path length is to alter the shape of the interferogram, potentially reducing OCT instrument sensitivity, degrading axial resolution, and introduction depth measurement error. These effects can be better understood by looking at the equations related to generating the interferogram. Refer to Eq. 1 below, where $k_m$ is the wavenumber at sample point m, $I[k_m]$ is the instantaneous photocurrent at sample point m, $\rho[k_m]$ is the detector responsively at sample point m, $S[k_m]$ is the instantaneous power on the sample at sample point m, $R_R$ is the reflectivity of the reference mirror, $R_S$ is the reflectivity of the sample mirror, $z_r$ is the depth of the reference mirror, and $z_s$ is the depth of the sample arm mirror. Equation 1 was adapted from J. A. Izatt and M. A. Choma, Section 2.7, W. Drexler and J. G. Fujimoto Ed., "Optical Coherence Tomography: Technology and Applications", 2008. In practice, the photocurrent, I, is generally transformed into a voltage by a transimpedance amplifier before A/D digitization. A wavelength swept light source 2510 generates an emission that tunes the wavelength in time, as shown in the wavelength vs. time plot in FIG. 25(A). Light travels through the OCT interferometer 2515 where a photodiode converts the light intensity into current, $I[k_m]$, which is transformed to a voltage output signal by a detector 2520. As the wavelength sweeps in time, the A/D converter 2525 digitizes the output of the detector 2520 to generate the OCT interferogram 2505.

$$I[k_m] = \frac{\rho[k_m]}{2} S[k_m](R_R + R_S + 2\sqrt{R_R R_S} \cos(2k_m(z_r - z_s))) \qquad \text{Eq. 1}$$

The term inside the cosine function represents the phase of the OCT interferogram or alternately called OCT fringe. As the phase increases (or decreases), the OCT fringe oscillates with a full period of oscillation occurring every $2*\pi$ radians. A wavelength sweep has a starting wavenumber, $k_{start}$, and an ending wavenumber, $k_{end}$. The number of oscillations in the OCT fringe is proportional to the magnitude of the total phase difference, $\Delta\Phi$, over the sweep, which is given by $$\Delta\Phi = 2(k_{end} - k_{start})(z_r - z_s). \qquad \text{Eq. 2}$$

Figure 26:
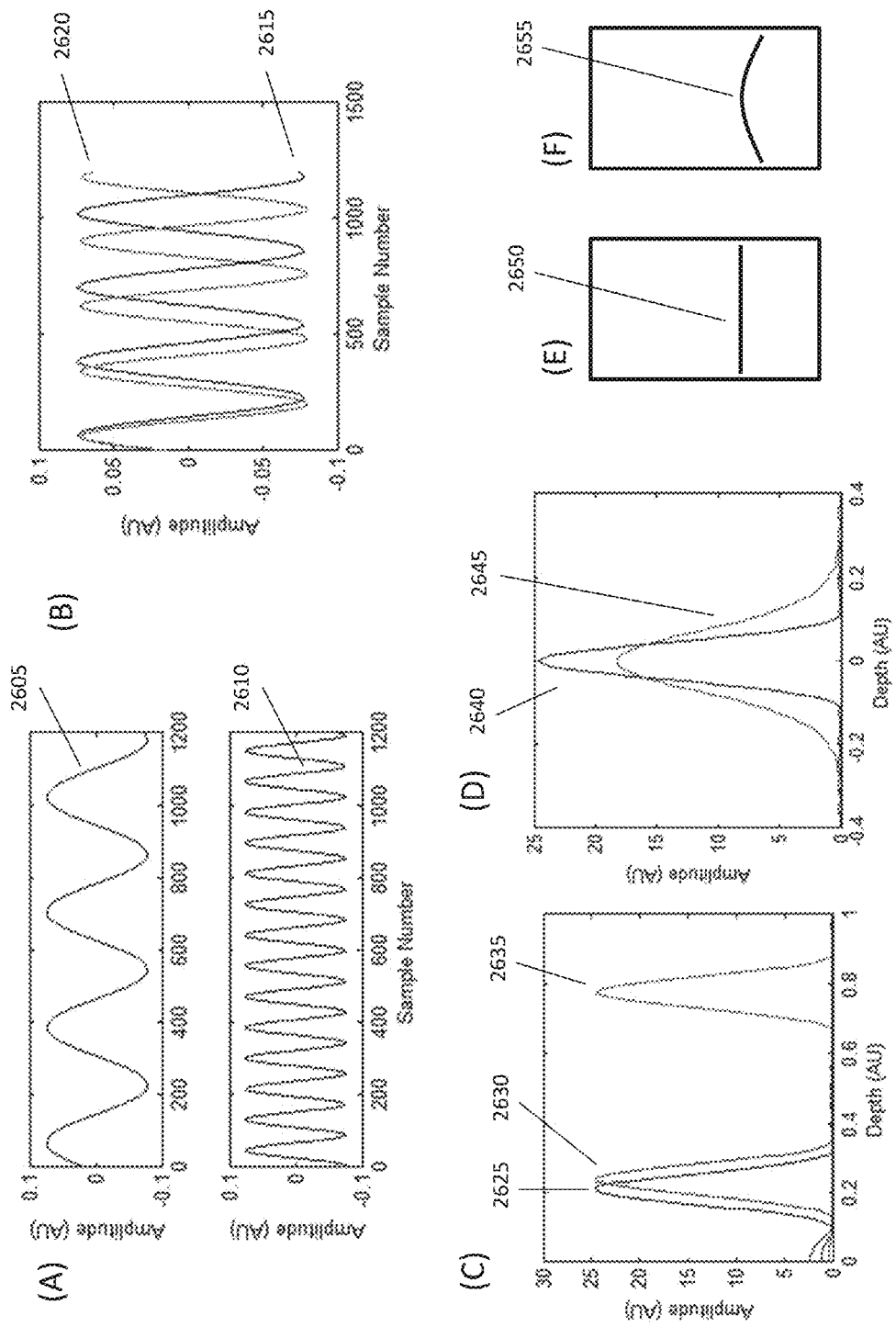
FIG. 26 is a set of plots showing the effect of optical path length change of an embodiment of the present invention when used for OCT.

Equation 2 shows that the fringe frequency increases with increasing imaging depth (i.e., there is a larger number of oscillations over the sweep) because the $(z_r - z_s)$ multiplier term inside the cosine function increases total fringe phase. FIG. 26 shows simulated interferograms resulting from a stationary mirror reflection in the sample arm with wavelength sweep from a starting wavelength, $\lambda_{star}$, to an ending wavelength, $\lambda_{end}$, which given that $k=1/\lambda$ is equivalent to a starting wavenumber, $k_{start}$, and ending wavenumber, $k_{end}$, and also where the sample points in the interferogram are equally spaced in wavenumber, as is commonly performed in swept source OCT by optical clocking or numerical calibration methods. FIG. 26(A), top, shows an interferogram 2605 from a mirror at a shallow depth and FIG. 26(B), bottom, shows and interferogram 2610 from a deep depth. As expected from Eq. 1 and Eq. 2, the number of oscillations for the deep mirror reflection is larger than the number of oscillations for the shallow mirror reflection because of the larger overall phase resulting from the $(z_r - z_s)$ term. FIG. 26(A) shows the interferogram 2615 for a stationary mirror with fixed path length in the sample arm. If, in the case of an embodiment of the present invention, the path length is changing while the wavelength swept source is sweeping, the effect on the interferogram is that the beginning portions of the interferogram are associated with the starting optical path length and the ending portions of the interferogram are associated with the ending optical path length, which causes the interferogram 2620 to be chirped when compared to the stationary mirror condition, as shown in FIG. 26(B). FIG.

26(C) shows the OCT point spread function 2625 for the shallow fringe 2605, the OCT point spread function 2635 for the deep fringe 2610, and the OCT point spread function 2630 for the chirped fringe 2620. FIG. 26(D) shows the OCT point spread function for the shallow fringe 2605 and for a heavily chirped fringe 2645. The chirping has two effects on the OCT axial point spread function when Fourier transformed. First, the depth position of the reflection is shifted to some norm or aggregate optical path length position, and second, the point spread function is potentially broadened as it contains information from multiple depths. Both of these effects are deleterious to OCT imaging performance. In the case of swept source OCT, sampling rates are generally quite fast at several hundred million to 500 million samples per second (MSPS) or faster with modern A/D cards, resulting in short sampling times on the order of nanoseconds per sample. The integration times for spectral domain OCT are much longer because the cameras expose multiple wavelengths and run at tens of kilohertz to several hundreds of kilohertz rates, resulting in integration times on the order of microseconds, orders of magnitude longer than for swept source OCT. For spectral domain OCT, an OCT interferogram that changes in time results in fringe washout effects that can reduce the fringe contrast and compromise OCT sensitivity. Fringe washout effects are less pronounced with swept source OCT because of the order of magnitude shorter integrations times. Nevertheless, the current invention can be practiced with any form of point scanning OCT of image based OCT. Methods for addressing the optical path length change of the current invention for improved performance are described next.

Long coherence length swept source lasers enable a long OCT imaging range to accommodate the change in path length of an embodiment of the present invention. Long coherence length swept laser include technology based on a wavelength tunable vertical-cavity surface-emitting laser (VCSEL), Fourier domain mode locked laser (FDML) and dispersion balanced FDML laser, short cavity laser, and Vernier-tuned distributed Bragg reflector (VT-DBR) laser. A long coherence length laser combined with a fast detector and high digitization rate enable collection of an OCT image with sufficient range to accommodate the image distortion created by the longer optical path length associated with off-axis scan positions.

A calibration can be applied to the OCT image data (after Fourier transforming the fringe) that shifts the data in the axial direction in order to properly align the data in the depth direction to represent the sample morphology. The amount of shift applied to each A-scan can be determined by calculation of the nominal path length change expected from the scan geometry or through experimental methods, such as imaging a known flat mirror and determining the required axial shift that produces a flat surface in the OCT image data, as shown in FIGS. 26(E-F). For many applications, simply shifting the OCT image data is sufficient as the slight degradation of OCT axial resolution associated with chirping of the OCT interferogram would be acceptable. For applications where the highest OCT axial resolution performance is required, it can also be beneficial to address the loss of degradation of the OCT PSF associated with the chirping of the OCT interferogram by numerically correcting the OCT fringe. A proper calibration can be obtained using methods well established and practiced in OCT based on resampling of the OCT fringe and dispersion compensation, such as those taught by Section 2.2 of a paper, "Ultra high-speed swept source OCT imaging of the anterior segment of human eye at 200 kHz with adjustable imaging range" by M. Gora, K. Karnowski, M. Szkulmowski, B. Kaluzny, R. Huber, A. Kowalczyk, and M. Wojtkowski, Opt. Express 17, 14880-14894 (2009), and Section 2.2 of a paper, "Three-dimensional and high-speed swept-source optical coherence tomography for in vivo investigation of human anterior eye segments" by Y. Yasuno, V. Madjarova, S. Makita, M. Akiba, A. Morosawa, C. Chong, T. Sakai, K. Chan, M. Itoh, and T. Yatagai, Opt. Express 13, 10652-10664 (2005). In these methods, a mirror reflection or an MZI is used to generate an OCT fringe and numerical methods applied to create a calibration that is equally spaced in wavenumber, k, and properly dispersion compensated. For an embodiment of the present invention, a flat mirror surface can be scanned and a calibration obtained for every A-scan. Storage of the calibration can be simplified by realizing that the perturbation to a nominal calibration is due to path length change at near constant velocity. So, only the velocity at any one region in the scan needs to be known, stored, and used to calculate the OCT fringe correction.

An alternate approach to address the change in path length introduced by the beam projection module is to adjust the optical path length with a fast actuator such that the path lengths between the reference arm and the sample arm remained matched during the scanning. This method would be preferred if performing spectral domain OCT to reduce fringe washout effects that are more pronounced than in swept source OCT. The path length change could be obtained by using a fast and flexible delay line or by adjusting the path length with a fast actuated mirror. The delay line or fast actuated mirror could be actuated by piezo, electromagnetic, or other actuation. The position of the active mirror would be determined by calibration from a flat mirror reflection, by calculation or simulation such as shown in FIG. 25(F), or other methods.

Other AO System Embodiments

Other embodiments of the present invention are possible. Any of the imaging systems shown in FIG. 1 can be practiced with an embodiment of the present invention by replacing the steering mirror shown with a beam projection module and adaptive optics element. An imaging system for general purpose OCT, similar to that shown in FIG. 1(A), would replace the steering mirror 135 with a beam projection module and adaptive optics element to realize an adaptive optics OCT imaging system of an embodiment of the present invention. An imaging system, similar to that shown in FIG. 1(B), would replace the steering mirror 155 with a beam projection module, adaptive optics element, and controller to realize an adaptive optics OCM imaging system of an embodiment of the present invention when combined with a suitable interferometer, detector, and emission source. An imaging system, similar to that shown in FIG. 1(C), would replace the steering mirror 172 with a beam projection module, an adaptive optics element to realize an adaptive optics OCT imaging system for imaging the eye of an embodiment of the present invention when combined with a suitable interferometer emission source and detector. An imaging system, similar to that shown in FIG. 1(D), would replace the steering mirror 177 with a beam projection module, an adaptive optics element, and controller to realize an adaptive optics confocal imaging system of an embodiment of the present invention when combined with a suitable emission source and detector. An imaging system, similar to that shown in FIG. 1(E), would replace the steering mirror 192 with a beam projection module, an adaptive optics element, and controller to realize an adaptive optics laser scanning ophthalmoscope imaging system of an embodiment of the present invention when combined with a suitable emission source. An imaging system, similar to that shown in FIG. 1(F), would replace the steering mirror 199 with a beam projection module, an adaptive optics element, and controller to realize an adaptive optics multiphoton or second harmonic imaging system of an embodiment of the present invention when combined with a suitable emission source. An optical tweezers implementation of the current invention can also be realized by replacing the beam steering mirrors in an optical tweezer setup with a beam projection module, an adaptive optics element, and controller. In optical tweezers, the detector is often a digital camera.

Conjugation of Adaptive Optics Element

Selecting the plane of conjugation of an adaptive optics element in an optical system is an important consideration for achieving a large correctable field of view with a single adaptive optics correction. Because the light traverses a different optical path as the beam is scanned across the sample, the can aberrations change for each field position. The rate of change of the aberrations and associated point spread function (PSF) with field position depends on the characteristics of the aberrating source and details of the optical layout. The isoplanatic patch is a measure of how quickly the PSF changes with field position and is sometimes defined as the region over which the root mean square (RMS) wavefront difference between any two wavefronts within the patch is less than a critical value, although alternate definitions of the isoplanatic patch have also been used in the literature. In this patent application, the concept of instantaneous diffraction limited field of view is used to evaluate and compare adaptive optics performance, where diffraction limited is defined as a Strehl ratio greater than or equal to 0.8, and instantaneous indicates using only a single adaptive optics correction. In certain applications, the improvement in imaging performance may be significant, but not reach performance of the diffraction limit. Improvement in the performance in similar fields of view, or an increase if the size of the field of view at a critical performance level are also useful and can be achieved with an embodiment of the present invention.

Most adaptive optics imaging system literature and description teach conjugating the adaptive optics element to a pupil plane of the system. In adaptive optics microscope systems, the adaptive optics element is often conjugated to the pupil plane of the microscope objective, as taught in the papers, "Adaptive optics via pupil segmentation for high-resolution imaging in biological tissues" by N. Ji, D. Milkie, and E. Daniel, Nature Methods, 7, 141-147 (2009), a paper, "Image-based adaptive optics for two-photon microscopy" by D. Débarre, E. Botcherby, T. Watanabe, S. Srinivas, M. Booth, and T. Wilson, Opt. Lett. 34, 2495-2497 (2009), and other papers. In adaptive optics scanning laser ophthalmoscopes and adaptive optics OCT systems, the adaptive optics element is often conjugated to the pupil of the eye. For scanning optical systems, conjugating the adaptive optics element to the pupil maximizes the number of actuators across the imaging beam and results in a stationary beam center in both the adaptive optics plane and the pupil plane while scanning. A paper, "Requirements for discrete actuator and segmented wavefront correctors for aberration compensation in two large populations of human eyes" by N. Doble, D. Miller, G. Yoon, and D. Williams, Appl. Opt. 46, 4501-4514 (2007), investigates the requirements on the stroke and number of actuators across the pupil in populations of human eyes. A different paper, "Statistical variation of aberration structure and image quality in a normal population of healthy eyes" by L. Thibos, X. Hong, A. Bradley, and X. Cheng, J. Opt. Soc. Am. A 19, 2329-2348 (2002), investigates the type and magnitude of aberrations in a normal population of eyes. In both of these papers, wavefront measurements are performed along the line of sight, so only a single field position on the eye is investigated. A practical adaptive optics imaging system images not only at a single point, but over an extended field of view. It is also desirable that the adaptive optics correction apply to as large a field as possible. The optimal adaptive optics pupil conjugation can be determined through simulation or experimental methods. The effects of adaptive optics element conjugation are demonstrated next through optical simulation.

Figure 27:
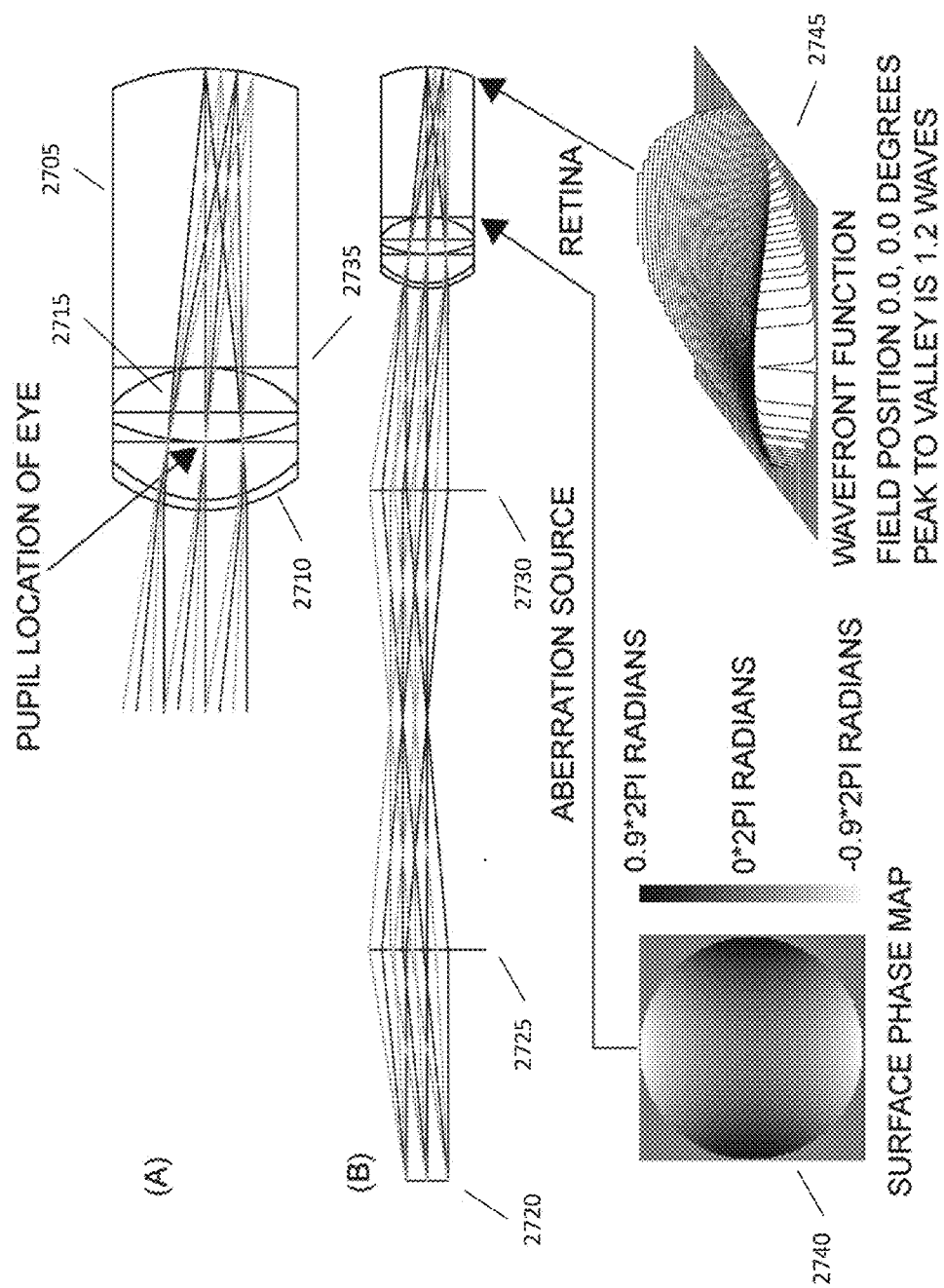
FIG. 27 is a diagram showing an optical simulation of the human eye.

The Liou and Brennan model of the eye is one of the most accurate models of the human eye developed to date and includes morphologically similar surface contours to the eye, gradient index refractive properties of the lens, and an offset pupil position similar to the eye. The model has been shown to match physiologically obtained experimental data, as described in a paper, "Different Schematic Eyes and their Accuracy to the in vivo Eye: A Quantitative Comparison Study" by MS de Almeida and LA Carvalho, Brazilian Journal of Physics 37, pp. 378-387 (2007). FIG. 27(A) shows a ZEMAX simulated ray trace of a model of the human eye 2705 based on the Liou and Brennan model, but with the pupil centered with respect to the optical axis. The pupil diameter is 4 mm, which is larger than the diameter expected to produce optimal lateral imaging resolution because of residual aberration.

Studies of the aging process of the eye have found that the primary cause of increasing refractive error with age is due to changes in the crystalline lens rather than changes in the cornea, as described in a paper, "Optical aberrations and alignment of the eye with age" by Esther Berrio, Juan Tabernero, Pablo Artal, Journal of Vision 10(14) (2010). In a normal and young eye, the aberrations of the cornea 2710 are balanced by aberrations in the crystalline lens 2715. Thus, the source of the aberration in a normally aging eye is not located at the pupil plane itself, but originate because of an imbalance of aberration between the cornea 2710 and crystalline lens 2715. FIG. 27(B) shows the traditional adaptive optics design of a deformable mirror 2720 conjugated to the pupil plane of the eye using a 4f telescope, where the telescope is composed of a first 2725 and a second 2730 paraxial lens surface in ZEMAX. The paraxial lens surfaces act like ideal lenses and do not introduce any aberration of their own. A surface capable of introducing phase error (Zernike fringe phase surface) is located immediately following the crystalline lens 2735 and acts to create an additional imbalance of aberration between the cornea and back surface of the crystalline lens. Light from the deformable mirror 2720 in this simulation is planar and aberration free. Collimated light from the deformable mirror 2720 propagates to the first lens 2725 of the afocal telescope system where it is focused to a converging beam that is in turn collected by the second lens 2730 and re-collimated for projection into the eye model 2705. Aberration free light enters the eye model 2705, is subject to the aberrations inherent in the eye, additionally subject to the aberrations introduced by the aberrating surface, and focuses on the retina. The aberrating surface 2735 is configured to generate astigmatism phase error 2740. A wavefront analysis 2745 of the light at the retina shows the dominate shape of the aberration source combined with the eye's natural aberration.

Figure 28:
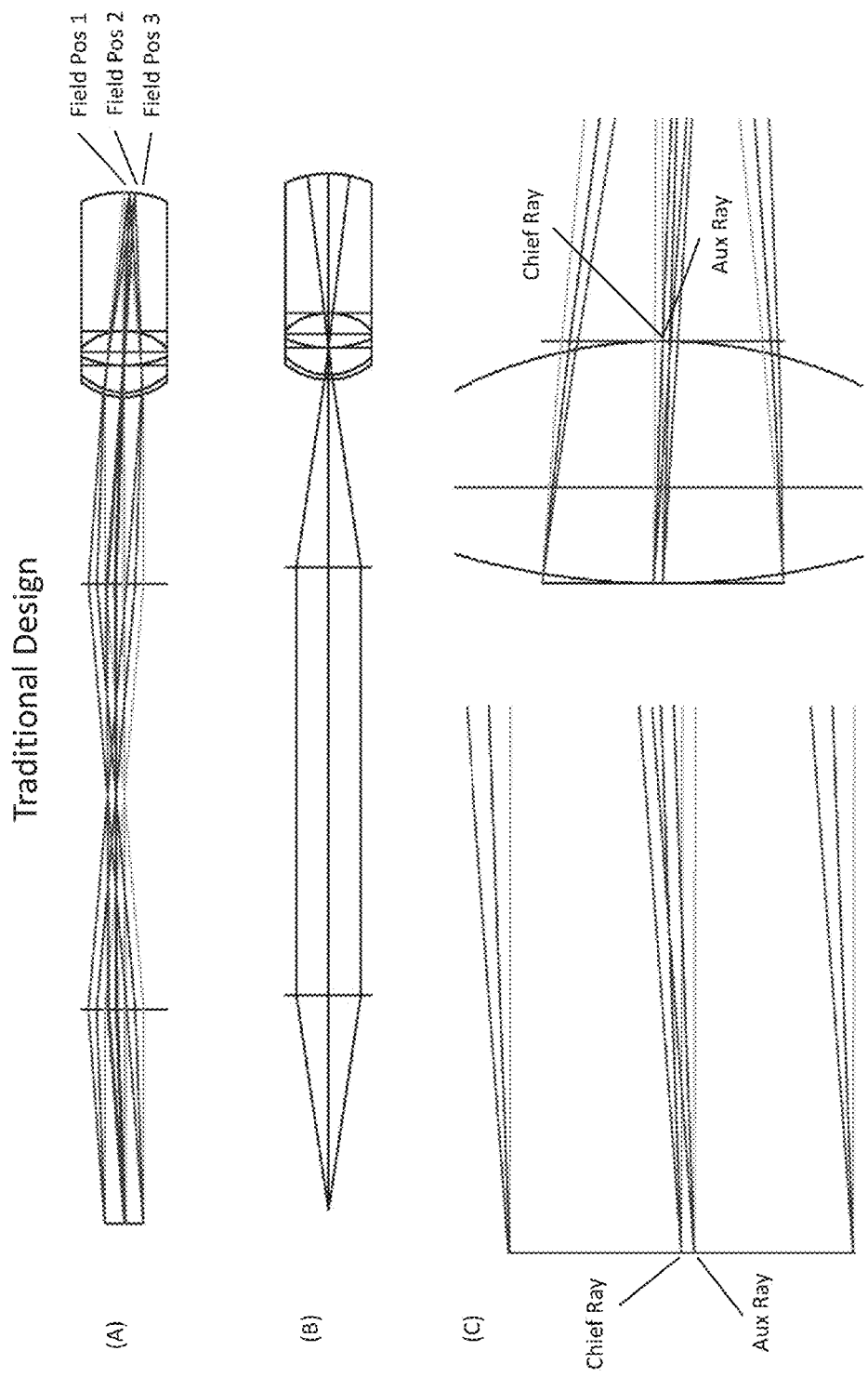
FIG. 28 is a set of drawings that show portions of an adaptive optics imaging system where the adaptive optics element is conjugated to the pupil of a human eye.

FIG. 28 shows additional information about this traditional approach of conjugating the deformable mirror to the pupil in the eye. FIG. 28(A) shows the conjugate image planes in the system. FIG. 28(B) shows the conjugate pupil planes in the system, where it can be seen that the deformable mirror is imaged to the pupil plane of the eye. FIG. 28(C) shows zoomed in ray traces of the deformable mirror and the crystalline lens in the eye where the chief ray, the marginal rays, and an auxiliary ray are labeled. As expected, the chief ray and auxiliary ray are imaged from the deformable mirror to the pupil of the eye with relative ordering and normalized spacing with the beam diameter preserved. However, at the plane of the source of the aberration, the chief ray and the auxiliary ray overlap and cross. This means that a correction applied at the deformable mirror will be blurred at the plane of the source of the aberration and consequently less effective at compensating for the aberrations introduced at this plane.

Figure 29:
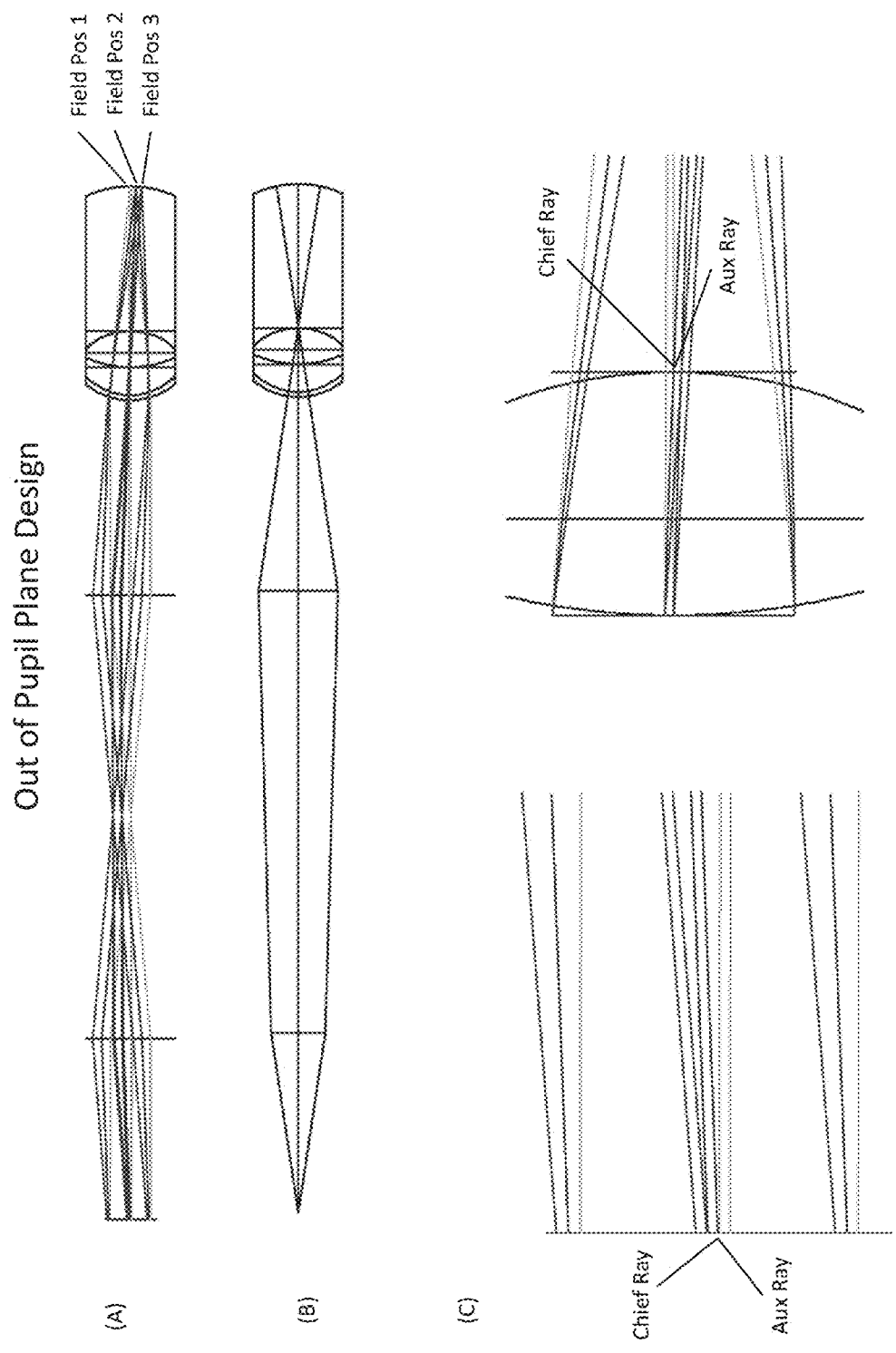
FIG. 29 is a set of drawings that show portions of an adaptive optics imaging system where the adaptive optics element is located outside of a pupil plane in the human eye.

FIG. 29 shows an alternate design in which the lens spacing of the telescope has been adjusted so that the deformable mirror is now conjugated to a plane that is approximately located at the plane of the source of aberration. FIG. 29(A) shows a ray trace of the conjugate image planes. FIG. 29(B) shows a ray trace of the conjugate pupil planes, in which the conjugation between the deformable mirror and the approximate plane of the source of aberration can be seen. FIG. 29(C) shows zoomed in ray traces of the chief ray, marginal rays, and an auxiliary ray. In this alternate configuration, it can be seen that the chief ray and the auxiliary ray intersect at the deformable mirror and also intersect at the plane of the source of aberration. This means that a corrective shape at the deformable mirror is spatially localized in the plane of the source of aberration and is effective at cancelling an aberration at more than one field position.

Figure 30:
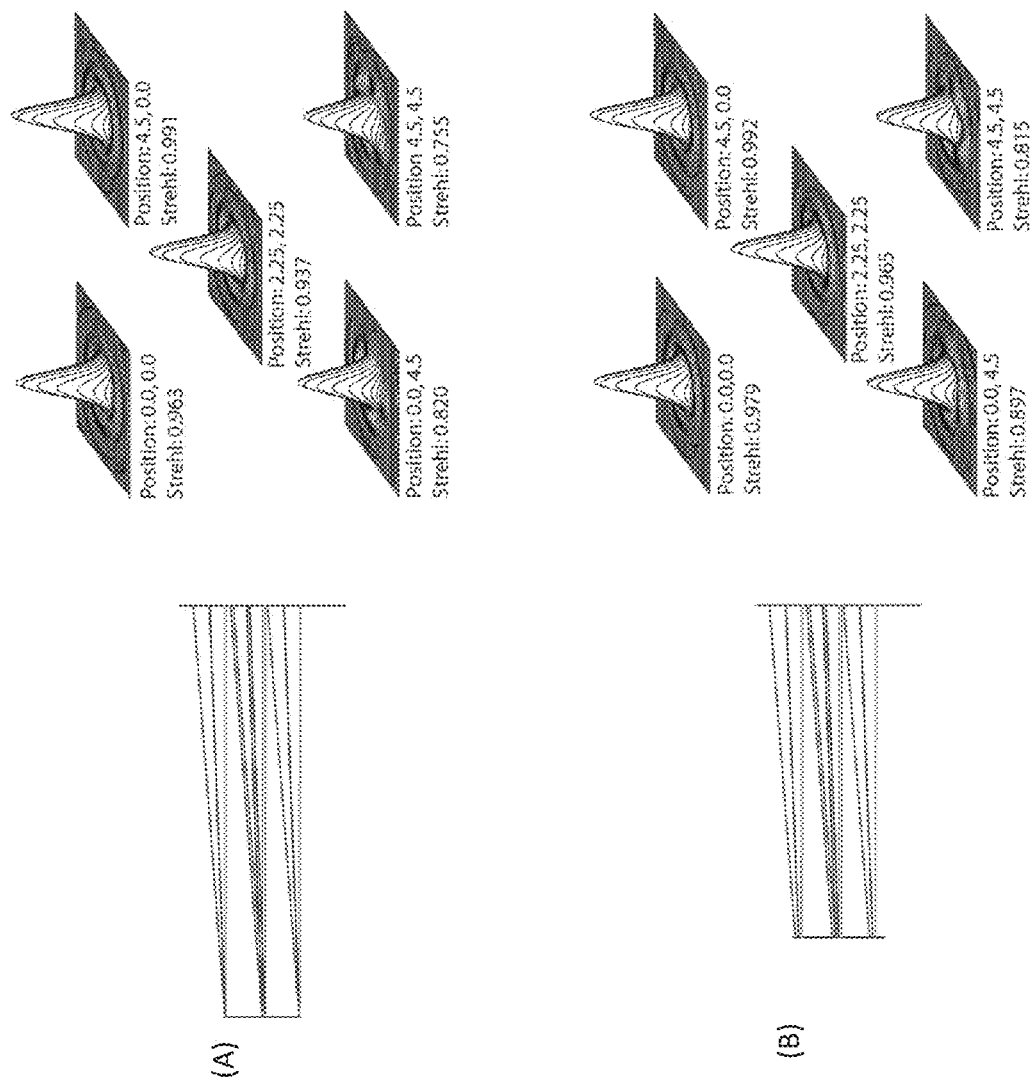
FIG. 30 is a set of drawings and plots comparing the optical layout and imaging performance of systems where the adaptive optics element is located in and located outside of a pupil plane in the human eye.

Imaging over a field size of 4.5 degrees by 4.5 degrees, FIG. 30 compares the performance of the pupil conjugated configuration shown in FIG. 28 and the aberration source conjugated configuration shown in FIG. 29. In these simulations, the deformable mirror (Zernike fringe phase) was parameterized with Zernike modes 4-27 and ZEMAX optimization was used to optimize the deformable mirror shape to simultaneously minimize the RMS wavefront error over five field positions of (0,0), (0,4.5), (2.25, 2.25), (4.5,0), and (4.5,4.5). In the case of the pupil conjugated configuration, the position of the deformable mirror was fixed in order to maintain pupil conjugation. In the case of the aberration conjugated configuration the position of the deformable mirror relative to the first lens of the afocal telescope was defined as a variable and allowed to change during the optimization. In the case of the aberration conjugated configuration, the active diameter of the deformable mirror was forced to match the position of the most extreme ray in the (4.5, 4.5) field position. By using the same Zernike terms in the two different configurations, the relative spatial frequency correcting capability of the deformable mirrors are the same for fair comparison, i.e., the actuator count and influence function of the two mirrors are identical when normalized to the diameter of the adaptive optics element. The results show that over the same field size, the aberration source conjugated configuration outperforms the pupil conjugated configuration with respect to Strehl ratio at all field positions. The aberration source conjugated configuration has diffraction limited performance (Strehl ratio greater than 0.8) over the entire 4.5 by 4.5 field of view, while the pupil conjugated system is not diffraction limited over the entire field of view. This implies that when the aberrations in the eye are primarily due to refractive error near the back surface of the crystalline lens, the optimal position of the adaptive optics element is outside of the pupil plane and somewhere between the pupil plane and the plane of aberration shown. Note that in order for this out-of-pupil scanning scheme to work, the beam diameter must be smaller than the active diameter of the deformable mirror and the beam center must move on the deformable mirror surface, as shown in FIG. 31(E). This results in a small loss of actuator density across the beam, but shows that the advantage of conjugating to the source of aberration outweighs the small loss of actuator density.

Figure 31:
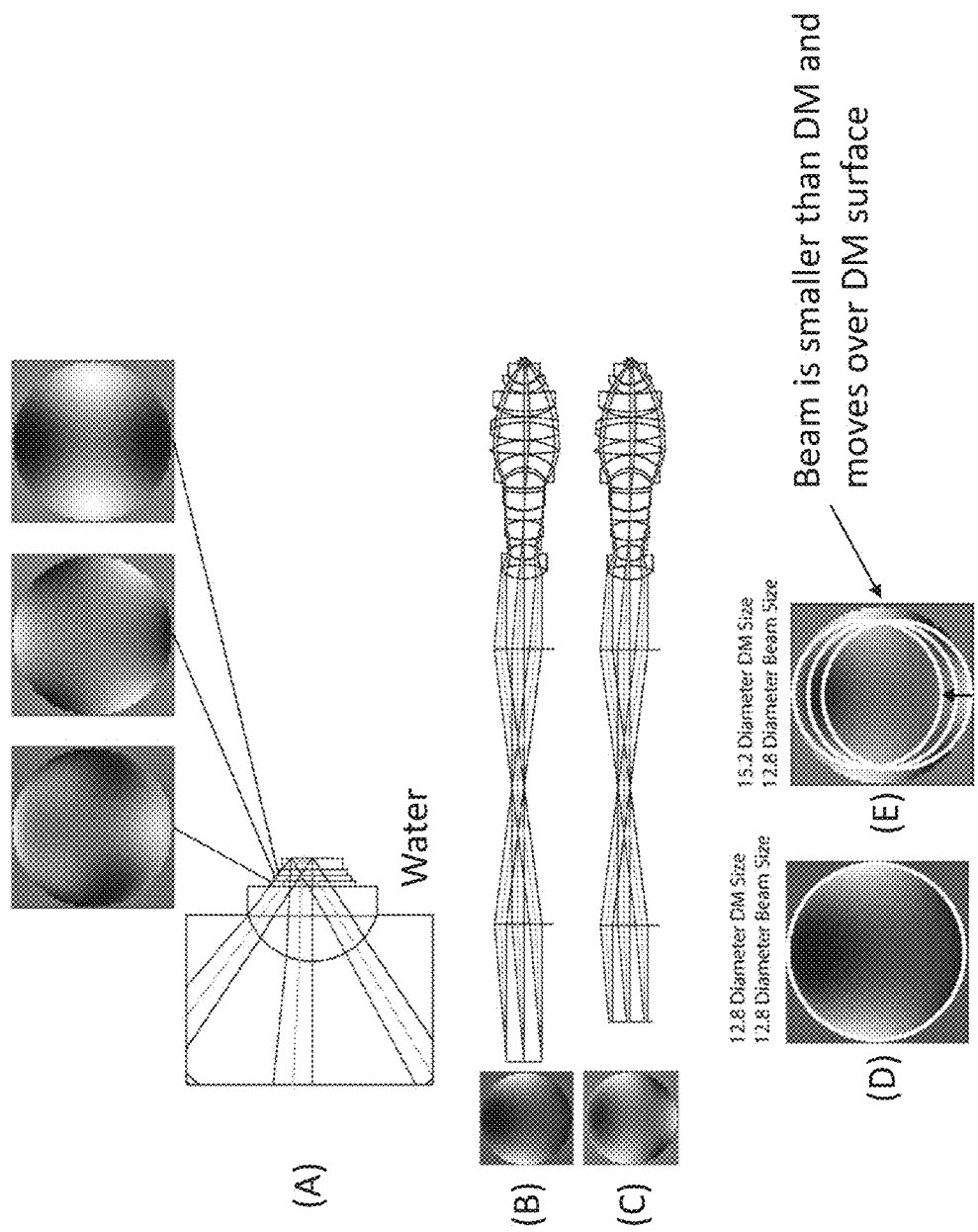
FIG. 31 is a set of drawings and plots comparing a microscope imaging system where the adaptive optics element is located in a pupil plane and outside of a pupil plane in a microscope system.

In the eye, it is possible to locate the general region of the source of the aberration and conjugate to, or approximately conjugate the adaptive optics element to the source of aberration because the source of the aberration is located close to the pupil plane and there is sufficient distance between source of the aberration and the focal plane. In a microscope based imaging system, the source of the aberration is generally very close to the focal plane and is due to the sample itself or a material or optical interface that is adjacent to, touching, or near the sample and imaging plane. It is therefore not necessarily possible to completely conjugate the adaptive optics element to the source of aberration in a microscope system. FIG. 31 (A-C) show a microscope objective where the design form for the lens is derived from a lens prescription described in U.S. Pat. No. 6,501,603. A zoomed view of the rays focusing into the sample as emerging from the last lens in the microscope objective is shown in FIG. 31(A). The objective is a water emersion type and a ZEMAX simulation of the optical performance of the objective contains a layer of water following the last glass element of the objective. The layer of water is then followed by alternating Zernike Phase surfaces and thin water layers before a final layer of water in which there is the optical focus. The Zernike Phase surfaces simulate the more realistic effect of sample induced optical aberration occurring through a depth of the sample (i.e. the aberrations are not contained in a single plane). The shapes of the phase errors introduced by the Zernike Phase surfaces are shown in FIG. 31(A) and together introduce about 1 wave of peak-to-valley aberration. The ability of the deformable mirror to correct the aberrations introduced by the sample is compared by defining the deformable mirror with a Zernike Phase surface using Zernike terms 4-20 and optimizing the shape of the phase correction of the deformable mirror to simultaneously minimize the root mean square (RMS) wavefront error over field positions of 0.0 degrees, 2.5 degrees, and 5.0 degrees input angles. A configuration in which the adaptive optics element is conjugated to the pupil of the objective, shown in FIG. 31(B), is compared to a configuration in which the adaptive optics element is shifted away from the pupil plane by 15 mm, shown in FIG. 31(C). The adaptive optics element is conjugated to a region in the microscope objective by a telescope composed of paraxial lens surfaces with focal lengths of 50 mm. The optimal adaptive optics corrections are shown in FIGS. 31(B) for the pupil conjugated configuration and 31(C) for the out-of-pupil conjugated adaptive optics configuration. The resulting Strehl ratios for the field positions of 0.0, 2.5, and 5.0 degrees are 0.758, 0.887, 0.702 for the pupil conjugated configuration and 0.805, 0.926, 0.837 for the out-of-pupil conjugated configuration. Over the same field size, the out-of-pupil conjugated configuration outperforms the pupil conjugated configuration, indicating the larger diffraction limited field of view obtained with the out-of-pupil conjugated configuration.

Larger diffraction limited fields of view have been demonstrated with out-of-pupil conjugation of the adaptive optics element with examples and simulations of imaging in the human eye and in two-photon imaging through an aberration generating sample over extended field sizes. However, it is important to realize that placing the adaptive optics element out of the pupil plane reduces the effective number of actuators across the beam. FIG. 31(D) shows a beam size that is equal to the active area of the adaptive optics element and thus maximizing the actuator count across the beam, as is achieved when conjugating the adaptive optics element to the pupil plane of the system. In the case of placing the adaptive optics element outside the pupil plane, the beam size must be smaller than the active area of the adaptive optics element as the beam center position must move as a function of the scan angle, as shown in FIG. 31(E). For a given adaptive optics element, this necessarily reduces the actuator count across the beam, which potentially adversely affects wavefront correction. For large field sizes, the advantages offered by placing the adaptive optics element outside the pupil plane of improved correction over a larger field of view outweigh the disadvantage of lower spatial frequency correction over the beam. As the size of the desired field of view decreases, the magnitude of the change in wavefront over the field of view also decreases and the effects of anisoplanatism become less pronounced such that increasing the number of actuators across the beam can be more beneficial to performance than moving the adaptive optics element outside of the pupil plane and closer to conjugation to the source of the aberration. In the limit of a single point field of view, the wavefront does not change at all over the field of view and the best adaptive optics performance will likely be obtained by maximizing the number of actuators across the beam by conjugating the adaptive optics to a pupil plane of the system. In one embodiment of the present invention, the adaptive optics element 715 is conjugated to a pupil plane of the system. In another embodiment of the present invention, the adaptive optics element 715 is conjugated to a plane outside of the pupil plane to improve adaptive optics correction. Improved adaptive optics correction would constitute imaging to a particular Strehl ratio over an enlarged field of view, or imaging over a similar sized field of view, but with improved Strehl ratio within the field of view. As can be seen in FIG. 28(C), the beam pivot point is located at the adaptive optics element. As can be seen in FIG. 29(C) and FIG. 31(C), the beam pivot point is located near, but not at the adaptive optics element. It is in this sense of near that the beam projection module operates with four or more axes of motion and controls an angle and position of the light to preferentially interface the adaptive optics element(s) by creating or accommodating a beam pivot point at or near the adaptive optics element(s).

Ordering of Adaptive Optics Element

Figure 32:
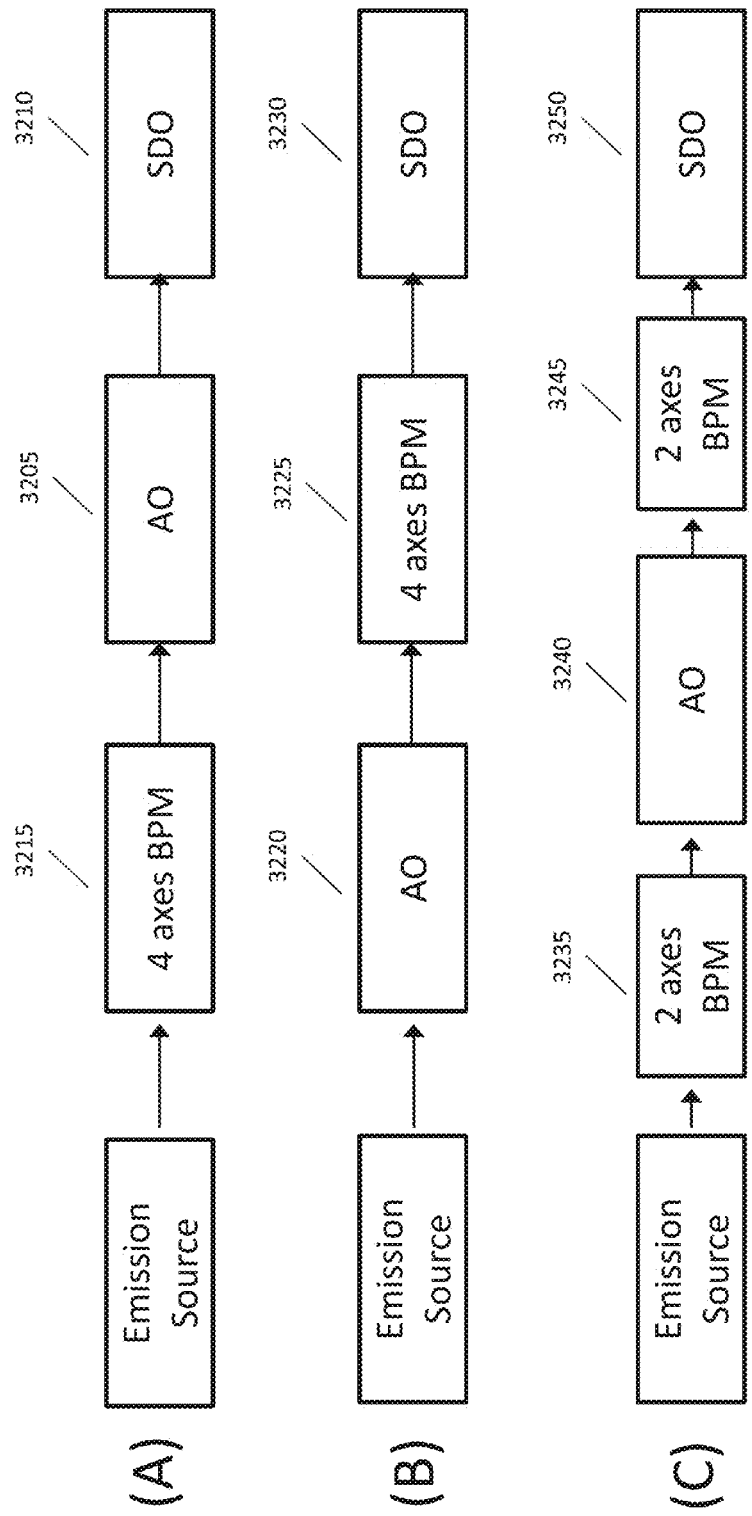
FIG. 32 is a collection of block diagrams showing possible system layouts of an embodiment of the present invention with different ordering of the adaptive optics element relative to the beam projection module.

It is possible to change the ordering of the beam projection module and adaptive optics while still preserving the essential functionality. In one embodiment, the beam projection module 3215 is located before the adaptive optics element(s) 3205 in the system, as shown in FIG. 32(A). This embodiment is generally preferred because the conjugation between the adaptive optics element 3205 and the sample delivery optics 3210 is not affected by path length change within the beam projection module 3215. In another embodiment, the adaptive optics element(s) 3220 in the optical system is located before the beam projection module 3225, as shown in FIG. 32(B). In this configuration, small changes in the optical path length of the beam projection module 3225 may cause a position dependent axial shift in the plane that is conjugate to the adaptive optics element. Another embodiment splits the axes of the beam projection module such that a group of axes 3235 is located before the adaptive optics element 3240 and a group of axes 3245 is located after the adaptive optics element 3240. This configuration also suffers from a change in optical path length which affects the conjugation between the adaptive optics element and the intended plane of conjugation. In one embodiment of the adaptive optics scanning system, the beam projection module 720 directs light to the adaptive optics element(s) such that a center of the light beam remains predominately aligned with a center of the adaptive optics element(s) 715 while the angle of light beam relative to the adaptive optics element(s) 715 is changed during a beam steering operation. In another embodiment of the adaptive optics scanning system, the beam projection module 720 receives light from the adaptive optics element(s) 715 and directs the light such that a center of the light beam remains predominately aligned with a center of a desired pupil plane in the imaging system while the angle of light beam relative to the desired pupil plane is changed during a beam steering operation.

Focus and Conjugation Control

Figure 33:
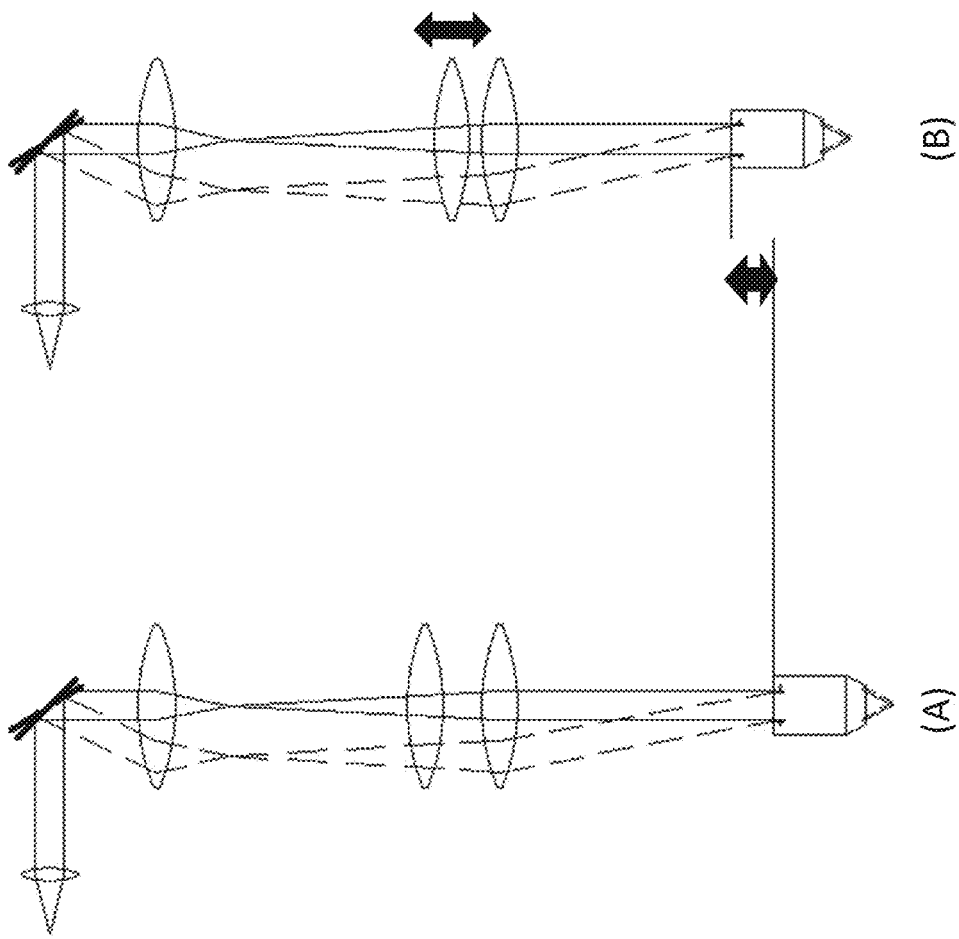
FIG. 33 is a diagram showing how adjustment of optical elements in the sample delivery optics can accommodate motion of the objective lens while maintaining proper conjugation of the objective lens pupil and adaptive optics element.

It is common in microscopy that the objective be able to translate to accommodate different specimen heights and sizes, as well as to focus to a plane of interest in the sample. One embodiment of comprises a means for adjusting the focus in the sample, as shown in FIG. 33. More specifically, an embodiment of the present invention includes the case where the imaging system comprises a means for adjusting the focus by translating a microscope objective, scan lens, or objective lens as part of the sample delivery optics. When the objective location changes, it is still desirable to maintain beam alignment and pupil conjugation with the adaptive optics element. An embodiment of the present invention includes the case where the motion trajectories of the controller change to accommodate changes in focus while maintaining proper alignment of the light beam with the pupil of the sample delivery optics. An embodiment of the present invention also includes the case where optical elements within the sample delivery optics move to accommodate changes in focus while maintaining proper alignment of the light beam with the pupil of the sample delivery optics. It is also possible to affect focus without moving the position of any of the optical elements. An embodiment of the present invention includes the case where a defocus mode is generated with the adaptive optics to achieve focus position control within the sample.

For a variety of reasons related to resolution, field of view, depth of field, and other, it may be desirable to change the sample delivery optics or objective. An embodiment of the present invention includes the case where different objectives can be accommodated that have different pupil positions by adjusting the scan trajectories in the beam projection module, by adjusting or changing optical elements in the sample delivery optics, or adjusting both scan trajectories in the beam projection module and optical elements in the sample delivery optics.

By monitoring light coming out of the objective while scanning, it is possible to infer and assess the quality of optical alignment. An embodiment of the present invention includes the case where a calibration is performed with the objective in place to learn the pupil position of the objective. Further, an embodiment of the present invention includes the case where elements in the sample delivery optics are changeable or adjustable to accommodate different objective pupil diameters, different objective pupil locations, or both different objective pupil diameters and pupil locations. In one possible implementation, a zoom beam expander is used in the sample delivery optics to accommodate different pupil sizes.

Optional Enhancements and Alternative Embodiments

Different adaptive optics technologies and designs have different performance characteristics.

Figure 34:
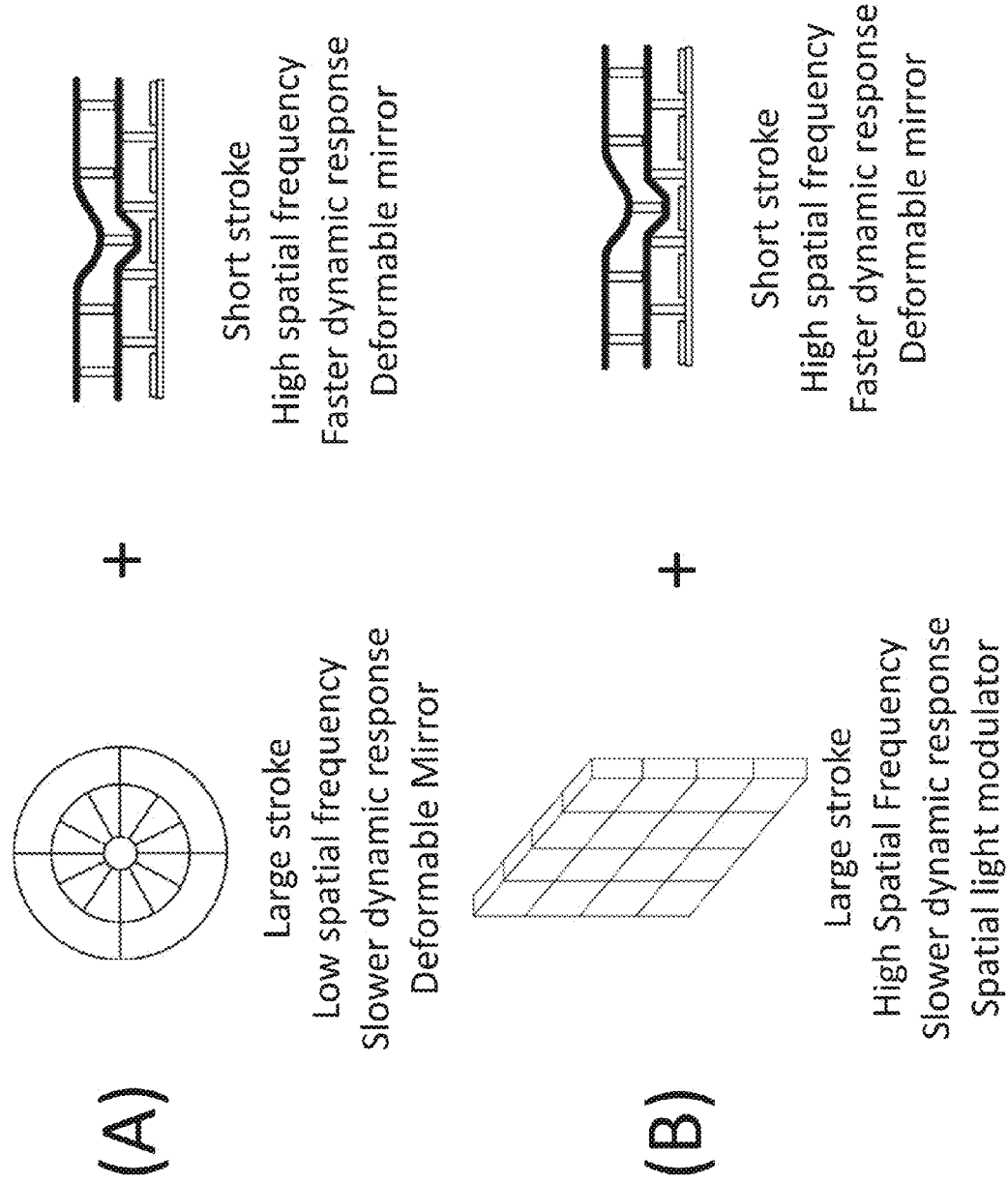
FIG. 34 is a collection of diagrams illustrating several of many different combinations of adaptive optics technologies that can be combined in an embodiment of the present invention.

In one embodiment, the number of adaptive optics elements is two or more and a combination of adaptive optics elements is used to increase the range of wavefront correction, intensity correction, or both wavefront and intensity correction. In one embodiment, the number of adaptive optics elements is two or more and the two or more adaptive optics elements have different correction range, actuator or pixel arrangement, actuator or pixel spacing, or temporal response to achieve a correction that is preferred over using any one of the adaptive optics element alone. In one embodiment, two or more adaptive optics elements are used in a woofer-tweeter configuration, as shown in FIG. 34. A 4f telescope may be used between two adaptive optics elements or the two adaptive optics elements may by located in close proximity to each other. In one embodiment, a liquid crystal spatial light modulator is mounted near the reflective surface of a deformable mirror. This arrangement can be desirable because it allows the deformable mirror and liquid crystal spatial light modulator to be conjugated to nearly the same plane. In one embodiment, a liquid crystal spatial light modulator corrects large amplitude aberrations, but is limited to slow dynamic performance, while the deformable mirror corrects smaller amplitude aberrations, but operates with fast dynamic performance. In another embodiment of the present invention, two or more beam projection modules 720 are used to cascade multiple adaptive optics element(s) 715, each beam projection module 720 operating with four or more axes of motion.

For applications where the optical performance is affected by dispersion, an embodiment of the present invention can include a dispersion compensation unit to compensate for dispersion in the system. One embodiment of the present invention includes a dispersion compensation unit, the dispersion compensation unit being comprised of any one or more of the following: dispersion compensating mirrors (DCM), prisms, glass wedges, gratings, or active dispersion compensation by means of an active deformable mirror or spatial light modulator.

It is possible to perform parallel imaging with two beams in certain imaging modalities. The two beams may originate from two closely spaced fiber optic fiber tips or from two beams with different propagation angles. An embodiment of the present invention includes the case where multiple beams pass through the imaging system to perform parallel spot imaging.

The method of beam steering with the beam projection module 720 has been shown with collimated beams. However the same method works for converging or diverging beams as long as the beam stays within the mirror limits. One embodiment of the present invention uses converging or diverging beams in the beam projection module 720.

Figure 35:
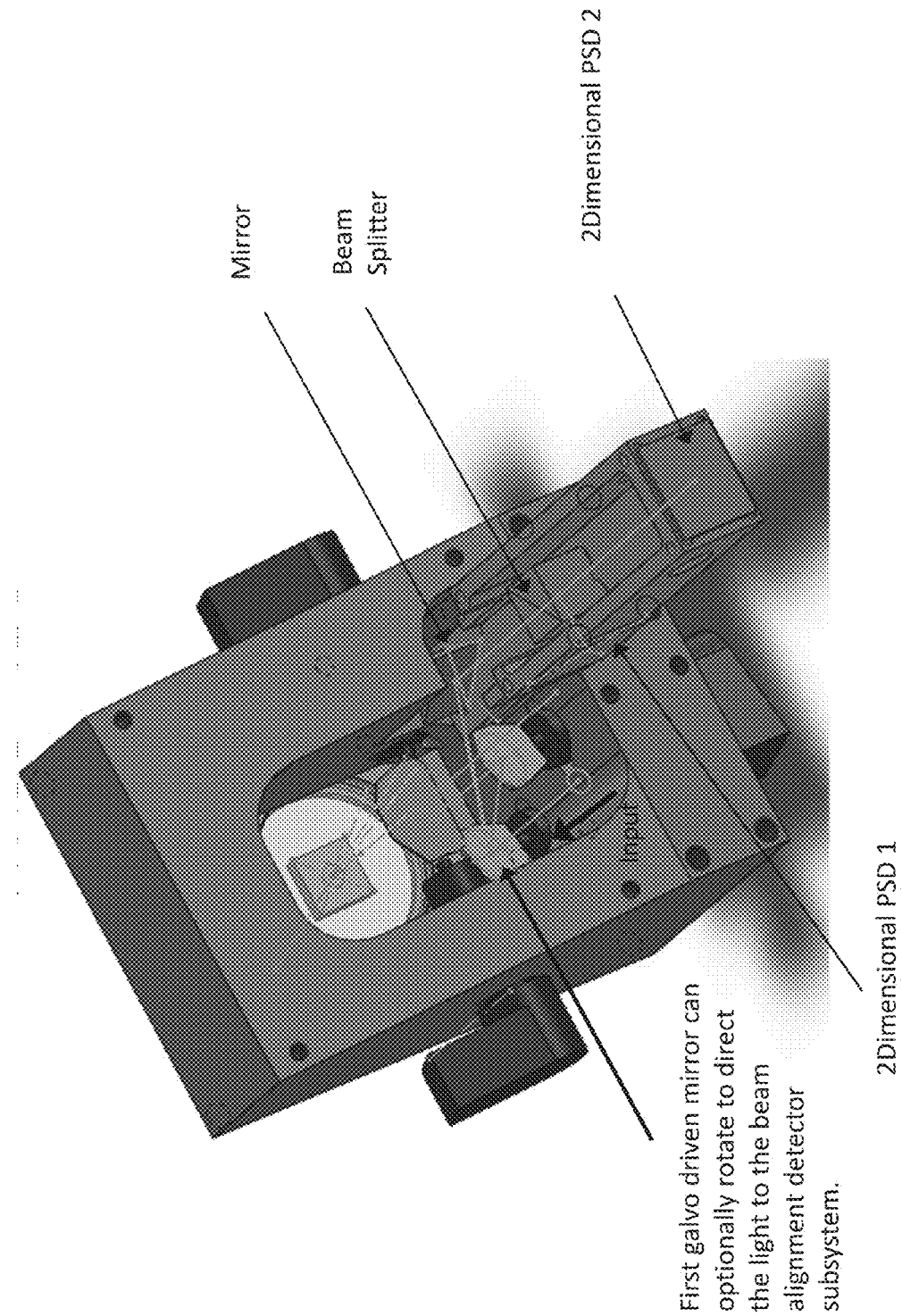
FIG. 35 is a solid model rendering of a beam alignment module that can be used in an embodiment of the present invention to aid in alignment of the instrument.

During setup and alignment of the adaptive optics scanning system, the beam from the emission source often needs to be precisely aligned with the intended optical axis of the optical system. Alignment may drift over time and temperature. It is possible to determine the quality of alignment by monitoring the beam position and using a sensor, as shown in FIG. 35. An embodiment of the present invention includes the case where one or more position sensing or angle sensing detector(s) is used to determine the accuracy of incoming beam alignment to the beam projection module from the emission source and information used about the beam alignment to correct for misalignment by adjusting the scan trajectories of the active axes. Further, the sensor for monitor the beam position and alignment may be included in the optical path by changing one or more of the active mirrors in the beam projection module to direct light from the normal imaging path to the alignment detector, as shown in FIG. 35. One embodiment of the present invention includes one or more 1D or 2D detector(s), such as CCD array, CMOS array, or position sensing diode (PSD), or any other detector that can measure a beam position is used to monitor the beam position with or without a small beam splitter or additional mirror to check the quality of beam alignment.

Adaptive Optics Control

Figure 36:
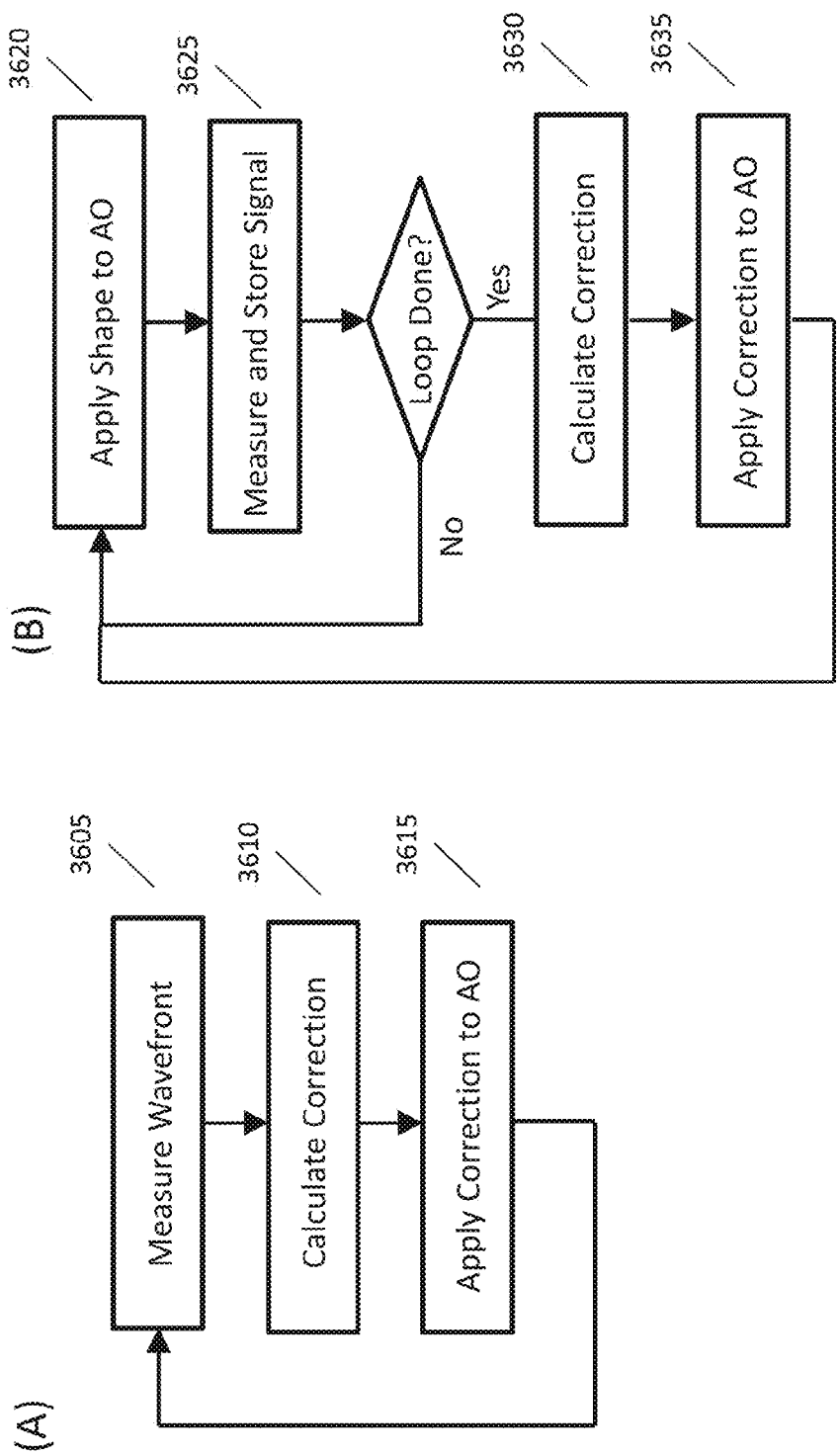
FIG. 36 is a set of block diagrams showing adaptive optics control algorithms of an embodiment of the present invention.

In adaptive optics systems, it is common that light from a point source (guide star) be used to estimate the optical aberrations. One embodiment of the present invention includes a wavefront sensor for measuring an aberration in the light from the sample or a point source within the sample. In this embodiment, the imaging system may determine an appropriate adaptive optics correction by using information about the aberration obtained with the wavefront sensor, as shown in FIG. 36(A). When using a wavefront sensor, an algorithm for adjusting the deformable mirror that is commonly used in practice is to execute the steps of measuring the wavefront 3605, calculating an adaptive optics correction 3610, and applying the correction to the adaptive optics element 3615. Most adaptive optics systems place the wavefront sensor before the scanners so that the beam entering the wavefront sensor is collinear with the excitation beam being directed to the sample. A dichroic mirror or beam splitter and a light source for the beacon would be located between the emission source 705 and beam projection module 720 of an embodiment of the present invention to generate the guide star for the wavefront sensor, as taught in the before mentioned Dubra 2011 paper. Alternatively, the wavefront sensor could be located after the beam projection module 720 and a dichroic mirror or beamsplitter included with appropriate pupil relay as part of the sample delivery optics 730. The advantage of locating the wavefront sensor after the beam projection module is that the conjugate of the wavefront sensor to the pupil does not change with beam steering position, however, the excitation beam must be precisely centered so as to not introduce significant tilt modes into the wavefront sensor measurement. The advantage of locating the wavefront sensor before the beam projection module are that tilt modes are not introduced while scanning, however there may be a small path length change during scanning that affects the conjugation of the wavefront sensor to the plane of conjugation.

Figure 37:
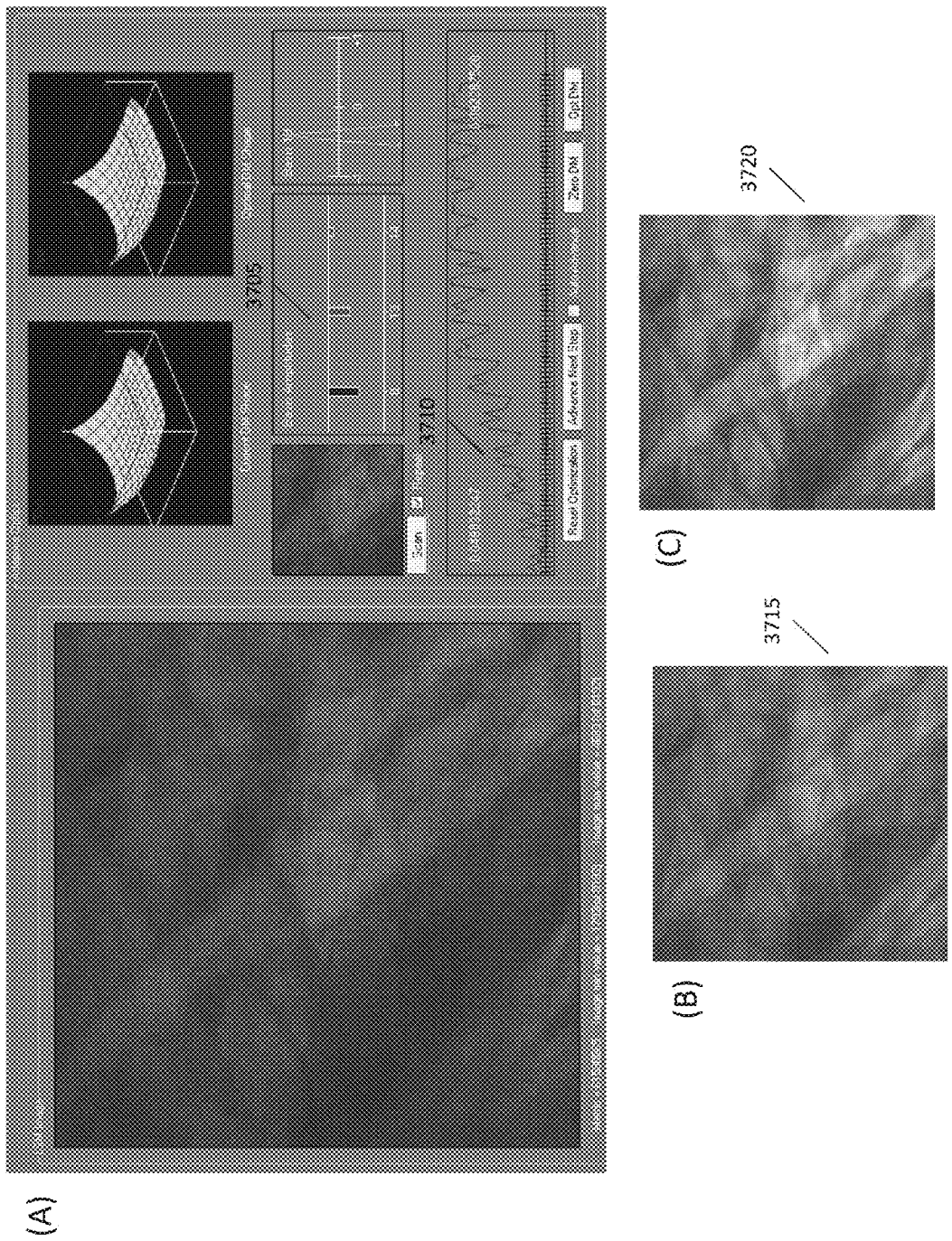
FIG. 37 is an image of a screen capture showing adaptive optics control with a reduced basis set.

Other methods exist for determining the proper adaptive optics correction. One technique, often referred to as wavefront sensorless adaptive optics, optimizes the adaptive optics component using information from the image or sample signal alone. Papers that teach algorithms for sensorless adaptive optics include "Image based adaptive optics through optimisation of low spatial frequencies" by D. Debarre, M. Booth, and T. Wilson, Opt. Express 15, 8176-8190 (2007), "Image-based adaptive optics for two-photon microscopy" by D. Débarre, E. Botcherby, T. Watanabe, S. Srinivas, M. Booth, and T. Wilson, Opt. Lett. 34, 2495-2497 (2009), and others "Adaptive optics via pupil segmentation for high-resolution imaging in biological tissues" by N. Ji, D. Milkie, and E. Daniel, Nature Methods, 7, 141-147 (2009). In wavefront sensorless adaptive optics control, there is often an iterative loop of perturbing the adaptive optics element to obtain input/output data between the adaptive optics element and the signal, as shown in FIG. 36(B). The inner loop consists of steps of applying shapes (basis functions, or sometimes called modes) to the adaptive optics element 3620 and measuring and storing the signal response 3625. The results of the inner loop are used to calculate an adaptive optics correction 3630, which is then followed by applying the correction to the adaptive optics element 3635. One embodiment of the present invention determines an appropriate adaptive optics correction by using a wavefront sensorless adaptive optics optimization method. Many wavefront sensorless methods apply a series of shapes or alternatively called basis functions, or modes to the adaptive optics element as part of the optimization process. The quality of correction can be assessed by calculating a metric associated with a measurement of the light returning from the sample with the detector. An embodiment of the present invention includes the case where the adaptive optics optimization methods generate a series of adaptive optics shapes, applies the shapes to the imaging system, assesses the impact of the shapes by calculating a metric value based on measurements of the light from the detector, and updates the adaptive optics element to improve image or signal quality. The metric is usually a measure of signal quality, contrast, or spatial frequency content, as taught in the before mentioned papers (Debarre, 2007, Debarre 2009, Ji, 2009). The optimization algorithm can be any one of many optimization algorithms know in the field of optimization, including Newton's method, quasi-Newton methods, gradient descent, conjugate gradient, genetic algorithms, simulated annealing, hill climbing, polynomial interpolation, or other optimization algorithm known in the art of numerical optimization Optimization of the adaptive optics can be performed by zonal or modal control methods. In zonal methods, local regions of the adaptive optics actuators or pixels are controlled separately. In modal control methods, multiple actuators or pixels are controlled simultaneously with a set of basis shapes. When using modal techniques, one embodiment of the present invention uses profiles of the adaptive optics mode shapes that are predominately orthogonal to improve the rate of convergence of an optimization algorithm. Certain modes of aberration correction do not improve the image quality. For example, piston changes the absolute phase of the wavefront, but not the resulting point spread function (PSF). Tip and tilt steer the beam, but do not affect the image quality. It is therefore sometimes desirable to remove piston, tip, and tilt from the modes controlling the adaptive optics element. An embodiment of the present invention includes the case where the profiles of the adaptive optics shapes are generated to avoid including portions of piston, tip, and tilt modes. In some circumstances, certain mode shapes are more important than others. Optimization can be performed on a subset of modes, as shown in FIG. 37. Only three basis shapes (modes) are used in the optimization, as shown by the plot 3705 showing the basis amplitudes. The convergence plot 3710 shows the progress of the optimization algorithm. An image of the sample with the deformable mirror flat 3715 is compared to an image of the sample with the deformable mirror optimized 3720. The image of the sample with the deformable mirror optimized 3720 shows increased signal and improved resolution when compared to the image of the sample with the deformable mirror flat 3715.

Many imaging modalities are depth sectioning imaging modalities, such as confocal, multiphoton, and others. For sectioning imaging modalities, it is desirable to correct image degrading aberrations at a particular focal depth in the sample. In this case, it is desirable to remove any defocus mode from the basis set controlling the adaptive optics element. An embodiment of the present invention includes the case where the profiles of the adaptive optics corrections are generated to avoid including portions of defocus modes. Given an optimized adaptive optics state for a particular region in a sample, it is likely that regions nearby will have similar aberrations. It is therefore possible to initialize the adaptive optics with a state for a nearby region to decrease the time required to achieve convergence. Information about an appropriate adaptive optics correction from more than one region can be combined with the goal of improving the estimate for a new region in the sample. An embodiment of the present invention includes the case where information about an appropriate adaptive optics correction for a first location or multiple locations within the sample is used to estimate an appropriate adaptive optics correction for a new location within the sample.

When performing OCT imaging, frequency and phase information contained within the OCT fringe contain information about the path length of light coming from the sample. The information encoded in the OCT fringe can be used to estimate a wavefront. In confocal or multi-photon imaging, methods such as blind deconvolution can be used to estimate a point spread function, an object, and a wavefront. One embodiment of the present invention uses a wavefront estimated from OCT data or from image processing methods, such as blind deconvolution, as part of the optimization processes for determining a correction for the adaptive optics element 715.

In optical tweezer systems, the adaptive optics can be optimized using algorithms such as those taught in a paper, "Holographic optical tweezers aberration correction using adaptive optics without a wavefront sensor" by K D. Wulff, D G. Cole, R L. Clark, R D Leonardo, J Leach, J Cooper, G Gibson, M J Padgett, Proc. SPIE 6326, Optical Trapping and Optical Micromanipulation III, 63262Y (2006) and "Combined holographic-mechanical optical tweezers: Construction, optimization, and calibration", by R D L Hanes, M C Jenkins, and SU. Egelhaaf, Rev. Sci. Instrum. 80, 083703 (2009).

Beam Switching

Figure 38:
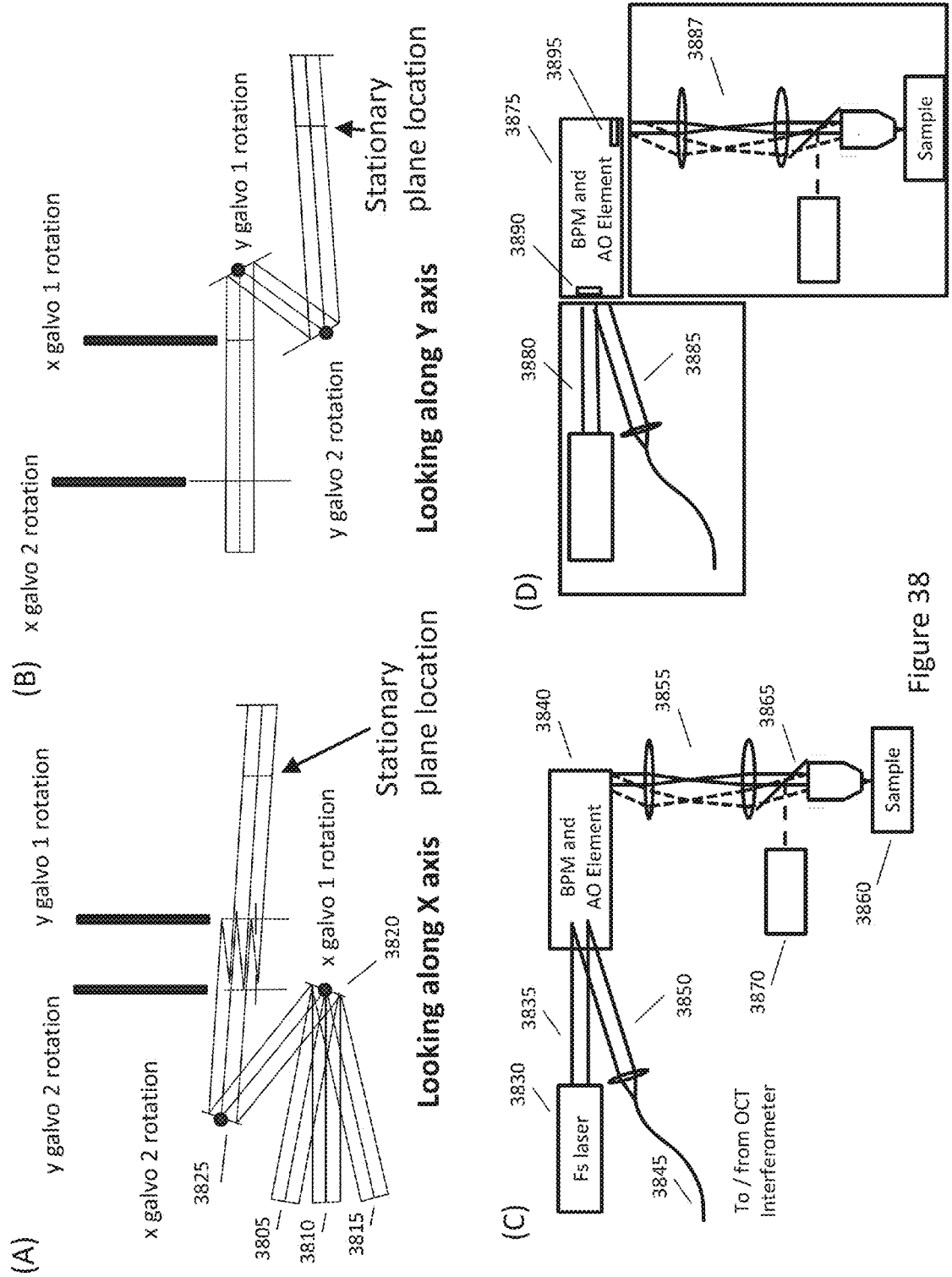
FIG. 38 is a collection of diagrams showing beam switching, a modular adaptive optics unit, and multiple beam entrance and exit ports of a modular adaptive optics unit of an embodiment of the present invention.

FIG. 38(A) shows a diagram of a beam projection module viewed along the x axis and FIG. 38(B) shows a diagram of the same beam projection module viewed along the y axis. Three different input beams 3805, 3810, and 3815 are aimed such that they cross at a point that is coincident with a steering mirror 3820. The angle between the incoming beams is small enough that rotation of the steering mirror 3820 enables selecting which of the input beams 3805, 3810, or 3815 is passed through the optical system. If the angle between the incoming beams 3805, 3810, and 3815 is too small, then it is possible that an unintended portion of an inactive beam also pass through the optical system. Unintended transmission of a beam through the optical system can be prevented by ensuring that the angle between the beams is large enough that the distance between beam edges at the mirror 3825 is larger than the mirror surface. Unintended transmission of a beam through the optical system can be prevented by ensuring that the angle between the beams is large enough that a field stop within the optical system blocks transmission of the unintended beam. Capability of switching between input beams could be desirable when performing multiple modes of imaging. A single instrument can perform different imaging modalities by switching between emission sources and other related systems. For example, a combined two-photon and OCT imaging system might use a Titanium Sapphire laser centered around 850 nm and an OCT system centered around 850 nm, 1050 nm, or 1310 nm. Light from the Titanium Sapphire laser 3830 generates a beam 3835 that is directed to the beam projection module 3840. Light from the OCT system is delivered by a fiber optics cable 3845 and collimated into a beam 3850 that is also directed into the beam projection module 3840. The beam projection module enables switching between the two input beams to direct the light through sample delivery optics 3855 to a sample 3860. In the mode of two-photon imaging, excitation light passes through a long pass filter 3865, while fluorescent emission light from the sample reflects off the long pass filter 3865 and is directed to a PMT detector 3870. In the mode of OCT imaging, light centered around 850 nm, 1050 nm, or 1310 nm passes through the long pass filter 3860 in the direction towards the sample and also passes backscattered and reflected light from the sample 3860 through the long pass filter and back through the beam projection module to the OCT interferometer. Using a multimodal imaging system, additional information can be gathered about the sample and equipment can be timeshared for different imaging modalities in a compact installation.

Modular Adaptive Optics Unit

The basic concept of the beam steering module and adaptive optics element as previously described can be considered as a modular adaptive optics unit for adaptation to other instruments. The modular adaptive optics unit could be sold as a stand alone module for the user to integrate with their own optical system, as an original equipment manufacturer (OEM) module, or as part of an integrated system. One embodiment of the beam steering module and adaptive optics element portion of a modular adaptive optics unit are shown in FIGS. 13-15. As shown in FIG. 38(D), one embodiment of the modular adaptive optics unit is comprised of one or more entrance ports, the entrance ports allowing one or more optical beams to enter the modular adaptive optics unit as shown in FIG. 38(A), one or more output ports, the output ports being located along one or more beam paths at which the optical beam may transit or be terminated, one or more adaptive optics element(s), the adaptive optics element(s) affecting the wavefront, affecting the intensity, or affecting both the wavefront and intensity of the light beam, a set of beam steering elements, the beam steering elements creating four or more axes of motion that affect the angle of, and/or the transverse position of, the propagation path of the light to preferentially create at least one effective rotation point about which the light beam is pivoted, and a means for controlling the trajectories of the beam steering elements to direct the light beam along preferential paths. The entrance ports and output ports may be physical ports or simply different optical paths. The means for controlling the trajectories include all means for controlling the trajectories previously discussed for the controller 725.

In FIG. 38(D), an embodiment of a modular adaptive optics unit 3875 receives light from a first beam 3880 and a second beam 3885 and directs light to an optical subsystem 3887.

In an optical system one may wish to condition light beams or to protect certain optical elements from contamination or by limiting access to these certain elements. To achieve this goal one or more of the entrance ports 3890 and output ports 3895 of one embodiment of the modular adaptive optics unit 3875 contain any combination of the following: optical window, an optical filter, a band-pass filter, a notch filter, a long-pass filter, a short-pass filter. This list is not to be considered a complete list of possible optical elements that may be used in these ports; but, it is a sampling of common elements that may be used. These elements may be fixed or removable. In one embodiment of the modular adaptive optics unit, one or more optical filters are removable.

The adaptive optics element of one embodiment of the modular adaptive optics unit 3875 may include one or more deformable mirrors. One embodiment of a modular adaptive optics unit comprises an adaptive optics element(s) that is a deformable mirror. Deformable mirrors of an embodiment of the modular adaptive optics unit may comprise a continuous facesheet or a segmented facesheet, electrostatic actuators, piezo-electric actuators, unimorph piezo actuators, bimorph piezo actuators, pneumatic actuators, or other equivalent means to deform the facesheet. Examples of these deformable mirror elements are shown in FIG. 3. Deformable mirrors in one embodiment of the modular adaptive optics unit may be of MEMs type structure, membrane type structure, layered piezo type structure, tip/tilt/piston or tip/tilt element type structure, or other type structure able to repeatedly change the shape of, orientation of, or shape and orientation of the mirror surface.

The adaptive optics element of an embodiment of the modular adaptive optics unit 3875 may include one or more spatial light modulators. One embodiment of the modular adaptive optics unit uses an adaptive optics element that is a spatial light modulator. Spatial light modulators may be based on liquid crystal elements or other methods to modulate the intensity, modulate the phase, or modulate both the phase and intensity. Examples are show in FIG. 3. Spatial light modulators may be used to compensate for wavefront aberrations or intensity variations caused to the optical beam before or after the adaptive optics element. Wavefront and intensity of a beam propagating through an optical system may be affected by medium through which it travels. These medium include, but is not limited to, gas, liquid, optical windows, glass elements, tissue, filters, lenses, mirrors, diffractive optical elements, active or passive crystals. One embodiment of the modular adaptive optics unit uses an adaptive optics element(s) to compensate for wavefront aberrations, or intensity variations, or wavefront aberrations and intensity variations, caused to the optical beam by propagating through an optical medium or optical elements that comprise gas, liquid, optical windows, glass elements, tissue, filters, lenses, mirrors, diffractive optical elements, active or passive crystals, after transmitting toward and through at least one output port 3895.

Depending on the amount of wavefront or intensity variations in an optical beam, two or adaptive optics elements may be used to increase the magnitude of these variations that may be corrected. The adaptive optics elements may or may not be substantially similar to each other. They may be used to statically compensate for the variations or compensation may be varied temporally. For example, in one embodiment of the modular adaptive optics unit, two or more adaptive optics elements with different designs may be used such that the two or more adaptive optics elements have different correction range, or actuator arrangement, or spacing, or temporal response, or any combination of these parameters to achieve a correction that is preferred over using one adaptive optics element alone.

Many adaptive optics systems use optical relays as shown in FIG. 6 to properly manage the requirements of beam pivot locations in the optical system. The modular adaptive optics unit includes a beam projection module for generating a pivot location for the beam at an appropriate location in the optical system. The beam projection module has four or more axes of motion that affect mirrors to properly guide the beam. One embodiment of the modular adaptive optics unit includes the case where the axes of motion comprise at least one rotational axis. One modular adaptive optics unit embodiment includes the case where the axes of motion comprise at least one translational axis. One modular adaptive optics unit includes the case where the axes of motion comprise a combination of rotational and translational axes. One embodiment of the modular adaptive optics unit uses beam steering elements comprising at least one galvanometer driven mirror. One embodiment of the modular adaptive optics unit of uses beam steering elements comprising four galvanometer driven mirrors. One embodiment of the modular adaptive optics unit uses beam steering elements comprising at least one fast steering mirror, the fast steering mirror having two axes of rotation. One embodiment of the modular adaptive optics unit uses beam steering elements comprising two fast steering mirrors, the two fast steering mirrors having two axes of rotation. One embodiment of the modular adaptive optics unit that uses beam steering elements comprising at least one resonant scanning mirror. One embodiment of the modular adaptive optics unit using beam steering elements comprising singly or in any combination of the following: a steering mirror, acousto-optic deflector, rotating polygon, electro-optic beam deflector, electro-optic prism, thermo-optic prism, or diffractive array.

One embodiment of the modular adaptive optics unit operates with the coordination between the multiple axes of motion controlled through electronic signals to the actuators or active elements. One embodiment of the modular adaptive optics unit embodiment operates with the coordination between these axes of motion controlled through a mechanical linkage. Trajectories along which one may wish to control the axes of motion to direct the beam of light are varied. One embodiment of the modular adaptive optics unit embodiment operates with a means for controlling the trajectories of the axes of motion changing the path of the light beam so that it traces a raster scan pattern in at least one output port, or at a defined plane in an optical system that receives the light beam through at least one output port. One embodiment of the modular adaptive optics unit uses beam steering elements to direct the light beam to the adaptive optics element(s) such that a center of the light beam remains predominately aligned with a center of the adaptive optics element(s) while the angle of incidence of light beam relative to the adaptive optics element is varied by the means for controlling the trajectories of the axes of motion. One embodiment of the modular adaptive optics unit uses beam steering elements to receive light from the adaptive optics element(s) and direct the light beam such that an apparent center of rotation of the light beam remains predominately aligned relative to a point located in a defined plane while the angle of light beam is varied by the trajectories of the axes of motion, wherein the defined plane is located along a beam path after the beam steering elements.

As mentioned earlier, multiple adaptive optics elements may be required to compensate variations in wavefront or intensity or both wavefront and intensity. One modular adaptive optics unit embodiment includes the case where two or more beam projection modules are used to cascade multiple adaptive optics elements, such that each beam projection module operates with four or more axes of motion.

One modular adaptive optics unit embodiment of the adaptive optics scanning system includes the case where a 4f optical relay is used to match the active area of the integrated adaptive optics element to an optical system receiving the light beam from adaptive scanning system. One modular adaptive optics unit embodiment includes the case that a 4f optical relay is used to relay the wavefront incident on the adaptive optical element to a conjugate plane before, substantially at, or after at least one said exit port to enable interfacing said adaptive optics scanning system to an optical system receiving said light beam from at least one said output port. FIG. 6 shows a typical 4f relay that would be used to relay a wavefront from one plane to another.

One modular adaptive optics unit embodiment includes the case where the 4f optical relay comprises reflective optical elements, refractive optical elements, or a combination of reflective and refractive optical elements. One modular adaptive optics unit embodiment includes the case where the 4f optical relay has variable magnification. One modular adaptive optics unit embodiment includes the case where one or more 4f optical relays may be used to interface the adaptive optics scanning system to an optical system receiving the light beam from at least one output port of the adaptive optics scanning system, where the 4f optical relay helps to overcome space constraint related to a short distance between a pupil plane in the optical system and the first optical element of the adaptive optics scanning system.

Many scanning laser systems are used in applications that require pulsed lasers as the light source. Short pulse lasers provide the ability to input short bursts of optical energy into a system with relatively high peak powers, where the optical wavelength range is substantially broader than a CW laser and is centered at or near a desired wave length. The wavelength spectrum emitted by pulsed lasers may be tailored, within certain operating parameters' limits, to the application. If the application requires pulses durations at the beam termination point to be substantially near a certain value, dispersion compensating elements or systems may be required to compensate for the deleterious affect optical materials have on the optical pulse duration, and thereby the optical spectrum. One modular adaptive optics unit embodiment of the adaptive optics scanning system includes the case where dispersion compensating elements or systems may be used to compensate for dispersion in the light beam caused by optical material that was "seen" by the beam before the dispersion compensating elements or systems, or to pre-compensate for dispersion in the light beam caused by optical material that would be "seen" by the beam after the dispersion compensating elements or systems. One modular adaptive optics unit embodiment includes the case where the dispersion compensating elements or systems may include, but not be limited to, multilayer dielectric mirrors, optical prisms, diffractive optical elements, holographic optical elements, liquid crystal optical elements, programmable diffractive optical elements, programmable pulse shapers, either as independent dispersion compensating elements or in combination to achieve a desired amount of dispersion compensation.

While the present invention has been described at some length and with some particularity with respect to the several described embodiments, it is not intended that it should be limited to any such particulars or embodiments or any particular embodiment, but it is to be construed with references to the appended claims so as to provide the broadest possible interpretation of such claims in view of the prior art and, therefore, to effectively encompass the intended scope of the invention. Furthermore, the foregoing describes the invention in terms of embodiments foreseen by the inventor for which an enabling description was available, notwith-

What is claimed is:

1. A method for scanning a sample, the method comprising:
generating a first light from an emission source;
directing the first light to one or more adaptive optics element(s), the adaptive optics element(s) affecting the wavefront, affecting the intensity, or affecting both the wavefront and intensity of the first light;
controlling an angle and position of the first light with four or more axes of motion to preferentially interface the adaptive optics element by creating or accommodating a beam pivot point at or near the adaptive optics element(s) while scanning the first light across the sample;
controlling motion trajectories of the four or more axes of motion;
conditioning and directing the first light to the sample; and
measuring a second light from the sample.

2. The method of claim 1, further comprising performing imaging of the sample.

3. The method of claim 1, further comprising performing optical coherence tomography (OCT).

4. The method of claim 1, further comprising generating the first light with a laser.

5. The method of claim 1, further comprising:
measuring an aberration in a third light from the sample or a point source within the sample; and
determining an appropriate adaptive optics correction by using information about the aberration.

6. The method of claim 1, further comprising determining an appropriate adaptive optics correction by using a wavefront sensorless adaptive optics optimization method.

7. The method of claim 1, wherein controlling an angle and position of the first light is performed using four galvanometer driven mirrors.

8. The method of claim 1, wherein controlling an angle and position of the first light is performed using two fast steering mirrors.

9. The method of claim1, wherein controlling an angle and position of the first light is performed using at least one MEMS mirror.

10. The method of claim1, further comprising switching between at least a first and a second emission sources using at least one axis of the four or more axes of motion.

11. The method of claim 10, further comprising performing OCT imaging with the first emission source and microscopy imaging with the second emission source.

12. The method of claim 1, further comprising performing different imaging modalities by switching between emission sources.

13. A method for scanning a sample, the method comprising:
generating a first light from an emission source;
directing the first light to one or more adaptive optics element(s), the adaptive optics element(s) affecting the wavefront, affecting the intensity, or affecting both the wavefront and intensity of the first light, wherein the adaptive optics element(s) is (are) conjugated to a plane(s) outside of the pupil plane to improve adaptive optics correction of aberrations associated with the sample;
controlling an angle and position of the first light with two or more axis of motion to preferentially interface the adaptive optics element by creating or accommodating a beam pivot point at or near the adaptive optics element(s) while scanning the first light across the sample, wherein a light beam center of the first light moves on the adaptive optics elements(s) surface;
controlling motion trajectories of the two or more axes of motion;
conditioning and directing the first light to the sample; and
measuring a second light from the sample.

14. The method of claim 13, wherein at least one adaptive optics element is conjugated to a plane that is at or near a source of aberration.

15. An adaptive optics scanning system comprising:
an emission source for generating a first light, the first light being directed through the adaptive optics scanning system to a sample;
one or more adaptive optics element(s), the adaptive optics element(s) affecting the wavefront, affecting the intensity, or affecting both the wavefront and intensity of the first light, wherein the adaptive optics element(s) is (are) conjugated to a plane(s) outside of the pupil plane to improve adaptive optics correction of aberrations associated with the sample;
an optical subsystem, the optical subsystem operating with two or more axes of motion and controlling an angle and position of the first light to preferentially interface the adaptive optics element by creating or accommodating a beam pivot point at or near the adaptive optics element(s) while scanning the first light across the sample, wherein a light beam center of the first light moves on the adaptive optics element(s) surface;
a controller for controlling motion trajectories of the two or more axes in the optical subsystem;
sample delivery optics, the sample delivery optics appropriately conditioning and directing the first light to the sample; and
one or more detector(s), the detector(s) measuring a second light from the sample.

16. The adaptive optics scanning system of claim 15, wherein at least one adaptive optics element is conjugated to a plane that is at or substantially near a source of aberration.

17. The adaptive optics scanning system of claim 15, wherein the optical subsystem comprises at least one 4f relay.

18. The method of claim 13, further comprising determining an appropriate adaptive optics correction by using a wavefront sensorless adaptive optics optimization method.

19. The adaptive optics scanning system of claim 15, wherein the sample delivery optics comprise a microscope objective and wherein the adaptive optics scanning system performs laser scanning microscopy.

20. The adaptive optics scanning system of claim 15, further comprising an interferometer, wherein the adaptive optics scanning system performs optical coherence tomography.

* * * * *